US007884083B2

(12) United States Patent
Van Nest et al.

(10) Patent No.: US 7,884,083 B2
(45) Date of Patent: Feb. 8, 2011

(54) IMMUNOMODULATORY COMPOSITIONS, METHODS OF MAKING, AND METHODS OF USE THEREOF

(75) Inventors: Gary Van Nest, Martinez, CA (US); Stephen Tuck, Oakland, CA (US)

(73) Assignee: Dynavax Technologies Corporation, Berkeley, CA (US)

(*) Notice: Subject to any disclaimer, the term of this patent is extended or adjusted under 35 U.S.C. 154(b) by 2165 days.

(21) Appl. No.: 10/640,172

(22) Filed: Aug. 12, 2003

(65) Prior Publication Data

US 2009/0017075 A1    Jan. 15, 2009

Related U.S. Application Data

(60) Provisional application No. 60/402,968, filed on Aug. 12, 2002.

(51) Int. Cl.
| A61K 39/00 | (2006.01) |
| A61K 39/38 | (2006.01) |
| A61K 45/00 | (2006.01) |
| A61K 47/00 | (2006.01) |
| A61K 38/00 | (2006.01) |
| A61K 38/16 | (2006.01) |
| A61K 9/14 | (2006.01) |
| A61K 31/70 | (2006.01) |
| A01N 43/04 | (2006.01) |
| A01N 37/18 | (2006.01) |

(52) U.S. Cl. ............... 514/44 R; 424/184.1; 424/278.1; 424/439; 424/489; 514/8

(58) Field of Classification Search ...................... None
See application file for complete search history.

(56) References Cited

U.S. PATENT DOCUMENTS

| 4,458,066 A | 7/1984 | Caruthers et al. |
| 4,587,329 A | 5/1986 | Tomalia et al. |
| 4,650,675 A | 3/1987 | Borel et al. |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,171,264 A | 12/1992 | Merrill |
| 5,338,532 A | 8/1994 | Tomalia et al. |
| 5,453,496 A | 9/1995 | Caruthers et al. |
| 5,484,596 A | 1/1996 | Hanna, Jr. et al. |
| 5,552,391 A | 9/1996 | Coutts et al. |
| 5,709,879 A * | 1/1998 | Barchfeld et al. ........... 424/450 |
| 5,744,166 A | 4/1998 | Illum |
| 6,086,901 A * | 7/2000 | O'Hagan et al. ......... 424/283.1 |
| 6,117,657 A | 9/2000 | Usman et al. |
| 6,177,414 B1 | 1/2001 | Tomalia et al. |
| 6,299,884 B1 * | 10/2001 | Van Nest et al. ......... 424/283.1 |
| 6,306,405 B1 | 10/2001 | O'Hagan et al. |
| 6,406,705 B1 | 6/2002 | Davis et al. |
| 6,451,325 B1 | 9/2002 | Van Nest et al. ......... 424/283.1 |
| 6,453,125 B2 * | 9/2002 | Shono ....................... 396/287 |
| 6,458,370 B1 * | 10/2002 | O'Hagan et al. ......... 424/278.1 |
| 6,544,518 B1 | 4/2003 | Friede et al. |
| 6,558,670 B1 | 5/2003 | Friede et al. |
| 6,613,751 B2 | 9/2003 | Raz et al. ..................... 514/44 |
| 6,809,217 B1 * | 10/2004 | Colley et al. ................. 560/231 |
| 7,129,222 B2 * | 10/2006 | Van Nest et al. ......... 514/44 A |
| 7,183,111 B2 * | 2/2007 | Van Nest et al. ......... 514/44 R |
| 7,223,398 B1 * | 5/2007 | Tuck et al. ............... 424/184.1 |
| 7,250,403 B2 * | 7/2007 | Van Nest et al. ......... 514/44 A |
| 7,255,868 B2 * | 8/2007 | Fearon et al. ............ 424/280.1 |
| 7,479,285 B1 * | 1/2009 | Van Nest et al. ......... 424/278.1 |
| 7,553,397 B1 * | 6/2009 | Colley et al. ................ 203/14 |
| 7,628,990 B2 * | 12/2009 | Tuck et al. ............... 424/184.1 |
| 7,718,622 B2 * | 5/2010 | Tuck et al. .................... 514/43 |
| 7,727,712 B2 * | 6/2010 | Van Nest et al. ................ 435/5 |
| 7,745,606 B2 * | 6/2010 | Dina et al. ................. 536/24.2 |
| 2003/0175731 A1 | 9/2003 | Fearon et al. |
| 2003/0199466 A1 | 10/2003 | Fearon et al. |
| 2003/0225016 A1 | 12/2003 | Fearon et al. |
| 2006/0058254 A1 * | 3/2006 | Dina et al. ..................... 514/44 |
| 2008/0181909 A1 * | 7/2008 | Fearon et al. ............ 424/194.1 |
| 2009/0017075 A1 * | 1/2009 | Van Nest et al. ......... 424/275.1 |
| 2009/0068208 A1 * | 3/2009 | Hessel et al. ............. 424/184.1 |
| 2009/0148479 A1 * | 6/2009 | Van Nest et al. ......... 424/278.1 |
| 2009/0196915 A1 * | 8/2009 | Van Nest et al. ............ 424/450 |

FOREIGN PATENT DOCUMENTS

| EP | 0313 219 | 5/1996 |
| JP | 2001-517613 A | 10/2001 |
| WO | WO 89/02439 | 3/1989 |
| WO | WO 95/07073 | 3/1995 |
| WO | WO 96/40197 | 12/1996 |
| WO | WO 97/28259 | 8/1997 |

(Continued)

OTHER PUBLICATIONS

Marshall et al, Cellular Immunology, 2004, 229:93-105.*
Malyala et al, Advanced Drug Delivery Reviews, 2009, 61:218-225.*
O'Hagan et al, Immunological Reviews, 2004, 199:191-200.*
Sung et al, Curr. Opin. Mol. Ther., 2006, 8/2:150-155.*
Borges et al, Eur. J. Pharm. Biopharm. 2008, 69/2:405-416.*

(Continued)

Primary Examiner—N. M Minnifield
(74) Attorney, Agent, or Firm—Morrison & Foerster LLP

(57) ABSTRACT

The invention relates to new immunomodulatory compositions which comprise a cationic condensing agent, an immunomodulatory compound, and a stabilizing agent. The compositions of the invention typically form particles which have increased immunomodulatory activity as compared to immunomodulatory compounds not formulated in the compositions of the invention. Also provided are methods of making the compositions and methods for therapeutic use of the compositions.

37 Claims, No Drawings

FOREIGN PATENT DOCUMENTS

| | | |
|---|---|---|
| WO | WO 97/46251 | 12/1997 |
| WO | WO 98/16247 | 4/1998 |
| WO | WO 98/55495 | 12/1998 |
| WO | WO 99/11275 | 3/1999 |
| WO | WO-99/15150 A1 | 4/1999 |
| WO | WO 99/62923 | 12/1999 |
| WO | WO-00/15825 A1 | 3/2000 |
| WO | WO 00/34231 | 6/2000 |
| WO | WO-00/50006 A2 | 8/2000 |
| WO | WO-00/50006 A3 | 8/2000 |
| WO | WO 00/75105 | 12/2000 |
| WO | WO 01/15726 | 3/2001 |
| WO | WO-02/02138 A1 | 1/2002 |
| WO | WO 03/061629 * | 7/2003 |
| WO | WO 03/068169 * | 8/2003 |
| WO | WO 2004/014322 * | 2/2004 |
| WO | WO 2005/039630 * | 5/2005 |
| WO | WO 2005/039634 * | 5/2005 |

OTHER PUBLICATIONS

Zwoirek et al, Pharm. Res. 2008, 25/3: 551-562.*
Diwan et al, Curr. Drug Deliv., 2004, 1:405-412.*
Zhang et al, J. Pharm. Sci., 2007, 96/12:3283-3292.*
Wack et al, Vaccine, 2008, 26/4:552-561.*
Kreig, BioDrugs, 1998, 5:341-346.*
Yamamoto et al, Antisense Research and Development, 1994, 4:119-122.*
Agarwal et al, Trends in Mol. Med., 2002, 8:114-121.*
Hartmann et al, J. Immunology, 2000, 164:1617-1624.*
Weiner, J. Leukocyte Biology, 2000, 68:456-463.*
Agarwal et al, Molecular Med. Today, 2000, 6:72-81.*
Zhao et al, Biochemical Pharmacology, 1996, 51:173-182.*
Agrawal, Sudhir et al. (1986). "Efficient Methods for Attaching Non-Radioactive Labels to the 5' ends of Synthetic Oligodeoxyribonucleotides," *Nucleic Acids Res.* 14(15):6227-6245.
Ahmad-Nejad et al. (2002). "Bacterial CpG-DNA and Lipopolysaccharides Activate Activate Toll-like Receptors at Distinct Cellular Compartments," *Eur. J. Immunol.* 32(7):1958-1968.
Ahmeida, E.T.S. Ben et al. (1993). "Immunopotentiation Local and Systemic Humoral Immune Responses by ISCOMs, Liposomes and FCA: Role In Protection Against Influenza A In Mice," *Vaccine* 11:1302-1309.
Aramaki et al. (1995). "Interferon-γ Inductive Effect of Liposomes as an Immunoadjuvant," *Vaccine* 13(18):1809-1814.
Asanuma et al. (1995). "Cross-Protection Against Influenza Virus Infection in Mice Vaccinated by Combined Nasal/Subcutaneous Administration," *Vaccine* 13(1):3-5.
Altmann S. et al. (1995). "NMR Studies of DNA Duplexes Singly Cross-Linked by Different Synthetic Linkers," *Nucleic Acids Research* 23(23):4827-4835.
Atherton et al. (1981). "Synthesis of a 21-Residue Fragment of Human Proinsulin by the Polyamide Solid Phase Method," *Hoppe Seylers Z. Physiol. Chem.* 362:833-839.
Ballas et al. (1996). "Induction of NK Activity in Murine and Human Cells by CpG Motifs in Oligodeoxynulceotides and Bacterial DNA," *J. Immunol.* 157:1840-1845.
Bartley J. P. et al. (1997). "Solution Conformation of an Intramolecular DNA Triplex Containing a Nonnucleotide Linker: Comparison with the DNA Duplex," *Biochemistry* 36:14502-14511.
Beaucage, Serge L. (1993). "Oligodeoxyribonucleotide Synthesis," vol. 20 Chapter 3 in *Protocols for Oligonucleotides and Analogs, Synthesis and Properties*, Sudhir Agrawal, ed., Humana Press, Totowa, NJ: pp. 33-61.
Benoit, Robert et al. (1987). "Peptides. Strategies for Antibody Production and Radioimmunoassays," in *Neuromethods*, Alan A. Boulton et al., eds., Humana Press, Clifton, NJ: pp. 43-72.
Bielinska et al. (1996). "Regulation of In Vitro Gene Expresion Using Antisense Oligonucleotides or Antisense Expression Plasmids Transfected Using Starburst PAMAM Dendrimers," *Nucl. Acid Res.* 24(11):2176-2182.

Bischoff, R. et al. (1987). "Introduction of 5'-Terminal Functional Groups into Synthetic Oligonucleotides for Selective Immobilization," *Analytical Biochemistry* 164:336-344.
Blanks et al. (1988). "An Oligodeoxynucleotide Affinity Column for the Isolation of Sequence Specific DNA Binding Proteins," *Nucleic Acids Res.* 16:10283-10299.
Borel H. and Borel Y. (1990). "A Novel Technique to Link Either Proteins or Peptides to Gammaglobulin to Construct Tolerogens," *Journal of Immunological Methods* 126:159-168.
Borel Y et al. (1995). "Food Allergens Transformed Into Tolerogens," *Int Arch Allergy Immunol* 107:264-267.
Borel Y. et al. (1996). "Parenteral and Oral Administration of Tolerogens: Protein-IgG Conjugates," *Annals of the New York Academy of Sciences* 778:80-87.
Boujrad et al. (1993) "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *Proc. Natl. Acad. Sci. USA* 90:5728-5731.
Bousquet et al. (1999). "Molecular Mechanisms of the Adsorption of a Model Protein (Human Serum Albumin) on Poly(Methylidene Malonate 2.1.2) Nanoparticles," *Pharmaceutical Research* 16(1):141-147.
Braun et al. (1988). "Immunogenic Duplex Nucleic Acids are Nuclease Resistant," *J. Immunol.* 141:2084-2089.
Breiteneder et al. (1989). "The Gene Coding for the Major Birch Pollen Allergen Betv1, is highly homologous to a Pea Disease Resistance Response Gene," *EMBO J.* 8:1935-1938.
Cappaccioli et al. (1993). "Biochemical and Biophysical Research Communication," *Bioch. Biophys Res. Comm.* 197(2):818-825.
Chaturvedi et al. (1996). "Stabilization of Triple-stranded Oligonucleotide Complexes: Use of Probes Containing Alternating Phosphodiester and Stereo-Uniformed Cationic Phosphoramidate Linkages," *Nucleic Acids Res.* 24:2318-2323.
Chavany et al. (1992). "Polyalkylcyanoacrylate Nanoparticles as Polymeric Carriers for Antisense Oligonucleotides," *Pharm. Res.* 9:441-449.
Chavany et al. (1994). "Adsorption of Oligonucleotides onto Polyisohexylcyanoacrylate Nanoparticles Protects Them Against Nucleases and Increases Their Cellular Uptake," *Pharmaceutical Research* 11(9):1370-1378.
Chen et al. (1999). "Enhanced Protection Against a Lethal Influenza Virus Challenge by Immunization With Both Hemagglutinin- and Neuraminydase-expressing DNAs," *Vaccine* 17:653-659.
Cho, Hearn Jay et al. (2000). "Immunostimulatory DNA-Based Vaccines Induce Cytotoxic Lymphocyte Activity by a T-Helper Cell-Independent Mechanism," *Nature Biotechnol.* 18:509-514.
Chua et al. (1988). "Sequence Analysis of cDNA Coding for a Major House Dust Mite Allergen, Der p 1," *J. Exp. Med.* 167:175-182.
Chua et al. (1990). "Expression of Dermatophagoides Pteronyssinus Allergen, Der p II, in *Escherichia coli* and the Binding Studies with Human IgE," *Int. Arch. Allergy Appl. Immunol.* 91:124-129.
Chuang et al. (2002). "Toll-like Receptor 9 Mediates CpG-DNA Signaling," *J. Leukoc. Biol.* 71(3):538-544.
Cload S. T. and Schepartz A. (1991). "Polyether Tethered Oligonucleotide Probes," *J. Am. Chem. Soc.* 113:6324-6326.
Connolly (1987). "The Synthesis of Oligonucleotides Containing a Primary Amino Group at the 5'-Terminus," *Nucleic Acids Res.* 15:3131-3139.
Connolly (1985). "Chemical Synthesis of Oligonucleotides Containing a Free Sulphydryl Group and Subsequent Attachment of Thiol Specific Probes," *Nucleic Acids Res.* 13:4485-4502.
Corey et al. (1987). "Generation of a Hybrid Sequence-Specific Single-Stranded Deoxyribonuclease," *Science* 238:1401-1403.
Coull et al. (1986). "A Novel Method for the Introduction of an Aliphatic Primary Amino Group ath the 5' Terminus of Synthetic Oligonucleotides," *Tetrahedron Lett.* 27(34):3991-3994.
Cowdery et al. (1996). "Bacterial DNA-Induces NK Cell IFN-? to Produce IFN-γ In Vivo and Increases the Toxicity of Lipopolysaccharides," *J. Immunol.* 156:4570-4575.
Cooke et al. (1997). "Allergenic Properties of Ovomucoid in Man," *J. Immunol.* 159:2026-2032.

Czerkinsky et al. (1989). "Oral Administration of a Streptococcal Antigen Coupled to Cholera Toxin B Subunit Evokes Strong Antibody Responses in Salivary Glands and Extramucosal Tissues," *Infect. Immun.* 57(4):1072-1077.

Dagneaux C. et a. (1996). "Parallel and Antiparallel A.A-T Intramolecular Triple Helices," *Nucleic Acids Research* 24(22):4506-4512.

Dauty et al. (2001). "Dimerizable Cationic Detergents with a Low cmc Condense Plasmid DNA into Nanometric Particles and Transfect Cells in Culture," *J. Am. Chem. Soc.* 123(38):9227-9234.

de Martino et al. (1999). "Low IgG3 and high IgG4 subclass levels in children with advanced human immunodeficiency virus-type 1 infection and elevated IgE levels," *Ann. Allergy Asthma Immunol.* 83:160-164.

Dertzbaugh et al. (1993) "Comparative Effectiveness of the Cholera Toxin B Subunit and Alkaline Phosphatase as Carriers for Oral Vaccines," *Infect. Immun* 61(1):48-55.

Deshmukh et al. (2000). "Process Development for Purification of Therapeutic Antisense Oligonuleotide by Anion-Exchange Chromatography," *Organic Process Research & Development* 4: 205-213.

Douglas et al. (1987). "Nanoparticles in drug delivery," *Crit Rev Ther Drug Carrier Syst.* 3(3):233-261.

Dumas et al. (1995). "Induction of Tolerance by Administration of Hapten-Immunoglobulin Conjugates is Associated with Decreased Il-2 and IL-4 Production," *Arch. Dematol. Res.* 287:123-128.

Durand M. et al. (1990). "Circular Dichroism Studies of an Oligodeoxyribonucleotide Containing a Hairpin Loop Made of a Hexaethylene Glycol Chain: Confirmation and Stability," *Nucleic Acids Research* 18(21):6353-6359.

Elsayed et al. (1991). "The Structural Requiements of Epitopes With IgE Binding Capacity Demonstrated by Three Major Allergens From Fish, Egg and Tree Pollen," *Scand. J. Clin. Lab. Invest.* Suppl. 204:17-31.

Fornadley, John (1998). "Allergy Immunotherapy," *Otolaryngol. Clin. North Am.* 31(1):111-127.

Galland, A.V. et al. (1998). "Purification of a 41 kDa Cod-Allergenic Protein," *J. Chromatogr. B.* 706:63-71.

Gao et al. (1995). "Circularization of Oligonucleotides by Disulfide Bridge Formation," *Nucleic Acids Res.* 23(11):2025-2029.

Geoghegan et al. (1992). "Site-Directed Conjugation of Nonpeptide Groups to Peptides and Proteins via Periodate Oxidation of a 2-Amino Alcohol. Application to Modification at N-Terminal Serine," *Bioconjug. Chem.* 3:138-146.

Ginobbi et al. (1997). "Folic Acid-Polylysine Carrier Improves Efficacy of c-myc Antisense Oligodeoxynucleotides on Human Melanoma (M14) Cells," *Anticancer Res.* 17:29-36.

Gnanou Y. et al. (1988). "Synthesis of Star-Shaped Polyethylene Oxide," *Makromol. Chem.* 189:2885-2892.

Godard et al. (1995). "Antisense Effects of Cholesterol-Oligodeoxynucleotide Conjugates Associated with Poly(Alkylcyanoacrylate) Nanoparticles," *Eur. J. Biochem.* 232:404-410.

Gonzalez-Ferreiro et al. (2001). "Characterization of Complexes of an Antisense Oligonucleotide with Protamine and Poly-L-Lysine Salts," *J. Controlled Release* 73:381-390.

Goodchild, John (1990). "Conjugates of Oligonucleotides and Modified Oligonucleotides: A Review of Their Synthesis and Properties," *Bioconjug. Chem.* 1(3):165-187.

Govorkova, E.A. and Smirnov, Yu. A. (1997). "Cross-Protection of Mice Immunized with Different Influenza A (H2) Strains and Challenged with Viruses of the Same HA Subtype," *Acta Virol.* 41:251-257.

Grabarek, Zenon and Gergely, John (1990). "Zero-Length Crosslinking Procedure with the Use of Active Esters," *Anal. Biochem.* 185:131-135.

Granoff et al. (1993). "Effect of Immunity to the Carrier Protein on Antibody Responses to *Haemophilus Influenzae* Type b Conjugate Vaccines," *Vaccine* 11:Suppl.1:S46-S51.

Guy-Caffey et al. (1995). "Novel Polyaminolipids Enhance the Cellular Uptake of Oligonucleotides," *J. Biol. Chem.* 270(52):31391-31396.

Hagiwara et al. (1987). "A New Drug-Delivery-System of Anticancer Agents: Activated Carbon Particles Adsorbing Anticancer Agents," *In Vivo* 1(4):241-252.

Hames, B.D. and Higgins, S.J., eds. (1987). *Transcription and Translation A Practical Approach*, IRL Press: pp. vii-xiv (Table of Contents).

Haralambidis et al. (1990a). "The Synthesis of Polyamide—Oligonucleotide Conjugate Molecules," *Nucleic Acids Res.* 18:493-499.

Haralambidis et al. (1990b). "The Preparation of Polyamide-Oligonucleotide Probes Containing Multiple Non-radioactive Labels," *Nucleic Acids Res.* 18:501-505.

Hendry P. et al. (1994). "Using Linkers to Investigate the Spatial Separation of the Conserved Nucleotides $A^9$ and $G^{12}$ in the Hammerhead Ribozyme," *Biochimica et Biophysica Acta* 1219:405-412.

Inman J. K. (1975). "Thymus-Independent Antigens: The Preparation of Covalent, Hapten-Ficoll Conjugates," *The Journal of Immunology*, 114(2):704-709.

Iyer et al. (1990). "The Automated Synthesis of Sulfur-Containing Oligodeoxyribonucleotides Using 3H-1,2-Benzodithiol-3-one1,1-Dioxide as a Sulfur-Transfer Reagent," *J. Org. Chem.* 55:4693-4699.

Jager et al. (1988). "Oligonucleotide N-Alkylphosphoramidates: Synthesis and Binding to Polynucleotides," *Biochem.* 27:7237-7246.

Jaschke, A. et al. (1993). "Automated Incorporation of Polyethylene Glycol into Synthetic Oligonucleotides," *Tetrahedron Letters*, 34(2):301-304.

Junghans et al. (2000). "Antisense Delivery Using Protamine-Oligonucleotide Particles," *Nucl. Acid Res.* 28(10)e45:i-viii.

Kabanov et al. (1995). "Water Soluble Block Polycations as Carriers for Oligonucleotide Delivery," *Bioconj. Chem.* 6(6):639-643.

Kandimalla E. R. et al. (2001). "Effect of Chemical Modifications of Cytosine and Guanine in a CpG-Motif of Oligonucleotides: Structure-Immunostimulatory Acitvity Relationship," *Bioorganic & Medicinal Chemistry* 9:807-813.

Kessler. (1992). "Nonradioactive Labeling Methods for Nucleic Acids," Chapter 2 in *Nonisotopic DNA Probe Techniques*, Larry J. Kricka, ed., Academic Press, Inc.: pp. 29-92.

Kikuta et al. (1990). "Cross-Protection Against Influenza B Type Virus Infection by Intranasal Inoculation of the HA Vaccines Combined with Cholera Toxin B Subunit," *Vaccine* 8(6):595-599.

Kingetsu et al. (2000). "Common Antigenicity between Japanese Cedar (*Cryptomeria japonica*) Pollen and Japanese Cypress (*Chamaecyparis obtusa*) Pollen, I. H-2 Complex Affects Cross Responsiveness to Cry k 1 and Cha o1 at the T-B-Cell Level in Mice," *Immunology* 99(4):625-629.

Klinman et al. (1997). "Contribution of CpG Motifs to the Immunogenicity of DNA Vaccines," *J. Immunol.* 158:3635-3639.

Kodihalli et al. (1997). "Cross-Protection Among Lethal H5N2 Influenza Viruses Induced by DNA Vaccine to the Hemagglutinin," *J. Virol.* 71:3391-3396.

Kremsky et al. (1987). "Immobilization of DNA via Oligonucleotides Containing an Aldehyde or Carboxylic Acid Group at the 5' Terminus," *Nucleic Acids Res.* 15:2891-2909.

Krieg et al. (1995). "CpG motifs in bacterial DNA trigger direct B-cell activation," *Nature* 374:546-549.

Kullman, Willi. *Enzymatic Peptide Synthesis*, CRC Press, Inc. Boca Raton, FL, Table of Contents, 5 pages.

Latimer et al. (1995). "Specificity of Monoclonal Antibodies Produced Against Phosphorothioate and Ribo Modified DNAs," *Mol. Immunol.* 32:1057-1064.

Lea et al. (1996). "Cloning and Sequencing of cDNA's Encoding the Human Sperm Protein Sp17," *Biochem. Biophys. Acta* 1307:263-266.

Lee et al. (1980). "A Method for Preparing β-hCG COOH Peptide-Carrier Conjugates of Predictable Composition," *Mol. Imm.* 17:749-756.

Legendre et al. (1993). "Cyclic Amphipathic Peptide-DNA Complexes Mediate High-Efficiency Transfection of Adherent Mammalian Cells," *Proc. Natl. Acad. Sci USA* 90:893-897.

Li, ed. (1992). "Chapter 5: Electrolyte Systems," *Capillary electrophoresis, Principles, Practice and Application, Journal of Chromatography*, vol. 52, Elsevier Science Publishers, Amsterdam, The Netherlands, pp. 202-206.

Lipford et al. (1997a). "CpG-Containing Synthetic Oligonucleotides Promote B and Cytotoxic T Cell Responses to Protein Antigen: A New Class of Vaccine Adjuvants," *Eur. J. Immunol.* 27:2340-2344.

Ma M. Y.-X. aet al. (1993). "Design and Synthesis of RNA Miniduplexes Via a Synthetic Linker Approach. 2. Generation of Covalently Closed, Double-Stragded Cyclic HIV-1 TAR RNA Analogs with High Tat-Binding Affinity," *Nucleic Acids Research* 21(11):2585-2589.

Ma M. Y.-X. et al. (1993). "Design and Synthesis of RNA Miniduplexes via a Synthetic Linker Approach," *Biochemistry* 32:1751-1758.

Matteucci, Mark (1997). "Oligonucleotide analogues: an overview," *Oligonucleotides As Therapeutic Agents*, D.J. Chadwick and G. Cardew, eds., John Wiley and Sons, New York, NY:CIBA Foundation Symposium, pp. 5-18.

Maurer et al.(2001). "Spontaneous Entrapment of Polynucleotides Upon Electrostatic Interaction with Ethanol-Destabilized Cationic Liposomes," *Biophys. J.* 80:2310-2326.

Mbawuike et al. (1994). "Influenza A Subtype Cross-Protection After Immunization of Outbred Mice with a Purified Chimeric NS1/HA2 Influenza Virus Protein," *Vaccine* 12:1340-1348.

McCurdy et al. (1991). "Deoxyoligonucleotides with Inverted Polarity: synthesis and Use in Triple-Helix Formation," *Nucleosides & Nucleotides* 10(1-3):287-290.

Meyer et al. (1998). "Cationic Liposomes Coated with Polyethylene Glycol As Carriers for Oligonucleotides," *J. Biol. Chem.* 273(25):15621-15627.

Miller et al. (1971). "Synthesis and Properties of Adenine and Thymidine Nucleoside Alkyl Phosphotriesters, the Neutral Analogs of Dinucleoside Monophosphates," *JACS* 93:6657-6665.

Mitragotri et al. (1995). "Ultrasound-Mediated Transdermal Protein Delivery," *Science* 269:850-853.

Nashar et al.(1993) "Current Progress in the Development of the B Subunits of Cholera Toxin and *Eshcericia coli* Heat-Labile Enterotoxin as Carriers for the Oral Delivery of Heterologous Antigens and Epitopes," *Vaccine* 11: 235-240.

Nelson et al. (1996). "Incorporation of a Non-Nucleotide Bridge into Hairpin Oligonucleotides Capable of High-Affinity Binding to the Rev Protein of HIV-1," *Biochemistry* 35:5339-5344.

Nelson et al. (1997). "N3'→P5' Oligodeoxyribonucleotide Phosphoramidates: A New Method of Synthesis Based on a Phosphoramidite Amino-Exchange Reaction," *J. Org. Chem.* 62:7278-7287.

Nelson et al. (1989). "Bifunctional Oligonucleotide Probes Synthesized Using a Novel CPG Support Are Able to Detect Single Base Pair Mutations," *Nucleic Acids Research* 17(18):7187-7194.

O'Shannessy et al. (1985). "Specific Conjugation Reactions of the Oligosaccharide Moieties of Immunoglobulins," *J. Applied Biochem.* 7:347-355.

Ono A. et al. (1991). DNA Triplex Formation of Oligonucleotied Analogues Consisting of Linker Groups an dOctamer Segments That Have Opposite Sugar-Phosphate ackbone Polarities, *Biochemistry* 30:9914-9921.

Pastorello, Elide A. et al. (1998). "Sensitization to the Major Allergen of Brazil Nut is Correlated with the Clinical Expression of Allergy," *J. Allergy Clin. Immunol.* 102(6):1021-1027.

Pertmer et al. (1996). "Influenza Virus Nucleoprotein-Specific Immunoglobulin G Subclass and Cytokine Responses Elicited by DNA Vaccination are Dependent on the Route of Vector DNA Delivery," *J. Virol.* 70:6119-6125.

Peyrottes et al. (1996). "Oligodeoxynucleoside Phosphoramidates (P-NH²): Synthesis and Thermal Stability of Duplexes with DNA and RNA Targets," *Nucleic Acids Res.* 24:1841-1848.

Pisetsky (1996a). "The Immunologic Properties of DNA," *J. Immunol.* 156:421-423.

Rafnar et al. (1991). "Cloning of Amb a I (Antigen E), the Major Allergen Family of Short Ragweed Pollen," *J. Biol. Chem.* 266:1229-1236.

Raz et al. (1994). "Intradermal Gene Immunization: The Possible Role of DNA Uptake in the Induction of Cellular Immunity to Viruses," *Proc. Natl. Acad. Sci. USA* 91:9519-9523.

Raz et al. (1996). "Preferential induction of a $Th_1$ immune response and inhibition of specific IgE antibody formation by plasmid DNA immunization," *Proc. Natl. Acad. Sci. USA* 93:5141-5145.

Reese, Gerald et al. (1997). "Characterization of Recombinant Shrimp Allergen Pen a 1 (Tropomyosin)," *Int. Arch. Allergy Immunol.* 113:240-242.

Rein et al. (1993). "New Developments in Synthesis of Star Polymers with Poly(Ethylene Oxide) Arms," *Acta Polymer.* 44:225-229.

Reynolds M.A. et al. (1996). "Antisense Oligonucleotides Containing an Intermal, Non-Nucleotide-Based Linker Promote Site-Specific Cleavage of RNA," *Nucleic Acids Research* 24(4):760-765.

Richardson P. L. and Schepartz A. (1991). "Tethered Oligonucleotide Probes. A Strategy for the Recognition of Structured RNA," *J. Am. Chem. Soc.* 113:5109-5111.

Rogers et al. (1993). "Recombinant Fel d I: Expression, Purification, IgE Binding and Reaction with Cat-Allergic Human T Cells," *Mol. Immunol.* 30:559-568.

Roget et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17:7643-7651.

Romagnani, Sergio (2000). "T-Cell Subsets (Th1 versus Th2)," *Ann. Allergy Asthma Immunol.* 85(1):9-18.

Roman et al., (1997) ."Immunostimulatory DNA sequences function as T helper-1-promoting adjuvants" *Nature Medicine* 3:849-854.

Ruth. (1984). "Chemical Synthesis of Non-Radioactively-Labeled DNA Hybridization Probes," *4th Annual Congress for Recombinant DNA Research* 3(1):123.

Ruth (1991). "Chapter 11: Oligodeoxynucleotides with Reporter Groups Attached to the Base," in *Oligonucleotides and Analogues: A Practical Approach*, IRL Press, pp. 255-282.

Salunkhe M. et al. (1992). "Control of Folding and Binding of Oligonucleotieds by Use of Nonnucleotide Linker," *J. Am. Chem. Soc.* 114:8768-8772.

Sato et al., (1996). "Immunostimulatory DNA Sequences Necessary for Effective Intradermal Gene Immunization," *Science* 273:352-354.

Scherle and Gerhard (1986). "Differential Ability of B Cells Specific for External vs. Internal Influenza Virus Proteins to Respond to Help from Influenza Virus-Specific T-cell clones in vivo," *Proc. Natl. Acad. Sci. USA* 85:4446-4450.

Scherle and Gerhard (1988). "Functional Analysis of Influenza-Specific Helper T Cell Clones In Vivo," *PJ. Exp. Med.* 164:1114-1128.

Schultz et al. (1996). "Oligo-2'-fluoro-2'-deoxynucleotide N3'-P5' Phosphoramidates: Synthesis and Properties," *Nucleic Acids Res.* 24:2966-2973.

Sélo, I. et al. (1999). "Allergy to Bovine β-Lactoglobulin: Specificity of Human IgE to Tryptic Peptides," *Clin. Exp. Allergy* 29:1055-1063.

Semple et al. (2001). "Efficient Encapsulation of Antisense Oligonucleotides in Lipid Vesicles Using Ionizable Aminolipids: Formation of Novel Small Multilamellar Vesicle Structures," *Bioch. Biophys. Acta* 1510:152-166.

Shi et al. (2001). "Efficient Cationic Lipid—Mediated Delivery of Antisense Oligonucleotides into Eurkaryotic Cells: Down-Regulation of the Corticotropin-Releasing Factor Receptor," *Nucl. Acid Res.* 29(10):2079-2087.

Shimada et al. (1986). "In Vivo Augmentation of Natural Killer Cell Activity with a Deoxyribonucleic Acid Fraction of BCG," *Jpn. J. Cancer Res.* 77:808-816.

Sinha, Nanda D. and Striepeke, Steve (1991). "Oligonucleotides with Reporter Groups Attached to the 5'-Terminus," Chapter 8 in *Oligonucleotide Analogues: A Practical Approach*, F. Eckstein, ed., IRL Press: pp. 185-210.

Sowka, Slawomir et al. (1998). "cDNA Cloning of the 43-kDa Latex Allergen Hev b 7 with Sequence Similarity to Patatins and its Expression in the Yeast *Pichia pastoris*," *Eur. J Biochem.* 255:213-219.

Stanley, J.S. et al. (1996). "Chapter 28: Peanut Hypersensitivity: IgE Binding Characteristics of a Recombinant *Ara h* 1 Protein," *News Horizons in Allergy Immuno-Therapy.* 409:213-216.

Staros et al., (1986) "Enhancement by N-Hydroxysulfosucciniminde of Water-Soluble Carbodiimide-Mediated Coupling Reactions," *Analytical Biochemistry* 156:220-222.

Stewart et al. (1996). "Enhanced Biological Activity of Antisense Oligonucleotides Complexed with Glycosylated Poly-L-Lysine," *Mol. Pharmacol.* 50(6):1487-1494.

Stirchak et al. (1989). "Uncharged Stereoregular Nucleic Acid Analogs: 2. Morpholinoi Nucleoside Oligomers with Carbamate Internucleoside Linkages," *Nucleic Acids Res.* 17:6129-6141.

Takahashi et al. (1990). "Induction of CD8+ cytotoxic T Cells by Immunization with Purified HIV-1 Envelope Protein in ISCOMs," *Nature* 344:873-875.

Tamborini, Elena et al. (1997). Biochemical and Immunological Characterization of Recombinant Allergen Lol p. 1, *Eur. J. Biochem.* 249:886-894.

Tamura et al. (1992). "Superior Cross-Protective Effect of Nasal Vaccination to Subcutaneous Inoculation with Influenza Hemagglutinin Vaccine," *Eur. J. Immunol.* 22:477-481.

Tamura et al. (1994). "Formulation of Inactivated Influenza Vaccines for Providing Effective Cross-Protection by Intranasal Vaccination in Mice," *Vaccine* 12:310-316.

Tang et al. (2000) "Large Scale Synthesis of Oligonucleotide Phosphorothioates Using 3-Amino-1,2,4-Dithiazole-5-Thione as an Efficient Sulfur-Transfer Reagent," *Org. Process Res. Dev.* 4:194-198.

Tomalia et al. (1990). "Starburst Dendrimers: Molecular-Level Control of Size, Shape, Surface Chemistry, Topology, and Flexibility from Atoms to Macroscopic Matter," *Angew. Chem. Int. Ed. Engl.* 29:138-175.

Teuber et al. (1998). "Cloning and Sequencing of a Gene Encoding a 2S Albumin Seed Storage Protein Precursor From English Walnut (*Juglans regia*), a Major Food Allergen," *J Allergy Clin Immunol.* 101(6 Pt 1):807-814.

Van Do, T. et al. (1999). "Expression and Analysis of Recombinant Salmon Parvalbumin, the Major Allergen in Atlantic Salmon (*Salmo salar*)," *Scand. J. Immunol.* 50:619-625.

Wang et al. (1994). "Circular RNA Oligonucleotides. Synthesis, Nucleic Acid Binding Properties, and a Comparison with Circular DNAs," *Nucleic Acids Res.* 22:2326-2333.

Warner et al. (1984). "Construction and Evaluation of an Instrument for the Automated Synthesis of Oligodeoxyribonucleosides," *DNA* 3:401-411.

Widhe et al., (1998). "IgG Subclasses in Lyme Borreliosis: A Study of Specific IgG Subclass Distribution in a Interferon-y-Predominated Disease," *Scand. J. Immunol* 47: 575-581.

Wolff. (1997). "Naked DNA transport and expression in mammalian cells," *Neuromuscul Disord.* 7(5):314-318.

Wyman et al. (1997). "Design, Synthesis, and Characterization of a Cationic Peptide That Binds to Nucleic Acids and Permeabilizes Bilayers,"*Biochemistry* 36(10):3008-3017.

Wyrzykiewica et al. (1994). "Efficiency of Sulfurization in the Synthesis of Oligodeoxyribonucleotide Phosphorothioates Utilizing Various Sulfurizing Reagents," *Bioorg. & Med. Chem. Lett.* 4(12):1519-1522.

Yamamoto, Saburo et al. (1992). "Unique Palindromic Sequences in Synthetic Oligonucleotides are Required to Induce IFN and Augment IFN-Mediated Natural Killer Activity," *J. Immunol.* 148(12):4072-4076.

Yanagawa et al. (1988). "Analysis of Superhelical Structures of Nucleic Acid-Lipid Conjugates by Image Processing," *Nucleic Acids Symp. Ser.* 19:189-192.

Yoo et al. (1999). "PAMAM dendrimers as delivery agents for antisense oligonucleotides," *Pharm Res.* 16(12):1799-1804.

Zon, Gerald, (1993)."Chapter 8: Oligonucleoside phosphorothioates," *Protocols for Oligonucleotides and Analogs, Synthesis and Properties*, Agrawal, S. (ed.), Humana Press, pp. 165-189.

Zuckermann et al. (1987). "Efficient Methods for Attachment of Thiol Specific Probes to the 3'-Ends of Synthetic Oligodeoxyribonucleotides," *Nucleic Acids Res.* 15:5305-5321.

Hunter et al., Am. J. Obstet. Gynecol. (2001) 185:1174-1179.

International Search Report for PCT/US03/25415, mailed on May 11, 2004, 4 pages.

O'Hagan, Current Drug Targets—Infectious Disorders (2001) 1:273-286.

Singh and O'Hagan, Pharmaceutical Research (2002) 19(6):715-728.

Singh and Srivastava, Current HIV Research (2003) 1:309-320.

Singh et al., Pharmaceutical Research (2001) 18(10):1476-1479.

Rojas, J. et al. (Jun. 10, 1999). "Optimization of the Encapsulation and Release of β-lactoglobulin Entrapped Poly(DL-lactide-co-glycolide) Microspheres," *Int. J. Pharm.* 183(1):67-71.

Hafner, M. et al. (Jul. 15, 2001, e-pub. Jul. 1, 2001). "Antimetastatic Effect of CpG DNA Mediated by Type I IFN," *Cancer Research* 61:5523-5528.

Davis, H.L. et al. (1998). "CpG DNA is a Potent Enhancer of Specific Immunity in Mice Immunized with Recombinant Hepatitis B Surface Antigen," *Journal of Immunology* 160:870-876.

Gregoriadis, G. (Mar. 1990). "Immunological Adjuvants: A Role for Liposomes," *Immunology Today* 11(3):89-97.

Mccluskie, M.J. et al. (2001). "Mucosal Immunization of Mice Using CpG DNA and/or Mutants of the Heat-labile Enterotoxin of *Escherichia coli* as Adjuvants," *Vaccine* 19:3759-3768.

Raz, E. et al. (1996). "Potential Role of Immunostimulatory DNA Sequences (ISS) in Genetic Immunization and Autoimmunity," presented at *ACR Poster Session C, Cytokines and Inflammatory Mediators*, Sunday, Oct. 20, 1996, *Arthritis & Rheumatism*39(9), abstract no. 615.

Supplementary European Search Report mailed on Sep. 2, 2010, for EP Patent Application No. 03785275.3, filed on Aug. 12, 2003, 3 pages.

\* cited by examiner

SEQUENCE LISTING

```
<160> NUMBER OF SEQ ID NOS: 62

<210> SEQ ID NO 1
<211> LENGTH: 22
<212> TYPE: DNA
<213> ORGANISM: Artificial Sequence
<220> FEATURE:
<223> OTHER INFORMATION: IMC polynucleotide

<400> SEQUENCE: 1
tgactgtgaa cgttcgagat ga                                          22

<210> SEQ ID NO 2
<211> LENGTH: 22
<212> TYPE: DNA
<213> ORGANISM: Artificial Sequence
<220> FEATURE:
<223> OTHER INFORMATION: IMC polynucleotide

<400> SEQUENCE: 2
tgaccgtgaa cgttcgagat ga                                          22

<210> SEQ ID NO 3
<211> LENGTH: 23
<212> TYPE: DNA
<213> ORGANISM: Artificial Sequence
<220> FEATURE:
<223> OTHER INFORMATION: IMC polynucleotide
```

```
<400> SEQUENCE: 3
tcatctcgaa cgttccacag tca                                             23

<210> SEQ ID NO 4
<211> LENGTH: 22
<212> TYPE: DNA
<213> ORGANISM: Artificial Sequence
<220> FEATURE:
<223> OTHER INFORMATION: IMC polynucleotide

<400> SEQUENCE: 4
tgactgtgaa cgttccagat ga                                              22

<210> SEQ ID NO 5
<211> LENGTH: 26
<212> TYPE: DNA
<213> ORGANISM: Artificial Sequence
<220> FEATURE:
<223> OTHER INFORMATION: IMC polynucleotide

<400> SEQUENCE: 5
tccataacgt tcgcctaacg ttcgtc                                          26

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: n = 5-bromocytosine

<400> SEQUENCE: 6
tgactgtgaa ngttccagat ga                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: n = 5-bromocytosine

<400> SEQUENCE: 7
tgactgtgaa ngttcgagat ga                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: n = 5-bromocytosine

<400> SEQUENCE: 8
tgactgtgaa ngttbgagat ga                                              22

<210> SEQ ID NO 9
<211> LENGTH: 10
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: n = 5-bromocytosine

<400> SEQUENCE: 9 gaaangutcg                                                                 10

<210> SEQ ID NO 10
<211> LENGTH: 10
<212> TYPE: DNA
<213> ORGANISM: Artificial Sequence
<220> FEATURE:
<223> OTHER INFORMATION: IMC polynucleotide
<220> FEATURE:
<221> NAME/KEY: VARIANT
<222> LOCATION: 1,5
<223> OTHER INFORMATION: n = 5-bromocytosine

<400> SEQUENCE: 10 ngaangutcg                                                                 10

<210> SEQ ID NO 11
<211> LENGTH: 11
<212> TYPE: DNA
<213> ORGANISM: Artificial Sequence
<220> FEATURE:
<223> OTHER INFORMATION: IMC polynucleotide

<400> SEQUENCE: 11
tcgagcgttc t                                                               11

<210> SEQ ID NO 12
<211> LENGTH: 10
<212> TYPE: DNA
<213> ORGANISM: Artificial Sequence
<220> FEATURE:
<223> OTHER INFORMATION: IMC polynucleotide

<400> SEQUENCE: 12
tgaacgutcg                                                                 10

<210> SEQ ID NO 13
<211> LENGTH: 10
<212> TYPE: DNA
<213> ORGANISM: Artificial Sequence
<220> FEATURE:
<223> OTHER INFORMATION: IMC polynucleotide

<400> SEQUENCE: 13
gaaccgttcg                                                                 10

<210> SEQ ID NO 14
<211> LENGTH: 10
<212> TYPE: DNA
<213> ORGANISM: Artificial Sequence
<220> FEATURE:
<223> OTHER INFORMATION: IMC polynucleotide

<400> SEQUENCE: 14
cgaacgttcg                                                                 10

<210> SEQ ID NO 15
```

```
<211> LENGTH: 20
<212> TYPE: DNA
<213> ORGANISM: Artificial Sequence
<220> FEATURE:
<223> OTHER INFORMATION: IMC polynucleotide

<400> SEQUENCE: 15
atcgactctc gagcgttctc                                              20

<210> SEQ ID NO 16
<211> LENGTH: 24
<212> TYPE: DNA
<213> ORGANISM: Artificial Sequence
<220> FEATURE:
<223> OTHER INFORMATION: IMC polynucleotide

<400> SEQUENCE: 16
tcgtcgtttt gtcgttttgt cgtt                                         24

<210> SEQ ID NO 17
<211> LENGTH: 16
<212> TYPE: DNA
<213> ORGANISM: Artificial Sequence
<220> FEATURE:
<223> OTHER INFORMATION: IMC polynucleotide

<400> SEQUENCE: 17
tcgtcgaacg ttcgtt                                                  16

<210> SEQ ID NO 18
<211> LENGTH: 14
<212> TYPE: DNA
<213> ORGANISM: Artificial Sequence
<220> FEATURE:
<223> OTHER INFORMATION: IMC polynucleotide

<400> SEQUENCE: 18
tcgtcgaacg ttcg                                                    14

<210> SEQ ID NO 19
<211> LENGTH: 12
<212> TYPE: DNA
<213> ORGANISM: Artificial Sequence
<220> FEATURE:
<223> OTHER INFORMATION: IMC polynucleotide

<400> SEQUENCE: 19
tcgtcgaacg tt                                                      12

<210> SEQ ID NO 20
<211> LENGTH: 10
<212> TYPE: DNA
<213> ORGANISM: Artificial Sequence
<220> FEATURE:
<223> OTHER INFORMATION: IMC polynucleotide

<400> SEQUENCE: 20
tcgaacgttc                                                         10

<210> SEQ ID NO 21
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
```

```
<222> LOCATION: 1
<223> OTHER INFORMATION: n = t, g, c, or 5-bromocytosine
<220> FEATURE:
<221> NAME/KEY: VARIANT
<222> LOCATION: 2
<223> OTHER INFORMATION: n = t, g, a or u
<220> FEATURE:
<221> NAME/KEY: VARIANT
<222> LOCATION: 4
<223> OTHER INFORMATION: n = t, a or c
<220> FEATURE:
<221> NAME/KEY: VARIANT
<222> LOCATION: 7
<223> OTHER INFORMATION: n = t, g or u

<400> SEQUENCE: 21 nnancgntcg                                                                10

<210> SEQ ID NO 22
<211> LENGTH: 10
<212> TYPE: DNA
<213> ORGANISM: Artificial Sequence
<220> FEATURE:
<223> OTHER INFORMATION: Immunomodulatory polynucleotide

<400> SEQUENCE: 22
tgaacgttcg                                                                10

<210> SEQ ID NO 23
<211> LENGTH: 10
<212> TYPE: DNA
<213> ORGANISM: Artificial Sequence
<220> FEATURE:
<223> OTHER INFORMATION: Immunomodulatory polynucleotide

<400> SEQUENCE: 23
ggaacgttcg                                                                10

<210> SEQ ID NO 24
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: n = t, g, c, or 5-bromocytosine
<220> FEATURE:
<221> NAME/KEY: VARIANT
<222> LOCATION: 2
<223> OTHER INFORMATION: n = t, g, a or u
<220> FEATURE:
<221> NAME/KEY: VARIANT
<222> LOCATION: 4
<223> OTHER INFORMATION: n = t, a or c
<220> FEATURE:
<221> NAME/KEY: VARIANT
<222> LOCATION: 5
<223> OTHER INFORMATION: n = 5-bromocytosine
<220> FEATURE:
<221> NAME/KEY: VARIANT
<222> LOCATION: 7
<223> OTHER INFORMATION: n = t, g or u

<400> SEQUENCE: 24 nnanngntcg                                                                10

<210> SEQ ID NO 25
<211> LENGTH: 10
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: n = 5-bromocytosine

<400> SEQUENCE: 25 tgaangttcg                                                             10

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct that is a control DNA
      sequence

<400> SEQUENCE: 26
tgactgtgaa ccttagagat ga                                               22

<210> SEQ ID NO 27
<211> LENGTH: 24
<212> TYPE: DNA
<213> ORGANISM: Artificial Sequence
<220> FEATURE:
<223> OTHER INFORMATION: Immunomodulatory polynucleotide

<400> SEQUENCE: 27
tcgtcgaacg ttcgttaacg ttcg                                             24

<210> SEQ ID NO 28
<211> LENGTH: 22
<212> TYPE: DNA
<213> ORGANISM: Artificial Sequence
<220> FEATURE:
<223> OTHER INFORMATION: Immunomodulatory polynucleotide

<400> SEQUENCE: 28
tcgtcgtgaa cgttcgagat ga                                               22

<210> SEQ ID NO 29
<211> LENGTH: 22
<212> TYPE: DNA
<213> ORGANISM: Artificial Sequence
<220> FEATURE:
<223> OTHER INFORMATION: Immunomodulatory polynucleotide

<400> SEQUENCE: 29
tcgtcggtat cggtcggtat ga                                               22

<210> SEQ ID NO 30
<211> LENGTH: 22
<212> TYPE: DNA
<213> ORGANISM: Artificial Sequence
<220> FEATURE:
<223> OTHER INFORMATION: Immunomodulatory polynucleotide

<400> SEQUENCE: 30
tcgtcggaac cgttcggaat ga                                               22

<210> SEQ ID NO 31
<211> LENGTH: 19
<212> TYPE: DNA
<213> ORGANISM: Artificial Sequence
<220> FEATURE:
```

<223> OTHER INFORMATION: Immunomodulatory polynucleotide

<400> SEQUENCE: 31
tcgtcgaacg ttcgagatg                                                     19

<210> SEQ ID NO 32
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: n = 5-bromocytosine

<400> SEQUENCE: 32
tcgtngaacg ttcgagatg                                                     19

<210> SEQ ID NO 33
<211> LENGTH: 22
<212> TYPE: DNA
<213> ORGANISM: Artificial Sequence
<220> FEATURE:
<223> OTHER INFORMATION: Synthetic Construct
<220> FEATURE:
<223> OTHER INFORMATION: Immunomodulatory polynucleotide

<400> SEQUENCE: 33
ttcgaacgtt cgttaacgtt cg                                                 22

<210> SEQ ID NO 34
<211> LENGTH: 22
<212> TYPE: DNA
<213> ORGANISM: Artificial Sequence
<220> FEATURE:
<223> OTHER INFORMATION: Immunomodulatory polynucleotide
<220> FEATURE:
<221> NAME/KEY: VARIANT
<222> LOCATION: 11
<223> OTHER INFORMATION: n = 5-bromocytosine

<400> SEQUENCE: 34
tcgtcggaaa ngutcggaat ga                                                 22

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5, 9
<223> OTHER INFORMATION: n = 5-bromocytosine

<400> SEQUENCE: 35
tcgtngaang utcggaatga                                                    20

<210> SEQ ID NO 36
<211> LENGTH: 22
<212> TYPE: DNA
<213> ORGANISM: Artificial Sequence
<220> FEATURE:
<223> OTHER INFORMATION: Immunomodulatory polynucleotide
<220> FEATURE:
<221> NAME/KEY: VARIANT
<222> LOCATION: 5
<223> OTHER INFORMATION: n = 5-bromocytosine

```
<400> SEQUENCE: 36
tcgtngtgaa cgttcgagat ga                                              22

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct
<220> FEATURE:
<223> OTHER INFORMATION: IMC polynucleotide

<400> SEQUENCE: 37
ggtgcatcga tgcagggggg                                                 20

<210> SEQ ID NO 38
<211> LENGTH: 20
<212> TYPE: DNA
<213> ORGANISM: Artificial Sequence
<220> FEATURE:
<223> OTHER INFORMATION: ISS oligonucleotide

<400> SEQUENCE: 38
tgcttgcaag cttgcaagca                                                 20

<210> SEQ ID NO 39
<211> LENGTH: 21
<212> TYPE: DNA
<213> ORGANISM: Artificial Sequence
<220> FEATURE:
<223> OTHER INFORMATION: IMC polynucleotide

<400> SEQUENCE: 39
tcgtcgaacg ttcgagatga t                                               21

<210> SEQ ID NO 40
<211> LENGTH: 22
<212> TYPE: DNA
<213> ORGANISM: Artificial Sequence
<220> FEATURE:
<223> OTHER INFORMATION: IMC polynucleotide

<400> SEQUENCE: 40
tgactgtgaa cgttcgagat ga                                              22

<210> SEQ ID NO 41
<211> LENGTH: 12
<212> TYPE: PRT
<213> ORGANISM: Artificial Sequence
<220> FEATURE:
<223> OTHER INFORMATION: CTL peptide

<400> SEQUENCE: 41

Ile Pro Gln Ser Leu Asp Ser Trp Trp Thr Ser Leu
 1               5                  10

<210> SEQ ID NO 42
<211> LENGTH: 9
<212> TYPE: PRT
<213> ORGANISM: Artificial Sequence
<220> FEATURE:
<223> OTHER INFORMATION: Membrane disrupting peptide

<400> SEQUENCE: 42

Lys Phe Phe Lys Phe Phe Lys Phe Phe
```

```
                       1               5
```

<210> SEQ ID NO 43
<211> LENGTH: 30
<212> TYPE: PRT
<213> ORGANISM: Artificial Sequence
<220> FEATURE:
<223> OTHER INFORMATION: Acylated peptide

<400> SEQUENCE: 43

Trp Glu Ala Lys Leu Ala Lys Ala Leu Ala Lys Ala Leu Ala Lys His
 1               5                  10                  15

Leu Ala Lys Ala Leu Ala Lys Ala Leu Glu Ala Cys Glu Ala
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Membrane disrupting peptide

<400> SEQUENCE: 44

Trp Glu Ala Lys Leu Ala Lys Ala Leu Ala Lys Ala Leu Ala Lys His
 1               5                  10                  15

Leu Ala Lys Ala Leu Ala Lys Ala Leu Lys Ala Cys Glu Ala
            20                  25                  30

<210> SEQ ID NO 45
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14
<223> OTHER INFORMATION: Nucleotide at position 14 has a hydroxyl group

<400> SEQUENCE: 45
tcgtcgatcg tcga                                                    14

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14
<223> OTHER INFORMATION: Nucleotide at position 14 has a phosphate group

<400> SEQUENCE: 46
tcgtcgatcg tcga                                                    14

<210> SEQ ID NO 47
<211> LENGTH: 14

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14
<223> OTHER INFORMATION: Nucleotide at position 14 has a 3'
      hexaethyleneglycol linker moiety

<400> SEQUENCE: 47
tcgtcgatcg tcga                                                           14

<210> SEQ ID NO 48
<211> LENGTH: 14
<212> TYPE: DNA
<213> ORGANISM: Artificial Sequence
<220> FEATURE:
<221> NAME/KEY: misc_feature
<222> LOCATION: 1
<223> OTHER INFORMATION: Nucleotide at position 1 has a 5'
      hexaethyleneglycol linker moiety
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14
<223> OTHER INFORMATION: Nucleotide at position 14 has a 3'
      hexaethyleneglycol linker moiety
<220> FEATURE:
<223> OTHER INFORMATION: Synthetic Construct

<400> SEQUENCE: 48
tcgtcgatcg tcga                                                           14

<210> SEQ ID NO 49
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a hexaethyleneglycol linker moiety
<220> FEATURE:
<223> OTHER INFORMATION: Synthetic Construct

<400> SEQUENCE: 49
tcgtcgatcg tcgatcgtcg a                                                   21

<210> SEQ ID NO 50
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
```

```
<221> NAME/KEY: misc_feature
<222> LOCATION: 14,15
<223> OTHER INFORMATION: Nucleotides at positions 14 and 15 are linked
      by four hexaethyleneglycol linker moieties
<220> FEATURE:
<223> OTHER INFORMATION: Synthetic Construct

<400> SEQUENCE: 50
tcgtcgatcg tcgatcgtcg a                                              21

<210> SEQ ID NO 51
<211> LENGTH: 28
<212> TYPE: DNA
<213> ORGANISM: Artificial Sequence
<220> FEATURE:
<221> NAME/KEY: misc_feature
<222> LOCATION: 14,15
<223> OTHER INFORMATION: Nucleotides at positions 14 and 15 are linked
      by a glycerol linker moiety
<220> FEATURE:
<221> NAME/KEY: misc_feature
<222> LOCATION: 21,22
<223> OTHER INFORMATION: Nucleotides at positions 21 and 22 are linked
      by a hexaethyleneglycol linker moiety
<220> FEATURE:
<223> OTHER INFORMATION: Synthetic Construct

<400> SEQUENCE: 51
tcgtcgatcg tcgatcgtcg atcgtcga                                       28

<210> SEQ ID NO 52
<211> LENGTH: 14
<212> TYPE: DNA
<213> ORGANISM: Artificial Sequence
<220> FEATURE:
<221> NAME/KEY: misc_feature
<222> LOCATION: 1
<223> OTHER INFORMATION: Nucleotide at position 1 has a phosphate group
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<223> OTHER INFORMATION: Synthetic Construct

<400> SEQUENCE: 52
tcgtcgatcg tcga                                                      14

<210> SEQ ID NO 53
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a linker that includes a hexaethyleneglycol linker
      moiety, a glycerol linker moiety, and a
      hexaethyleneglycol linker moiety
<220> FEATURE:
<223> OTHER INFORMATION: Synthetic Construct

<400> SEQUENCE: 53
tcgtcgatcg tcgatcgtcg a                                              21
```

```
<210> SEQ ID NO 54
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a hexaethyleneglycol linker moiety
<220> FEATURE:
<223> OTHER INFORMATION: Synthetic Construct

<400> SEQUENCE: 54
tcgtcgaacg ttcgagatga t                                              21

<210> SEQ ID NO 55
<211> LENGTH: 19
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a hexaethyleneglycol linker moiety
<220> FEATURE:
<223> OTHER INFORMATION: Synthetic Construct

<400> SEQUENCE: 55
tcgtcgaacg ttagatgat                                                 19

<210> SEQ ID NO 56
<211> LENGTH: 22
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a C3 linker moiety
<220> FEATURE:
<221> NAME/KEY: misc_feature
<222> LOCATION: 14,15
<223> OTHER INFORMATION: Nucleotides at positions 14 and 15 are linked
      by a C3 linker moiety
<220> FEATURE:
<223> OTHER INFORMATION: Synthetic Construct

<400> SEQUENCE: 56
tcgtcgaacg ttcgagatcg at                                             22

<210> SEQ ID NO 57
<211> LENGTH: 21
<212> TYPE: DNA
<213> ORGANISM: Artificial Sequence
<220> FEATURE:
<221> NAME/KEY: misc_feature
<222> LOCATION: 14,15
<223> OTHER INFORMATION: Nucleotides at positions 14 and 15 are linked
      by a glycerol linker moiety
<220> FEATURE:
<223> OTHER INFORMATION: Synthetic Construct

<400> SEQUENCE: 57
```
tcgtcgatcg tcgatcgtcg a          21

<210> SEQ ID NO 58
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a linker that includes a hexaethyleneglycol linker
      moiety and a glycerol linker moiety
<220> FEATURE:
<223> OTHER INFORMATION: Synthetic Construct

<400> SEQUENCE: 58
tcgtcgatcg tcgatcgtcg a          21

<210> SEQ ID NO 59
<211> LENGTH: 35
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 21,22
<223> OTHER INFORMATION: Nucleotides at positions 21 and 22 are linked
      by a hexaethyleneglycol linker moiety
<220> FEATURE:
<221> NAME/KEY: misc_feature
<222> LOCATION: 28,29
<223> OTHER INFORMATION: Nucleotides at positions 28 and 29 are linked
      by a glycerol linker moiety
<220> FEATURE:
<223> OTHER INFORMATION: Synthetic Construct

<400> SEQUENCE: 59
tcgtcgatcg tcgatcgtcg atcgtcgatc gtcga          35

<210> SEQ ID NO 60
<211> LENGTH: 49
<212> TYPE: DNA
<213> ORGANISM: Artificial Sequence
<220> FEATURE:
<221> NAME/KEY: misc_feature
<222> LOCATION: 14,15
<223> OTHER INFORMATION: Nucleotides at positions 14 and 15 are linked
      by a glycerol linker moiety
<220> FEATURE:
<221> NAME/KEY: misc_feature
<222> LOCATION: 35,36
<223> OTHER INFORMATION: Nucleotides at positions 35 and 36 are linked
      by a glycerol linker moiety
<220> FEATURE:
<221> NAME/KEY: misc_feature
<222> LOCATION: 42,43
<223> OTHER INFORMATION: Nucleotides at positions 42 and 43 are linked
      by a glycerol linker moiety
<220> FEATURE:
<223> OTHER INFORMATION: Synthetic Construct

<400> SEQUENCE: 60
tcgtcgatcg tcgatcgtcg atcgtcgatc gtcgatcgtc gatcgtcga          49

-continued

```
<210> SEQ ID NO 61
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a linker that includes a hexaethyleneglycol linker
      moiety, a glycerol linker moiety, and a
      hexaethyleneglycol linker moiety
<220> FEATURE:
<223> OTHER INFORMATION: Synthetic Construct

<400> SEQUENCE: 61
tcgacgttcg acgttcgacg t                                         21

<210> SEQ ID NO 62
<211> LENGTH: 21
<212> TYPE: DNA
<213> ORGANISM: Artificial Sequence
<220> FEATURE:
<221> NAME/KEY: misc_feature
<222> LOCATION: 7,8
<223> OTHER INFORMATION: Nucleotides at positions 7 and 8 are linked by
      a hexaethyleneglycol linker moiety
<220> FEATURE:
<221> NAME/KEY: misc_feature
<222> LOCATION: 14,15
<223> OTHER INFORMATION: Nucleotides at positions 14 and 15 are linked
      by a linker that includes a hexaethyleneglycol linker
      moiety, a glycerol linker moiety, and a
      hexaethyleneglycol linker moiety
<220> FEATURE:
<223> OTHER INFORMATION: Synthetic Construct

<400> SEQUENCE: 62
tcgtcgatcg tcgaaacgtt c                                         21
```

IMMUNOMODULATORY COMPOSITIONS, METHODS OF MAKING, AND METHODS OF USE THEREOF

REFERENCE TO RELATED APPLICATIONS

This application claims priority under 35 U.S.C. §119(e) to U.S. Provisional Application No. 60/402,968, filed Aug. 12, 2002, which is incorporated herein by reference in its entirety.

TECHNICAL FIELD

The present invention relates to immunomodulatory formulations, methods of making immunomodulatory formulations, and methods of use thereof. In particular, the invention relates to immunomodulatory formulations comprising a cationic condensing agent, an immunomodulatory compound (IMC), and a stabilizing agent. It also relates to the administration of the immunomodulatory formulations to modulate at least one immune response.

BACKGROUND ART

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495). Interestingly, ISS act through a cell surface receptor (the Toll-like receptor 9, or TLR9), although one recent report suggests that internalization of ISS is necessary for activation of TLR9. Chuang et al., 2002, *J. Leukoc. Biol.* 71(3):538-44; Ahmad-Nejad et al., 2002, *Eur. J. Immunol.* 32(7):1958-68.

Other DNA-based therapies must be internalized before they can act. While certain tissues can take up limited amounts of nucleic acids (Wolff, 1997, *Neuromuscul. Disord.* 7(5):314-8), much attention has been focused on formulations to improve internalization of gene therapy and antisense constructs. Such formulations typically involve the use of a cation to condense the DNA and one or more lipids to (frequently in the form of liposomes) to promote membrane fusion. For example, Semple et al., 2001, *Bioch. Biophys. Acta* 1510:152-166, Cappaccioli et al., 1993, *Bioch. Biophys Res. Comm.* 197(2):818-25, Maurer et al., 2001, *Biophys. J.* 80:2310-26, Shi et al., 2001, *Nucl. Acid Res.* 29(10):2079-87, and Meyer et al., 1998, *J. Biol. Chem.* 273(25):15621-27, all disclose the use of cationic lipid/DNA compositions in serum-containing media in vitro. Other cation/DNA combinations have been tested in serum-containing medium, including DNA with poly-L-lysine (Ginobbi et al., 1997, *Anticancer Res.* 17:29-36, Stewart et al., 199, *Mol. Pharmacol.* 50:1487-94, and Gonzalez-Ferreiro et al., 2001, *J. Controlled Release* 73:381-90), cationic peptides (Junghans et al., 2000, *Nucl. Acid Res.* 28(10):e45, Wyman et al., 1997, *Biochemistry* 36:3008-17), polymerized cationic detergents (Dauty et al., 2001, *J. Am. Chem. Soc.* 123(38):9227-34) polyaminolipids (Guy-Caffey et al., 1995, *J. Biol. Chem.* 270(52):31391-96), cationic block copolymers (Kabanov et al., 1995, *Bioconj. Chem.* 6(6):639-43), and cationic dendrimers (Bielinska et al., 1996, *Nucl. Acid Res.* 24(11):2176-82, Yoo et al., 1999, *Pharmaceut. Res.* 16(12):1799-1804). Legendre et al., 1993, *Proc. Nat'l Acad. Sci. USA* 90:893-97, discloses the use of several different cations, including the cationic antibiotics gramidin S and polymyxin B, to improved transduction of gene therapy constructs. U.S. Pat. No. 5,744,166 discloses pharmaceutical compositions of a polycationic polymer and DNA that may optionally contain poloxamer 407 or gelatin. Chavany et al. (1992, *Pharmaceut. Res.* 9(4):441-49) discloses the effects of a nonionic detergent (poloxamer 188) on a formulation including an alkyltrimethylammonium salt (CTAB) and DNA. Additionally, International Patent Application No. WO 01/15726 discloses combinations of charged lipids and ISS.

SUMMARY OF THE INVENTION

The invention relates to new compositions and methods for modulating immune responses in individuals, particularly human individuals. Applicants have discovered new immunomodulatory compositions having substantially improved immunomodulatory activity.

In one aspect, the invention relates to compositions comprising a cationic condensing agent, an immunomodulatory compound (IMC), and a stabilizing agent. In another aspect, the invention relates to particulate compositions comprising a cationic condensing agent, an immunomodulatory compound (IMC), and a stabilizing agent. Also included are pharmaceutical compositions comprising an immunomodulatory composition of the invention and a pharmaceutically acceptable excipient. In certain embodiments, the compositions of the invention may further include, or optionally exclude, additional components, including fatty acids and/or antigen molecules.

In another aspect, the invention relates to methods of modulating an immune response in an individual, comprising administering to an individual an immunomodulatory composition of the invention in an amount sufficient to modulate an immune response in said individual. Immunomodulation according to the methods of the invention may be practiced on individuals including those suffering from a disorder associated with a Th2-type immune response (e.g., allergies or allergy-induced asthma), individuals receiving vaccines such as therapeutic vaccines (e.g., vaccines comprising an allergy epitope, a mycobacterial epitope, or a tumor associated epitope) or prophylactic vaccines, individuals with cancer, individuals having an infectious disease and individuals at risk of exposure to an infectious agent.

In a further aspect, the invention relates to methods of increasing interferon-gamma (IFN-γ) in an individual, comprising administering an effective amount of an immunomodulatory composition of the invention to the individual. Administration of an immunomodulatory composition of the invention increases IFN-γ in the individual. Suitable subjects for these methods include those individuals having idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ.

In another aspect, the invention relates to methods of increasing IFN-α in an individual, comprising administering an effective amount of an immunomodulatory composition of the invention to the individual. Administration of an immunomodulatory composition of the invention increases IFN-α levels in the individual. Suitable subjects for these methods include those individuals having disorders which respond to the administration of IFN-α, including viral infections and cancer.

In another aspect, the invention relates to methods of ameliorating one or more symptoms of an infectious disease, comprising administering an effective amount of an immunomodulatory composition of the invention to an individual having an infectious disease. Administration of an immunomodulatory composition of the invention ameliorates one or more symptoms of the infectious disease. The infectious diseases which may be treated in accordance with the invention include infectious diseases caused by a cellular pathogen (e.g., a mycobacterial disease, malaria, leishmaniasis, toxoplasmosis, schistosomiasis or clonorchiasis), and may include or exclude viral diseases.

The invention further relates to kits for carrying out the methods of the invention. The kits of the invention generally comprise a container comprising an immunomodulatory composition of the invention (or as described herein, materials for production of an immunomodulatory composition of the invention) and optionally include instructions for use of immunomodulatory composition for the immunomodulation of an individual, for example when the individual suffers from a disorder associated with a Th2-type immune response (e.g., allergies or allergy-induced asthma), is receiving vaccines such as therapeutic vaccines (e.g., vaccines comprising an allergy epitope, a mycobacterial epitope, or a tumor associated epitope) or prophylactic vaccines, suffers from cancer, suffers from an infectious disease or is at risk of exposure to an infectious agent.

The invention also provides methods of making the formulations of the invention, comprising combining an immunomodulatory compound (IMC), a stabilizing agent and a cationic condensing agent to make a mixture. In some embodiments, methods of making the formulations of the invention comprise combining an immunomodulatory compound (IMC) and a stabilizing agent to make an initial mixture, then adding a cationic condensing agent to the initial mixture, resulting in the immunomodulatory composition. The invention further provides immunomodulatory formulations made by these processes.

DETAILED DESCRIPTION OF THE INVENTION

The inventors have discovered new compositions and methods for modulating immune responses in individuals, including and particularly humans. The compositions of the invention comprise a particulate complex of a cationic condensing agent, an immunomodulatory compound (IMC), and a stabilizing agent. Surprisingly, the inventors have found that IMCs formulated with a cationic condensing agent and a stabilizing agent have substantially increased immunomodulatory activity compared to immunomodulatory compounds given alone.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

Definitions

As used herein, the singular form "a", "an", and "the" includes plural references unless indicated otherwise. For example, "an" IMC includes one or more IMCs.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphoester linkages, although alternate linkages, such as phosphorothioate esters may also be used in oligonucleotides. A nucleoside consists of a purine (adenine, guanine or inosine, or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The instant disclosure uses single letters to indicate bases of a nucleotide sequence, where A is adenine, G is guanine, C is cytosine, T is thymine, U is uracil, I is inosine, R is a purine, and Y is a pyrimidine.

The term "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide.

The term "immunomodulatory" and "modulating an immune response," as used herein, refers to immunostimulatory as well as immunosuppressive effects. Immunomodulation is primarily a qualitative alteration in an overall immune response, although quantitative changes may also occur in conjunction with immunomodulation. An immune response that is immunomodulated according to the present invention is one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-γ, IL-2, IL-12, and TNF-β, as well as IFN-α and IL-6, although IL-6 may also be associated with Th2-type responses as well. Th1-type immune responses are generally associated with the production of cytotoxic lymphocytes (CTLs) and low levels or transient production of antibody. Th2-type immune responses are generally associated with higher levels of antibody production, including IgE production, an absence of or minimal CTL production, as well as expression of Th2-associated cytokines such as IL-4. Accordingly, immunomodulation in accordance with the invention may be recognized by, for example, an increase in IFN-γ and/or a decrease in IgE production in an individual treated in accordance with the methods of the invention as compared to the absence of treatment.

The term "immunomodulatory" can refer to the particulate composition and/or the polynucleotide. Thus, an immunomodulatory composition of the invention may exhibit immunomodulatory activity even when the polynucleotide contained in the composition has a sequence that, if presented as a polynucleotide alone, does not exhibit comparable immunomodulatory activity. In some embodiments, when presented alone, a polynucleotide of an immunomodulatory composition of the invention does not have "isolated immunomodulatory activity," or has "inferior isolated immunomodulatory activity," (i.e., when compared to particulate composition). The "isolated immunomodulatory activity" of a polynucleotide is determined by measuring the immunomodulatory activity of the isolated polynucleotide having the same nucleic acid backbone (e.g., phosphorothioate, phosphodiester, chimeric) using standard assays which indicate at least one aspect of an immune response, such as those described herein.

The term "immunomodulatory compound" or "IMC", as used herein, refers to a molecule which has immunomodulatory activity and which comprises a nucleic acid moiety comprising the sequence 5'-CG-3'. The IMC may consist of a nucleic acid moiety that comprises more than one ISS, consists of an ISS, or has no immunomodulatory activity on its own. The IMC may consist of a polynucleotide (a "polynucleotide IMC") or it may comprise additional moieties. Accordingly, the term IMC includes chimeric immunomodulatory compounds ("CICs") which incorporate two or more nucleic acid moieties, at least one of which comprises the sequence 5'-CG-3', covalently linked to a non-nucleotide spacer moiety.

As used herein, the terms "immunomodulatory composition," "particulate composition," and "immunomodulatory particulate composition" refer to a composition comprising a cationic condensing agent, an IMC, and a stabilizing agent.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for inclusion in the compositions of the invention include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g.

sterols, fatty acids, and phospholipids), polysaccharides such as those used in *Hemophilus influenza* vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g. antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant peptides, crude peptide extracts, or peptides in a partially purified or unpurified active state (such as peptides that are a part of attenuated or inactivated viruses, cells, or micro-organisms, or fragments of such peptides). An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

An "individual" is a vertebrate, preferably a mammal, more preferably a human. Mammals include, but are not limited to, humans, primates, farm animals, sport animals, rodents and pets. Vertebrates also include, but are not limited to, birds (i.e., avian individuals) and reptiles (i.e., reptilian individuals).

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to an antigen, an effective amount of an immunomodulatory formulation is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *Hymenoptera* sting allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an immunomodulatory composition of the invention refers to the amount of a given antibody measured at a time point after administration of the immunomodulatory composition.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, an immunomodulatory composition of the invention administered with an antigen or including an antigen which suppresses histamine release reduced histamine release as compared to, for example, histamine release induced by antigen alone.

A "serum protein" is a protein that is normally found in the serum of disease-free mammals, particularly disease-free bovines. The most prevalent serum protein is serum albumin.

As used herein, the term "comprising" and its cognates are used in their inclusive sense; that is, equivalent to the term "including" and its corresponding cognates.

Compositions

The invention provides new compositions for modulating immune response in individuals. The new compositions are formulations comprising a cationic condensing agent, an IMC, and a stabilizing agent. In some embodiments, the compositions of the invention may also comprise an antigen and/or a fatty acid.

The compositions of the invention are typically in particulate form. As will be apparent to those of skill in the art, particulate compositions of the invention will consist of a population of particles of different sizes. Due to this naturally arising variability, the "size" of the particles in the compositions of the invention may be described in ranges or as a maximum or minimum diameter. Particles are considered to be a particular size if at least 95% of the particles (by mass) meet the specified dimension (e.g., if at least 97% of the particles are less than 20 µm in diameter, then the composition is considered to consist of particles of less than 20 µm in diameter). Particle size may be measured by any convenient method known in the art, including filtration (e.g., use of a "depth" filter to capture particles greater than a cutoff size), dynamic light scattering, electron microscopy, including TEM (particularly in combination with freeze-fracture processing) and SEM, and the like.

Preferably, the compositions of the invention comprise particles which are less than about 50 µm in diameter, more preferably less than about 20 µm in diameter, although in some embodiments the particles will be less than about 3, 2 or 1 µm in diameter. Preferred particle size ranges include about 0.01 µm to 50 µm, 0.02 to 20 µm, 0.05 to 5 µm, and 0.05 to 3 µm in diameter.

The components of the compositions of the invention may be present in various ratios/quantities in the compositions, although it is contemplated that the amounts of the stabilizing agent(s) and optional components such as fatty acids and antigen will remain relatively invariant, with stabilizing agents generally ranging from about 0.1% to 0.5% (v/v), fatty acids ranging from about 0 to 0.5%, and antigen concentrations ranging from about 0.1 to about 100 µg/mL, preferably about 1 to about 100 µg/mL, more preferably about 10 to 50 µg/mL. The amounts and ratios of the IMC and the cationic condensing agent are subject to a greater range of variation in the compositions of the invention. The amount of IMC will vary to a certain extent as a function of the molecular weight of the IMC, and generally ranges from about 50 µg/mL to about 2 mg/mL, preferably about 100 µg/mL to 1 mg/mL. The cationic condensing agent is generally present in excess (in terms of mass) over the IMC, generally in ratios of about 1:2 (IMC:cationic condensing agent) to about 1:6, more preferably about 2:5 to 1:5.

Particle size in the compositions of the invention is a function of a number of variables. The inventors have found that the size distribution of particles in the compositions can be modulated by altering the ratio of cationic condensing agent to IMC. For example, altering the ratio of cationic condensing agent to IMC in the exemplary +ISS/0.4% Tween 85/0.4% oleate/polymyxin B compositions can alter mean particle size from about 1.5 µm at cationic condensing agent:IMC=1 to about 45 µm at cationic condensing agent:IMC=10.

In certain embodiments, the compositions comprise a cationic condensing agent, an IMC and a stabilizing agent that is a nonionic detergent. In other embodiments, the compositions comprise a membrane disrupting cationic lipopeptide (preferably a polymyxin, more preferably polymyxin B (PMXB)), an IMC and a stabilizing agent. In some embodiments the stabilizing agent is not a serum protein (particularly not a bovine serum protein). An exemplary composition of this class of embodiments utilizes a polyoxyethylene ether detergent such as Tween 80 or Tween 85 as the stabilizing agent, with oleate as an optional additional stabilizing agent.

In some embodiments, compositions of the invention comprise immunomodulatory particles, wherein the particles are made by the process of combining a cationic condensing agent, an IMC and a stabilizing agent that is a nonionic detergent. In other embodiments, compositions of the invention comprise immunomodulatory particles, wherein the particles are made by the process of combining a membrane disrupting cationic lipopeptide (preferably a polymyxin, more preferably PMBX), an IMC and a stabilizing agent. In some embodiments the stabilizing agent is not a serum protein (particularly not a bovine serum protein).

In some embodiments, compositions of the invention comprise immunomodulatory particles, wherein the particles are formed by the process of combining an IMC and a stabilizing agent that is a nonionic detergent, thereby forming an IMC/stabilizing agent mixture, and combining a cationic condensing agent with the IMC/stabilizing agent mixture. In other embodiments, compositions of the invention comprise immunomodulatory particles, wherein the particles are formed by the process of combining an IMC and a stabilizing agent, thereby forming an IMC/stabilizing agent mixture, and combining a membrane disrupting cationic lipopeptide (preferably a polymyxin, more preferably PMXB) with the IMC/ stabilizing agent mixture. In some embodiments the stabilizing agent is not a serum protein (particularly not a bovine serum protein).

In some embodiments, compositions of the invention comprise immunomodulatory particles, wherein the particles comprise a cationic condensing agent, an IMC and a stabilizing agent that is a nonionic detergent. In other embodiments, compositions of the invention comprise immunomodulatory particles, wherein the particles comprise a membrane disrupting cationic lipopeptide (preferably a polymyxin, more preferably PMXB), an IMC and a stabilizing agent. In some embodiments the stabilizing agent is not a serum protein (particularly not a bovine serum protein).

Cationic Condensing Agents

Cationic condensing agents useful in the compositions and methods of the invention are molecules which are positively charged at physiological pH (i.e., pH of about 7.0 to about 7.5). Preferably, cationic condensing agents used in the instant invention are not zwitterionic and are polycationic, that is, having more than one positive charge per molecule. Cationic condensing agents useful in the instant invention include hydrophilic or amphipathic polycations.

Preferred cationic condensing agents include: (a) membrane disrupting cationic lipopeptides including, but not limited to polymyxins including polymyxin A, polymyxin B (including polymyxin $B_1$ and polymyxin $B_2$), polymyxin C, polymyxin D, polymyxin E (also known as colistin), polymyxin K, polymyxin M, polymyxin P, polymyxin S and polymyxin T, circulins including circulin A, circulin B, circulin C, circulin D, circulin E and circulin F, octapeptin, amphotericins including amphotericin B, and acylated peptides including octanoyl-KFFKFFKFF (SEQ ID NO:42) and acyl KALA (octanoyl-WEAKLAKALAKALA-KHLAKALAKALEACEA (SEQ ID NO:43); (b) membrane disrupting cationic peptides including, but not limited to polymyxin B (PMXB) nonapeptide, cecropins including cecropin A, cecropin B and cecropin P1, KFFKFFKFF (SEQ ID NO:42) and KALA (WEAKLAKALAKALA-KHLAKALAKALKACEA) (SEQ ID NO:44); (c) single chain cationic surfactants including, but not limited to cetyl-trimethylammonium bromide (CTAB), benzyl-dimethyl-ammonium bromide (BDAB), CpyrB (cetyl-pyridinium bromide), CimB (cetyl imidazolium bromide), and polycationic polymers, including, but not limited to, poly-L-lysine (PLL) and polyethyleneimine (PEI). In certain embodiments, the cationic condensing agent is a membrane disrupting cationic lipopeptide, preferably a polymyxin, more preferably PMXB. In some embodiments, cationic condensing agents may exclude fatty acid esters (i.e., lipids) and double chain cationic surfactants.

Immunomodulatory Compounds

In accordance with the present invention, the immunomodulatory compound (IMC) is a molecule which has immunomodulatory activity and which comprises a nucleic acid moiety comprising the sequence 5'-CG-3'. The IMC may be a polynucleotide or it may be a compound which incorporates nucleic acid moieties, at least one of which comprises the sequence 5'-CG-3', such as a CIC. When the IMC is a polynucleotide, the polynucleotide may contain at least one ISS, and can contain multiple ISSs. The ISSs can be adjacent within the polynucleotide, or they can be separated by additional nucleotide bases within the polynucleotide. In certain embodiments, the IMC consists of an ISS. Accordingly, a polynucleotide IMC may contain combinations of any one or more ISS described herein. Alternately, the IMC may be a CIC comprising at least two nucleic acid moieties, at least one of which comprises the sequence 5'-CG-3', covalently linked to a spacer moiety. The IMC affects a measurable immune response, as measured in vitro, in vivo and/or ex vivo, when administered as a component of an immunomodulatory composition of the invention.

A polynucleotide IMC can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is generally unmethylated, especially at the C-5 position, although in certain embodiments, methylation of the cytosine may be permitted, for example, at the N-4 position. A polynucleotide IMC may also comprise the sequence 5'-purine, purine, C, G, pyrimidine, pyrimidine, C, G-3'. A polynucleotide IMC may also comprise the sequence 5'-purine, purine, C, G, pyrimidine, pyrimidine, C, C-3'. As indicated in polynucleotide sequences below, a polynucleotide IMC may comprise (i.e., contain one or more of) the sequence 5'-T, C, G-3' or 5'-T, C, G, A-3'. Accordingly, a polynucleotide IMC may comprise 5'-CG-3' and/or 5'-TCG-3' and/or 5'-TCGA-3', and in certain embodiments uracil (U) may be substituted for thymine. In some embodiments, a polynucleotide IMC may comprise the sequence 5'-C, G, pyrimidine, pyrimidine, C, G-3' (such as 5'-CGTTCG-3'). In some embodiments, a polynucleotide IMC may comprise the sequence 5'-C, G, pyrimidine, pyrimidine, C, G, purine, purine-3'. In some embodiments, a polynucleotide IMC comprises the sequence 5'-purine, purine, C, G, pyrimidine, pyrimidine-3' (such as 5'-AACGTT-3'). As further discussed below, a polynucleotide IMC may contain 5-bromocytosine in place of the "C" in the 5'-CG-3',5'-TCG-3',5'-TCGA-3',5'-UCG-3', or 5'-UCGA-3' of the ISS.

In some embodiments, a polynucleotide IMC may comprise the sequence 5'-purine, T, C, G, pyrimidine, pyrimidine-3'.

In some embodiments, the polynucleotide IMC comprises any of the following sequences: GACGCTCC; GACGTCCC; GACGTTCC; GACGCCCC; AGCGTTCC; AGCGCTCC; AGCGTCCC; AGCGCCCC; AACGTCCC; AACGCCCC; AACGTTCC; AACGCTCC; GGCGTTCC; GGCGCTCC; GGCGTCCC; GGCGCCCC; GACGCTCG; GACGTCCG; GACGCCCG; GACGTTCG; AGCGCTCG; AGCGTTCG; AGCGTCCG; AGCGCCCG; AACGTCCG; AACGCCCG; AACGTTCG; AACGCTCG; GGCGTTCG; GGCGCTCG; GGCGTCCG; GGCGCCCG.

In some embodiments, the polynucleotide IMC comprises any of the following sequences: GACGCT; GACGTC; GACGTT; GACGCC; GACGCU; GACGUC; GACGUU; GACGUT; GACGTU; AGCGTT; AGCGCT; AGCGTC; AGCGCC; AGCGUU; AGCGCU; AGCGUC; AGCGUT; AGCGTU; AACGTC; AACGCC; AACGTT; AACGCT; AACGUC; AACGUU; AACGCU; AACGUT; AACGTU; GGCGTT; GGCGCT; GGCGTC; GGCGCC; GGCGUU; GGCGCU; GGCGUC; GGCGUT; GGCGTU.

In some embodiments, the polynucleotide IMC comprises any of the following sequences: GABGCT; GABGTC; GABGTT; GABGCC; GABGCU; GABGUC; GABGUU; GABGUT; GABGTU; AGBGTT; AGBGCT; AGBGTC; AGBGCC; AGBGUU; AGBGCU; AGBGUC; AGBGUT; AGBGTU; AABGTC; AABGCC; AABGTT; AABGCT; AABGUC; AABGUU; AABGCU; AABGUT; AABGTU; GGBGTT; GGBGCT; GGBGTC; GGBGCC; GGBGUU; GGBGCU; GGBGUC; GGBGUT; GGBGTU, where B is 5-bromocytosine.

In some embodiments, the polynucleotide IMC comprises any of the following sequences: GABGCTCC; GAB- GTCCC; GABGTTCC; GABGCCCC; AGBGTTCC; AGB-GCTCC; AGBGTCCC; AGBGCCCC; AABGTCCC; AAB-GCCCC; AABGTTCC; AABGCTCC; GGBGTTCC; GGBGCTCC; GGBGTCCC; GGBGCCCC; GABGCTCG; GABGTCCG; GABGCCCG; GABGTTCG; AGBGCTCG; AGBGTCCG; AGBGTTCG; AGBGCCCG; AABGTCCG; AABGCCCG; AABGTTCG; AABGCTCG; GGBGTTCG; GGBGCTCG; GGBGTCCG; GGBGCCCG; GABGCTBG; GABGTCBG; GABGCCBG; GABGTTBG; AGBGCTBG; AGBGTTBG; AGBGTCBG; AGBGCCBG; AABGTCBG; AABGCCBG; AABGTTBG; AABGCTBG; GGBGTTBG; GGBGCTBG; GGBGTCBG; GGBGCCBG, where B is 5-bromocytosine.

In some embodiments, the polynucleotide IMC comprises any of the following sequences: GABGCUCC; GAB-GUCCC; GABGUTCC; GABGTUCC; GABGUUCC; AGBGUUCC; AGBGTUCC; AGBGUTCC; AGBGCUCC; AGBGUCCC; AABGUCCC; AABGUUCC; AABGUTCC; AABGTUCC; AABGCUCC; GGBGUUCC; GGBGUTCC; GGBGUUCC; GGBGCUCC; GGBGUCCC; GABGCUCG; GABGUCCG; GABGUUCG; GABGUTCG; GABGTUCG; AGBGCUCG; AGBGUUCG; AGBGUTCG; AGBGTUCG; AGBGUCCG; AABGUCCG; AABGUUCG; AABGUTCG; AABGTUCG; AABGCUCG; GGBGUUCG; GGBGUTCG; GGBGTUCG; GGBGCUCG; GGBGUCCG; GABGCUBG; GABGUCBG; GABGUUBG; GABGUTBG; GABGTUBG; AGBGCUBG; AGBGUUBG; AGBGUCBG; AGBGUTBG; AGBGTUBG; AABGUCBG; AABGUUBG; AABGUTBG; AABGTUBG; AABGCUBG; GGBGUUBG; GGBGUTBG; GGBGTUBG; GGBGCUBG; GGBGUCBG, where B is 5-bromocytosine.

In some embodiments, the immunomodulatory compound comprises the sequence 5'-TGACTGTGAACGTTC-GAGATGA-3' (SEQ ID NO:1). In other embodiments, the polynucleotide IMC comprises any of the sequences:

| | |
|---|---|
| 5'-TGACCGTGAACGTTCGAGATGA-3'; | (SEQ ID NO: 2) |
| 5'-TCATCTCGAACGTTCCACAGTCA-3'; | (SEQ ID NO: 3) |
| 5'-TGACTGTGAACGTTCCAGATGA-3'; | (SEQ ID NO: 4) |
| 5'-TCCATAACGTTCGCCTAACGTTCGTC-3'; | (SEQ ID NO: 5) |
| 5'-TGACTGTGAABGTTCCAGATGA-3', where B is 5-bromocytosine; | (SEQ ID NO: 6) |
| 5'-TGACTGTGAABGTTCGAGATGA-3', where B is 5-bromocytosine; | (SEQ ID NO: 7) |
| 5'-TGACTGTGAABGTTBGAGATGA-3', where B is 5-bromocytosine; | (SEQ ID NO: 8) |
| 5'-GAAABGUTCG-3', where B is 5-bromocytosine; | (SEQ ID NO: 9) |
| 5'-BGAABGUTCG-3', where B is 5-bromocytosine; | (SEQ ID NO: 10) |
| 5'-TCGAGCGTTCT-3'; | (SEQ ID NO: 11) |
| 5'-TGAACGUTCG-3'; | (SEQ ID NO: 12) |
| 5'-GAACCGTTCG-3'; | (SEQ ID NO: 13) |
| 5'-CGAACGTTCG-3'; | (SEQ ID NO: 14) |
| 5'-ATCGACTCTCGAGCGTTCTC-3'; | (SEQ ID NO: 15) |
| 5'-TCGTCGTTTTGTCGTTTTGTCGTT-3'; | (SEQ ID NO: 16) |
| 5'-TCGTCGAACGTTCGTT-3'; | (SEQ ID NO: 17) |
| 5'-TCGTCGAACGTTCG-3'; | (SEQ ID NO: 18) |
| 5'-TCGTCGAACGTT-3'; | (SEQ ID NO: 19) |
| 5'-TCGAACGTTC-3', and | (SEQ ID NO: 20) |
| 5'-TCGTCGAT-3'. | |

In some embodiments, a polynucleotide IMC can be 7 bases (or base pairs) or more. Accordingly, in some embodiments, the polynucleotide IMC comprises or consists of a sequence according to the formula 5'-TCGX$_1$X$_2$X$_3$X$_4$-3' or 5'-UCGX$_1$X$_2$X$_3$X$_4$-3' wherein X$_1$, X$_2$, X$_3$, X$_4$ are nucleotides. In some embodiments, the polynucleotide IMC comprises any of the following sequences: 5'-TCGTTTT-3'; 5'-TCGAAAA-3'; 5'-TCGCCCC-3'; 5'-TCGGGGG-3'; 5'-TCGUUUU-3'; 5'-TCGIIII-3'; 5'-UCGTTTT-3'; 5'-UC-GAAAA-3'; 5'-UCGCCCC-3'; 5'-UCGGGGG-3'; 5'-UCGU-UUU-3'; 5'-UCGIIII-3'. In some embodiments, the polynucleotide IMC comprises or consists of a sequence according to the formula 5'-X$_1$TCGX$_2$X$_3$X$_4$-3' or 5'-X$_1$UCGX$_2$X$_3$X$_4$-3', wherein X$_1$, X$_2$, X$_3$, X$_4$ are nucleotides. In some embodiments, the polynucleotide IMC comprises any of the following sequences: 5'-TTCGTTT-3'; 5'-ATCGATT-3'; 5'-TUCGTTT-3'; 5'-AUCGATT-3'. In other embodiments, the polynucleotide IMC comprises or consist of a sequence according to the formula 5'-X$_1$X$_2$TCGX$_3$X$_4$-3' or 5'-X$_1$X$_2$UCGX$_3$X$_4$-3', wherein X$_1$, X$_2$, X$_3$, X$_4$ are nucleotides. In some embodiments, the polynucleotide IMC comprises any of the following sequences: 5'-TTTCGTT-3'; 5'-AATCGAT-3'; 5'-TTUCGTT-3'; 5'-AAUCGAT-3'.

In certain embodiments, the polynucleotide IMC comprises a sequence of the formula 5'-X$_1$X$_2$ A X$_3$ C G X$_4$ T C G-3' (SEQ ID NO:21) wherein X$_1$ is T, G, C or B (B=5-bromocytosine), wherein X$_2$ is T, G, A or U, wherein X$_3$ is T, A or C, wherein X$_4$ is T, G or U. In certain embodiments, polynucleotide IMCs according to this formula exclude 5'-TGAACGTTCG-3' (SEQ ID NO:22) or 5'-GGAACGT-TCG-3' (SEQ ID NO:23).

In other embodiments, the polynucleotide IMC comprises a sequence of the formula 5'-X$_1$ X$_2$ A X$_3$ B G X$_4$ T C G-3' (SEQ ID NO:24) wherein B is 5-bromocytosine, wherein X$_1$ is T, G, C or B (B=5-bromocytosine), wherein X$_2$ is T, G, A or U, wherein X$_3$ is T, A or C, wherein X$_4$ is T, G or U. In certain embodiments, polynucleotide IMCs according to this formula exclude 5'-TGAABGTTCG-3' (SEQ ID NO:25) (B=5-bromocytosine).

In some embodiments, the polynucleotide IMC comprises the sequence 5'-TCGTCGX$_1$-3', wherein X$_1$ is a nucleotide. In other embodiments, the polynucleotide IMC comprises any of the following sequences: 5'-TCGTCGA-3'; 5'-TCGTCGC-3'; 5'-TCGTCGG-3'; 5'-TCGTCGT-3'; 5'-TCGTCGU-3'; 5'-TCGTCGI-3'. In some embodiments, the polynucleotide IMC comprises the sequence 5'-TCGUCGX$_1$-3', 5'-UCGTCGX$_1$-3', or 5'-UCGUCGX$_1$-3', wherein X$_1$ is a nucleotide. In some embodiments, the polynucleotide IMC comprises any of the following sequences: 5'-TCGUCGA-3'; 5'-TCGUCGC-3'; 5'-TCGUCGG-3'; 5'-TCGUCGT-3'; 5'-TCGUCGU-3'; 5'-TCGUCGI-3'; 5'-UCGTCGA-3'; 5'-UCGTCGC-3'; 5'-UCGTCGG-3'; 5'-UCGTCGT-3'; 5'-UCGTCGU-3'; 5'-UCGTCGI-3'; 5'-UCGUCGA-3'; 5'-UCGUCGC-3'; 5'-UCGUCGG-3'; 5'-UCGUCGT-3'; 5'-UCGUCGU-3'; 5'-UCGUCGI-3'.

In some embodiments, the polynucleotide IMC comprises a sequence according to the formula 5'-T mC GX$_1$X$_2$X$_3$X$_4$-3' or 5'-U mC $GX_1X_2X_3X_4$-3', wherein $X_1$, $X_2$, $X_3$, $X_4$ are nucleotides and wherein mC is a modified cytosine as described herein. In some embodiments, the polynucleotide IMC comprises a sequence according to the formula 5'-$X_1$T mC $GX_2X_3X_4$-3' or 5'-$X_1$U mC $GX_2X_3X_4$-3', wherein $X_1$, $X_2$, $X_3$, $X_4$ are nucleotides. In some embodiments, the ISS comprises a sequence according to the formula 5'-$X_1X_2$T mC $GX_3X_4$-3' or 5'-$X_1X_2$U mC $GX_3X_4$-3', wherein $X_1$, $X_2$, $X_3$, $X_4$ are nucleotides.

In some embodiments, the polynucleotide IMC comprises a sequence according to the formula 5'-T mC $GTCGX_1$-3', 5'-T mC $GUCGX_1$-3', 5'-U mC $GTCGX_1$-3' or 5'-U mC $GUCGX_1$-3', wherein $X_1$ is a nucleotide. In some embodiments, the polynucleotide IMC comprises a sequence according to the formula 5'-TCGT mC $GX_1$-3', 5'-UCGT mC $GX_1$-3'. 5'-TCGU mC $GX_1$-3' or 5'-UCGU mC $GX_1$-3', wherein $X_1$ is a nucleotide. In other embodiments, the polynucleotide IMC comprises a sequence according to the formula 5'-T mC GT mC $GX_1$-3', 5'-U mC GT mC $GX_1$-3', 5'-T mC GU mC $GX_1$-3' or 5'-U mC GU mC $GX_1$-3', wherein $X_1$ is a nucleotide. As described herein, a modified cytosine (mC) includes addition of an electron-withdrawing moiety to C-5 and/or C-6 of a cytosine, including, but not limited to, C-5 halogenated cytosine, such as 5-bromocytosine.

Thus, in some embodiments, the polynucleotide IMC comprises any of the following sequences: 5'-TBGTTTT-3'; 5'-TBGAAAA-3'; 5'-TBGCCCC-3'; 5'-TBGGGGG-3'; 5'-TBGUUUU-3'; 5'-TBGIIII-3'; 5'-TBGTCGA-3'; 5'-TBGTCGC-3'; 5'-TBGTCGG-3'; 5'-TBGTCGT-3'; 5'-TBGTCGU-3'; 5'-TBGTCGI-3'; 5'-TCGTBGA-3'; 5'-TCGTBGC-3'; 5'-TCGTBGG-3'; 5'-TCGTBGT-3'; 5'-TCGTBGU-3'; 5'-TCGTBGI-3'; 5'-TBGTBGA-3'; 5'-TBGTBGC-3'; 5'-TBGTBGG-3'; 5'-TBGTBGT-3', 5'-TBGTBGU-3'; 5'-TBGTBGI-3'; where B is 5-bromocytosine.

In some embodiments, the polynucleotide IMC consists of the sequence 5'-TCGTCG$X_1$-3', wherein $X_1$ is a nucleotide. In certain embodiments, the polynucleotide IMC consists of the sequence 5'-TCGTCGA-3'; 5'-TCGTCGC-3'; 5'-TCGTCGG-3'; 5'-TCGTCGT-3'; 5'-TCGTCGU-3'; 5'-TCGTCGI-3'. In some embodiments, the polynucleotide IMC consists of the sequence 5'-TCGUCG$X_1$-3', 5'-UCGTCG$X_1$-3', or 5'-UCGUCG$X_1$-3', wherein $X_1$ is a nucleotide. In some embodiments, the polynucleotide IMC consists of any of the following sequences: 5'-TCGUCGA-3'; 5'-TCGUCGC-3'; 5'-TCGUCGG-3'; 5'-TCGUCGT-3'; 5'-TCGUCGU-3'; 5'-TCGUCGI-3'; 5'-UCGTCGA-3'; 5'-UCGTCGC-3'; 5'-UCGTCGG-3'; 5'-UCGTCGT-3'; 5'-UCGTCGU-3'; 5'-UCGTCGI-3'; 5'-UCGUCGA-3'; 5'-UCGUCGC-3'; 5'-UCGUCGG-3'; 5'-UCGUCGT-3'; 5'-UCGUCGU-3'; 5'-UCGUCGI-3'.

In some embodiments, the polynucleotide IMC consists of a sequence according to the formula 5'-T mC $GX_1X_2X_3X_4$-3' or 5'-U mC $GX_1X_2X_3X_4$-3', wherein $X_1$, $X_2$, $X_3$, $X_4$ are nucleotides and wherein mC is a modified cytosine as described herein. In some embodiments, the polynucleotide IMC consists of a sequence according to the formula 5'-$X_1$T mC $GX_2X_3X_4$-3' or 5'-$X_1$U mC $GX_2X_3X_4$-3', wherein $X_1$, $X_2$, $X_3$, $X_4$ are nucleotides. In some embodiments, the polynucleotide IMC consists of a sequence according to the formula 5'-$X_1X_2$T mC $GX_3X_4$-3' or 5'-$X_1X_2$U mC $GX_3X_4$-3', wherein $X_1$, $X_2$, $X_3$, $X_4$ are nucleotides.

In some embodiments, the polynucleotide IMC consists of a sequence according to the formula 5'-T mC $GTCGX_1$-3', 5'-T mC $GUCGX_1$-3', 5'-U mC $GTCGX_1$-3' or 5'-U mC $GUCGX_1$-3', wherein $X_1$ is a nucleotide. In some embodiments, the polynucleotide IMC consists of a sequence according to the formula 5'-TCGT mC $GX_1$-3', 5'-UCGT mC $GX_1$-3'. 5'-TCGU mC $GX_1$-3' or 5'-UCGU mC $GX_1$-3', wherein $X_1$ is a nucleotide. In some embodiments, the polynucleotide IMC consists of a sequence according to the formula 5'-T mC GT mC $GX_1$-3', 5'-U mC GT mC $GX_1$-3', 5'-T mC GU mC $GX_1$-3' or 5'-U mC GU mC $GX_1$-3', wherein $X_1$ is a nucleotide. As described herein, a modified cytosine (mC) includes addition of an electron-withdrawing moiety to C-5 and/or C-6 of a cytosine, including, but not limited to, C-5 halogenated cytosine, such as 5-bromocytosine.

Thus, in some embodiments, the polynucleotide IMC consists of any of the following sequences: 5'-TBGTTTT-3'; 5'-TBGAAAA-3'; 5'-TBGCCCC-3'; 5'-TBGGGGG-3'; 5'-TBGUUUU-3'; 5'-TBGIIII-3'; 5'-TBGTCGA-3'; 5'-TBGTCGC-3'; 5'-TBGTCGG-3'; 5'-TBGTCGT-3'; 5'-TBGTCGU-3'; 5'-TBGTCGI-3'; 5'-TCGTBGA-3'; 5'-TCGTBGC-3'; 5'-TCGTBGG-3'; 5'-TCGTBGT-3'; 5'-TCGTBGU-3'; 5'-TCGTBGI-3'; 5'-TBGTBGA-3'; 5'-TBGTBGC-3'; 5'-TBGTBGG-3'; 5'-TBGTBGT-3', 5'-TBGTBGU-3'; 5'-TBGTBGI-3'; where B is 5-bromocytosine.

As described herein, a polynucleotide IMC is any length greater than 6 bases or base pairs. Accordingly, in some embodiments, a polynucleotide IMC is less than about any of the following lengths (in bases or base pairs): 10,000; 5,000; 2500; 2000; 1500; 1250; 1000; 750; 500; 300; 250; 200; 175; 150; 125; 100; 75; 50; 25; 20; 18; 16; 14. In some embodiments, a polynucleotide IMC is greater than about any of the following lengths (in bases or base pairs): 6, 7; 8; 10; 12; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the polynucleotide IMC can be any of a range of sizes having an upper limit of 10,000; 5,000; 2500; 2000; 1500; 1250; 1000; 750; 500; 300; 250; 200; 175; 150; 125; 100; 75; 50; 25; 20; 18; or 16 and an independently selected lower limit of 7; 8; 10; 12; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit.

A polynucleotide moiety of an IMC may contain modifications such as are known in the art including, but are not limited to, modifications of the 3'OH or 5'OH group, modifications of the nucleotide base, modifications of the sugar component, and modifications of the phosphate group. Various such modifications are described below.

It is preferred that cytosines present in the nucleotide moieties of the IMC are not methylated, however, in certain embodiments the IMC may contain on or more methylated cytosines. In such embodiments it is preferred that the cytosine of the 5'-CG-3' of the nucleotide moiety is not methylated at the C-5 position. However, methylation at position N-4 is contemplated in those IMCs with methylated cytosines.

A nucleotide moiety of an IMC may be single stranded or double stranded DNA, as well as single or double-stranded RNA or other modified polynucleotides. An IMC nucleotide moiety may or may not include one or more palindromic regions, which may be present in the motifs described above or may extend beyond the motif, and may comprise additional flanking sequences, some of which are described herein.

A nucleotide moiety of an IMC may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. See, for example, IMCs listed in Table 8. Other non-phosphate linkages may also be used. Preferably, oligonucleotides of the present invention comprise phosphodiester and/or phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine). See, for example, International Patent Application No. WO 99/62923.

The nucleotide moieties of the IMC can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

Nucleotide moieties of the IMC can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular polynucleotide IMC moieties can be isolated, synthesized through recombinant methods, or chemically synthesized. Where the circular polynucleotide IMC moiety is obtained through isolation or through recombinant methods, it will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support in the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

The IMC nucleotide moiety can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Oligonucleotides with phosphorothioate backbones can be more immunogenic than those with phosphodiester backbones and appear to be more resistant to degradation after injection into the host. Braun et al., (1988) *J. Immunol.* 141:2084-2089; and Latimer et al. (1995) *Mol. Immunol.* 32:1057-1064.

Nucleotide moieties of IMCs used in the compositions of the invention can comprise ribonucleotides (containing ribose as the only or principal sugar component), deoxyribonucleotides (containing deoxyribose as the principal sugar component), or, as is known in the art, modified sugars or sugar analogs can be incorporated in the nucleotide moiety. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. The sugar moiety of IMC nucleotide moieties is preferably the furanoside of ribose, deoxyribose, arabinose or 2'-0-alkylribose, and the sugar can be attached to the respective heterocyclic bases either in $\alpha$ or $\beta$ anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of a nucleotide moiety of a IMC.

The heterocyclic bases, or nucleic acid bases, which are incorporated in the nucleotide moiety of the IMC can be the naturally-occurring principal purine and pyrimidine bases, (namely uracil, thymine, cytosine, inosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the nucleotide moiety of the IMC can include one or several heterocyclic bases other than the principal five base components of naturally-occurring nucleic acids. Preferably, however, the heterocyclic base in the nucleotide moiety includes, but is not limited to, uracil-5-yl, cytosin-5-yl, adenin-7-yl, adenin-8-yl, guanin-7-yl, guanin-8-yl, 4-aminopyrrolo[2,3-d]pyrimidin- 5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The nucleotide moiety of the IMC may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidine, 5,6-dihydrocytosine, 5-iodocytosine, hydroxyurea, 5-nitrocytosine, 5-hydroxycytosine and any other pyrimidine analog or modified pyrimidine. Preferred modified uracils are modified at C-5 and/or C-6, preferably with a halogen, and include, but are not limited to, bromouracil such as 5-bromouracil, chlorouracil such as 5-chlorouracil, fluorouracil such as 5-fluorouracil, iodouracil such as 5-iodouracil, and hydroxyuracil. Also see, Kandimalla et al., 2001, *Bioorg. Med. Chem.* 9:807-813. See, for example, International Patent Application No. WO 99/62923. Other examples of base modifications include the addition of one or more thiol groups to the base including, but not limited to, 6-thio-guanine, 4-thio-thymine and 4-thio-uracil. Additionally, some nucleotide moieties may comprise modified bases such as 7-deazaguanosine in place of any guanosine residue, or a modified cytosine selected from N-4-ethylcytosine or N-4-methylcytosine in place of any cytosine residue, including the cytosine of the 5'-CG-3'.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

In certain embodiments, the IMC is a chimeric immunomodulatory compound ("CIC"), such as those described in co-owned U.S. patent application Ser. Nos. 10/176,883 and 10/177,826, filed Jun. 21, 2002, which are fully incorporated by reference herein.

CICs contain one or more nucleic acid moieties and one or more non-nucleic acid spacer moieties. CICs conforming to a variety of structural formulas are contemplated for use as IMCs, including the core structures described in formulas I-VII, below. Formulas I-III show core sequences for "linear CICs." Formulas IV-VI show core sequences for "branched CICs." Formula VII shows a core structure for "single-spacer CICs."

In each formula provided herein, "N" designates a nucleic acid moiety (oriented in either a 5'→3' or 3'→5' orientation) and "S" designates a non-nucleic acid spacer moiety. A dash ("-") designates a covalent bond between a nucleic acid moiety and a non-nucleic acid spacer moiety. A double dash ("--") designates covalent bonds between a non-nucleic acid spacer moiety and at least 2 nucleic acid moieties. A triple dash ("---") designates covalent bonds between a non-nucleic acid spacer moiety and multiple (i.e., at least 3) nucleic acid moieties. Subscripts are used to designate differently positioned nucleic acid or non-nucleic acid spacer moieties. However, the use of subscripts to distinguish different nucleic acid moieties is not intended to indicate that the moieties necessarily have a different structure or sequence. Similarly, the use of subscripts to distinguish different spacer moieties is not intended to indicate that the moieties necessarily have different structures. For example, in formula II, infra, the nucleic acid moieties designated $N_1$ and $N_2$ can have the same or different sequences, and the spacer moieties designated $S_1$ and $S_2$ can have the same or different structures. Further, it is contemplated that additional chemical moieties (e.g., phosphate, mononucleotide, additional nucleic acid moieties, alkyl, amino, thio or disulfide groups or linking groups, and/or spacer moieties) may be covalently bound at the termini of the core structures.

Linear CICs have structures in which the non-nucleic acid spacer moieties in the core structure are covalently bound to no more than two nucleic acid moieties. Exemplary linear CICs conform to the following formulas:

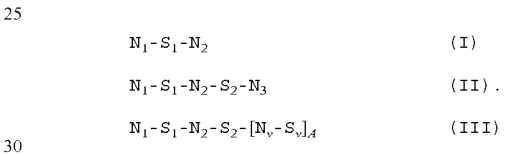

where A is an integer between 1 and about 100 and $[N_v\text{-}S_v]$ indicates A additional iterations of nucleic acid moieties conjugated to non-nucleic acid spacer moieties. The subscript "V" indicates that N and S are independently selected in each iteration of "$[N_v\text{-}S_v]$." "A" is sometimes between 1 and about 10, sometimes between 1 and 3, sometimes exactly 1, 2, 3, 4 or 5. In some embodiments, A is an integer in a range defined by a lower limit of 1, 2, 3, 4, or 5, and an independently selected upper limit of 10, 20, 50 or 100 (e.g., between 3 and 10).

Exemplary linear CICs include:

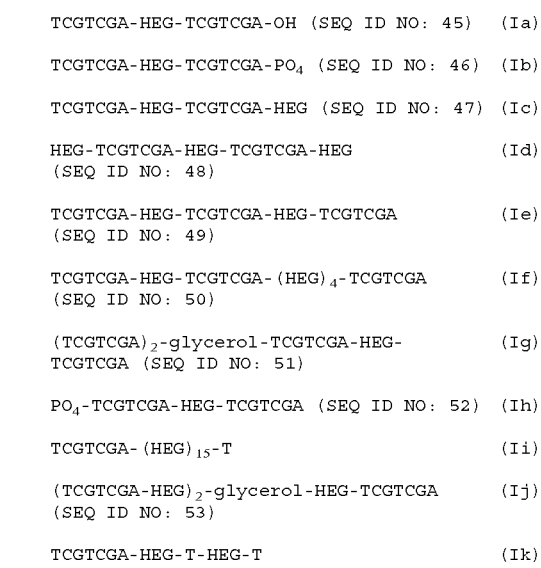

Preferred linear CICs include 5'-TCGTCGA-3'-HEG-5'-ACGTTCG-3'-HEG-5'-AGATGAT-3'(SEQ ID NO:54), 5'-TCGTCG-HEG-AACGTT-HEG-AGATGAT-3'(SEQ ID NO:55), and 5'-TCGTCGA-C3-ACGTTCG-C3-AGATGAT-3' (SEQ ID NO:56).

Branched CICs comprise a multivalent spacer moiety ($S_p$) covalently bound to at least three (3) nucleic acid moieties. Exemplary branched CICs are described according to the following formulas $$[N_v]_A \text{---} S_p \quad \text{(IV)}$$

$$[S_v\text{-}N_v]_A \text{---} S_p \quad \text{(V)}$$

$$(S_1\text{-}N_1)\text{-}S_p\text{--}(N_v)_A \quad \text{(VI)}$$

where $S_p$ is a multivalent spacer covalently bonded to the quantity "A" independently selected nucleic acid moieties $N_v$, $S_v$-$N_v$ (which comprises a spacer moiety covalently bound to a nucleic acid moiety). For formulas IV and V, A is at least 3. In various embodiments of formulas IV and V, A is an integer between 3 and 100 (inclusive), although A may be an integer in a range defined by a lower limit of about 3, 5, 10, 50, or 100 and an independently selected upper limit of about 5, 7, 10, 50, 100, 150, 200, 250, or 500, or alternately A may be greater than 500. For formula VI, A is at least 2, an integer in a range defined by a lower limit of 2, 5, 10, 50, or 100 and an independently selected upper limit of 5, 10, 50, 100, 150, 200, 250, or 500, or greater than 500.

Exemplary branched CICs include:

```
(TCGTCGA)2-glycerol-TCGTCGA (SEQ ID NO: 57)      (IVa)

(TCGTCGA-HEG)2-glycerol-TCGTCGA                  (IVb)
(SEQ ID NO: 58)

(TCGTCGA-HEG-TCGTCGA)2-glycerol-TCGTCGA          (IVc)
(SEQ ID NO: 59)

[(TCGTCGA)2-glycerol-TCGTCGA]2-glycerol-         (IVd)
TCGTCGA (SEQ ID NO: 60)
```

Preferred branched CICs include (5'-TCGACGT-3'-HEG)$_2$-glycerol-HEG-5'-TCGACGT-3'(SEQ ID NO:61) and (5'-TCGTCGA-3'-HEG)$_2$-glycerol-HEG-5'-AACGTTC-3' (SEQ ID NO:62).

Single spacer CICs comprise a structure in which there is a single nucleic acid moiety covalently conjugated to a single spacer moiety, i.e., $$N_1\text{-}S_1 \quad \text{(VII)}$$

In a preferred embodiment $S_1$ has the structure of a multimer comprising smaller units (e.g., HEG, TEG, glycerol, 1'2'-dideoxyribose, C2 alkyl-C12 alkyl subunits, and the like), typically connected by an ester linkage (e.g., phosphodiester or phosphorothioate ester), e.g., as described infra. See, e.g., formula VIIIa, infra. The multimer can be heteromeric or homomeric. In one embodiment, the spacer is a heteromer of monomeric units (e.g., HEG, TEG, glycerol, 1'2'-dideoxyribose, C2 alkyl to C12 alkyl linkers, and the like) linked by an ester linkage (e.g., phosphodiester or phosphorothioate ester). See, e.g., formula VIIb, infra.

Exemplary single spacer CICs include:

```
TCGTCGA-(HEG)15                          (VIIa)

TCGTCGA-HEG-propyl-HEG-propyl-HEG        (VIIb).
```

In certain embodiments, the terminal structures of the CIC are covalently joined (e.g., nucleic acid moiety-to-nucleic acid moiety; spacer moiety-to-spacer moiety, or nucleic acid moiety-to-spacer moiety), resulting in a circular conformation.

CICs for use as IMCs in the immunomodulatory compositions of the invention include at least one nucleic acid moiety. The term "nucleic acid moiety," as used herein, refers to a nucleotide monomer (i.e., a mononucleotide) or polymer (i.e., comprising at least 2 contiguous nucleotides). As used herein, a nucleotide comprises (1) a purine or pyrimidine base linked to a sugar that is in an ester linkage to a phosphate group, or (2) an analog in which the base and/or sugar and/or phosphate ester are replaced by analogs, e.g., as described infra. In a CIC comprising more than one nucleic acid moiety, the nucleic acid moieties may be the same or different.

Nucleic acid moieties used in CICs incorporated in the immunomodulatory compositions may comprise any of the polynucleotide IMC sequences disclosed herein, and may additionally be sequences of six base pairs or less. It is contemplated that in a CIC comprising multiple nucleic acid moieties, the nucleic acid moieties can be the same or different lengths. Nucleic acid moieties of six or fewer nucleotides preferably include the sequence 5'-CG-3', or optionally 5'-TCG-3' or 5'-ACG-3', although in certain embodiments where the CIC comprises more than one nucleic acid moiety, only one of the moieties need comprise the sequence 5'-CG-3'.

It is contemplated that in a CIC comprising multiple nucleic acid moieties, the nucleic acid moieties can be the same or different. Accordingly, in various embodiments, CICs incorporated into the immunomodulatory compositions comprise (a) nucleic acid moieties with the same sequence, (b) more than one iteration of a nucleic acid moiety, or (c) two or more different nucleic acid moieties. Additionally, a single nucleic acid moiety may comprise more than one ISS, which may be adjacent, overlapping, or separated by additional nucleotide bases within the nucleic acid moiety. In an embodiment, a nucleic acid moiety includes one or more palindromic regions. In the context of single-stranded oligonucleotides, the term "palindromic" refers to a sequence that would be palindromic if the oligonucleotide were complexed with a complementary sequence to form a double-stranded molecule. In another embodiment, one nucleic acid moiety has a sequence that is palindromic or partially palindromic in relation to a second nucleic acid moiety in the CIC. In an embodiment of the invention, the sequence of one or more of the nucleic acid moieties of a CIC is not palindromic. In another embodiment of the invention, the sequence of one or more of the nucleic acid moieties of a CIC does not include a palindromic sequence greater than four bases, optionally greater than 6 bases.

The CICs incorporated into the immunomodulatory compositions comprise one or more non-nucleic acid spacer moieties covalently bound to the nucleic acid moieties. For convenience, non-nucleic acid spacer moieties are sometimes referred to herein simply as "spacers" or "spacer moieties." Spacers are generally of molecular weight about 50 to about 50,000, typically from about 75 to about 5000, most often from about 75 to about 500, which are covalently bound, in various embodiments, to one, two, three, or more than three nucleic acid moieties. A variety of agents are suitable for connecting nucleic acid moieties. For example, a variety of compounds referred to in the scientific literature as "non-nucleic acid linkers," "non-nucleotidic linkers," or "valency platform molecules" may be used as spacers in a CIC. In certain embodiments, a spacer comprises multiple covalently connected subunits and may have a homopolymeric or heteropolymeric structure. It will be appreciated that mononucleotides and polynucleotides are not included in the definition of non-nucleic acid spacers, without which exclusion there would be no difference between nucleic acid moiety and an adjacent non-nucleic acid spacer moiety.

In certain embodiments, a spacer may comprise one or more abasic nucleotides (i.e., lacking a nucleotide base, but having the sugar and phosphate portions). Exemplary abasic nucleotides include 1'2'-dideoxyribose, 1'-deoxyribose, 1'-deoxyarabinose and polymers thereof.

Other suitable spacers comprise optionally substituted alkyl, optionally substituted polyglycol, optionally substituted polyamine, optionally substituted polyalcohol, optionally substituted polyamide, optionally substituted polyether, optionally substituted polyimine, optionally substituted polyphosphodiester (such as poly(1-phospho-3-propanol), and the like. Optional substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(=O)CH=CHC(=O) (maleimide), thioether, cyano, sugar (such as mannose, galactose, and glucose), α,β-unsaturated carbonyl, alkyl mercurial, α,β-unsaturated sulfone.

Suitable spacers may comprise polycyclic molecules, such as those containing phenyl or cyclohexyl rings. The spacer may be a polyether such as polyphosphopropanediol, polyethyleneglycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with C1-C5 alkyl, C6 alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. In one embodiment, the spacer comprises 1-phosphopropane)$_3$-phosphate or 1-phosphopropane)$_4$-phosphate (also called tetraphosphopropanediol and pentaphosphopropanediol). In one embodiment, the spacer comprises derivatized 2,2'-ethylenedioxydiethylamine (EDDA).

Specific examples of non-nucleic acid spacers useful in CICs include "linkers" described by Cload and Schepartz, *J. Am. Chem. Soc.* (1991), 113:6324; Richardson and Schepartz, *J. Am. Chem. Soc.* (1991), 113:5109; Ma et al., *Nucleic Acids Research* (1993), 21:2585; Ma et al., *Biochemistry* (1993), 32:1751; McCurdy et al., *Nucleosides & Nucleotides* (1991), 10:287; Jaschke et al., *Tetrahedron Lett.* (1993), 34:301; Ono et al., *Biochemistry* (1991), 30:9914; and Arnold et al., International Publication No. WO 89/02439 entitled "Non-nucleic acid Linking Reagents for Nucleotide Probes."

Other suitable spacers include linkers described by Salunkhe et al., *J. Am. Chem. Soc.* (1992), 114:8768; Nelson et al., *Biochemistry* 35:5339-5344 (1996); Bartley et al., *Biochemistry* 36:14502-511 (1997); Dagneaux et al., *Nucleic Acids Research* 24:4506-12 (1996); Durand et al., *Nucleic Acids Research* 18:6353-59 (1990); Reynolds et al., *Nucleic Acids Research*, 24:760-65 (1996); Hendry et al. *Biochemica et Biophysica Acta*, 1219:405-12 (1994); Altmann et al., *Nucleic Acids Research*, 23:4827-35 (1995). Still other suitable spacers are described in European Patent No. EP0313219B1 (Arnold et al.), "Non-nucleic acid linking reagents for nucleotide probes" and U.S. Pat. No. 6,117,657 (Usman et al.).

Exemplary non-nucleic acid spacers comprise oligo-ethylene glycol (e.g., triethylene glycol, tetraethylene glycol, hexaethylene glycol spacers, and other polymers comprising up to about 10, about 20, about 40, about 50, about 100 or about 200 ethylene glycol units), alkyl spacers (e.g., propyl, butyl, hexyl, and other C2-C12 alkyl spacers, e.g., usually C2-C10 alkyl, most often C2-C6 alkyl), abasic nucleotide spacers, symmetric or asymmetric spacers derived from glycerol, pentaerythritol or 1,3,5-trihydroxycyclohexane (e.g., symmetrical doubler and trebler spacer moieties described herein). Spacers can also comprise heteromeric or homomeric oligomers and polymers of the aforementioned compounds (e.g., linked by an amide, ester, ether, thioether, disulfide, phosphodiester, phosphorothioate, phosphoramidate, phosphotriester, phosphorodithioate, methyl phosphonate or other linkage).

Suitable spacer moieties can contribute charge and/or hydrophobicity to the CIC, contribute favorable pharmacokinetic properties (e.g., improved stability, longer residence time in blood) to the CIC, and/or result in targeting of the CIC to particular cells or organs. Spacer moieties can be selected or modified to tailor the CIC for desired pharmacokinetic properties or suitability for desired modes of administration (e.g., oral administration). It will be appreciated by the reader that, for convenience, a spacer (or spacer component) is sometimes referred to by the chemical name of the compound from which the spacer component is derived (e.g., hexaethylene glycol), with the understanding that the CIC actually comprises the conjugate of the compound and adjacent nucleic acid moieties or other spacer moiety components.

In a CIC comprising more than one spacer moiety, the spacers may be the same or different. Thus, in one embodiment all of the non-nucleic acid spacer moieties in a CIC have the same structure. In one embodiment, a CIC comprises non-nucleic acid spacer moieties with at least 2, at least 3, at least 4, at least 5, or at least 6 or more different structures.

In some contemplated embodiments of the invention, the spacer moiety of a CIC is defined to exclude certain structures. Thus, in some embodiments of the invention, a spacer is other than an abasic nucleotide or polymer of abasic nucleotides. In some embodiments of the invention, a spacer is other than a oligo(ethyleneglycol)(e.g., HEG, TEG and the like) or poly(ethyleneglycol). In some embodiments a spacer is other than a C3 alkyl spacer. In some embodiments, a spacer is other than a polypeptide. Thus, in some embodiments, an immunogenic molecule, e.g., a protein or polypeptide, is not suitable as a component of spacer moieties. However, as discussed infra, it is contemplated that in certain embodiments, a CIC is a "proteinaceous CIC" i.e., comprising a spacer moiety comprising a polypeptide. For example, as discussed infra, in some embodiments, a polypeptide antigen can be used as a platform (multivalent spacer) to which a plurality of nucleic acid moieties are conjugated. However, in some embodiments, the spacer moiety is not proteinaceous and/or is not an antigen (i.e., the spacer moiety, if isolated from the CIC, is not an antigen).

Suitable spacer moieties do not render the CIC of which they are a component insoluble in an aqueous solution (e.g., PBS, pH 7.0). Thus, the definition of spacers excludes microcarriers or nanocarriers. In addition, a spacer moiety that has low solubility, such as a dodecyl spacer (solubility <5 mg/ml when measured as dialcohol precursor 1,12-dihydroxydodecane) is not preferred because it can reduce the hydrophilicity and activity of the CIC. Preferably, spacer moieties have solubility much greater than 5 mg/ml (e.g., ≧20 mg/ml, ≧50 mg/ml or ≧100 mg/ml) when measured as dialcohol precursors.

The charge of a CIC may be contributed by phosphate, thiophosphate, or other groups in the nucleic acid moieties as well as groups in non-nucleic acid spacer moieties. In some embodiments of the invention, a non-nucleic acid spacer moiety carries a net charge (e.g., a net positive charge or net negative charge when measured at pH 7). In one useful embodiment, the CIC has a net negative charge. In some embodiments, the negative charge of a spacer moiety in a CIC is increased by derivatizing a spacer subunit described herein to increase its charge. For example, glycerol can be covalently bound to two nucleic acid moieties and the remaining alcohol can be reacted with an activated phosphoramidite, followed by oxidation or sulfurization to form a phosphate or thiophosphate, respectively. In certain embodiments the negative charge contributed by the non-nucleic acid spacer moieties in a CIC (i.e., the sum of the charges when there is more than one spacer) is greater than the negative charge contributed by the nucleic acid moieties of the CIC. Charge can be calculated based on molecular formula, or determined experimentally, e.g., by capillary electrophoresis (Li, ed., 1992, *Capillary electrophoresis, Principles, Practice and Application* Elsevier Science Publishers, Amsterdam, The Netherlands, pp 202-206).

As is noted supra, suitable spacers can be polymers of smaller non-nucleic acid (e.g., non-nucleotide) compounds, such as those described herein, that are themselves useful as spacers, including compounds commonly referred to as non-nucleotide "linkers." Such polymers (i.e., "multiunit spacers") may be heteromeric or homomeric, and often comprise monomeric units (e.g., HEG, TEG, glycerol, 1'2'-dideoxyribose, and the like) linked by an ester linkage (e.g., phosphodiester or phosphorothioate ester). Thus, in one embodiment the spacer comprises a polymeric (e.g., heteropolymeric) structure of non-nucleotide units (e.g., from 2 to about 100 units, alternatively 2 to about 50, e.g., 2 to about 5, alternatively e.g., about 5 to about 50, e.g., about 5 to about 20).

For illustration, CICs containing multiunit spacers include

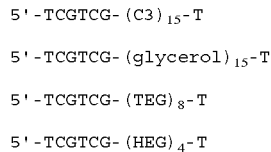

where $(C3)_{15}$ means 15 propyl linkers connected via phosphorothioate esters; $(glycerol)_{15}$ means 15 glycerol linkers connected via phosphorothioate esters; $(TEG)_8$ means 8 triethyleneglycol linkers connected via phosphorothioate esters; and $(HEG)_4$ means 4 hexaethyleneglycol linkers connected via phosphorothioate esters. It will be appreciated that certain multiunit spacers have a net negative charge, and that the negative charge can be increased by increasing the number of e.g., ester-linked monomeric units.

In certain embodiments, a spacer moiety is a multivalent non-nucleic acid spacer moiety (i.e., a "multivalent spacer"). As used in this context, a CIC containing a multivalent spacer contains a spacer covalently bound to three (3) or more nucleic acid moieties. Multivalent spacers are sometimes referred to in the art as "platform molecules." Multivalent spacers can be polymeric or nonpolymeric. Examples of suitable molecules include glycerol or substituted glycerol (e.g., 2-hydroxymethyl glycerol, levulinyl-glycerol); tetraaminobenzene, heptaminobetacyclodextrin, 1,3,5-trihydroxycyclohexane, pentaerythritol and derivatives of pentaerythritol, tetraminopentaerythritol, 1,4,8,11-tetraazacyclo tetradecane (Cyclam), 1,4,7,10-tetraazacyclododecane (Cyclen), polyethyleneimine, 1,3-diamino-2-propanol and substituted derivatives, propyloxymethyl]ethyl compounds (e.g., "trebler"), polyethylene glycol derivatives such as so-called "Star PEGs" and "bPEG" (see, e.g., Gnanou et al., 1988, *Makromol. Chem.* 189:2885; Rein et al., 1993, *Acta Polymer* 44:225, Merrill et al., U.S. Pat. No. 5,171,264; Shearwater Polymers Inc., Huntswlle Ala.), and dendrimers.

Dendrimers are known in the art and are chemically defined globular molecules, generally prepared by stepwise or reiterative reaction of multifunctional monomers to obtain a branched structure (see, e.g., Tomalia et al., 1990, *Angew. Chem. Int. Ed. Engl.* 29:138-75). A variety of dendrimers are known, e.g., amine-terminated polyamidoamine, polyethyleneimine and polypropyleneimine dendrimers. Exemplary dendrimers useful in the present invention include "dense star" polymers or "starburst" polymers such as those described in U.S. Pat. Nos. 4,587,329; 5,338,532; and 6,177,414, including so-called "poly(amidoamine) ("PAMAM") dendrimers." Still other multimeric spacer molecules suitable for use within the present invention include chemically-defined, non-polymeric valency platform molecules such as those disclosed in U.S. Pat. No. 5,552,391; and PCT applications PCT/US00/15968 (published as WO 00/75105); PCT/US96/09976 (published as WO 96/40197), PCT/US97/10075 (published as WO 97/46251); PCT/US94/10031 (published as WO 95/07073); and PCT/US99/29339 (published as WO 00/34231). Many other suitable multivalent spacers can be used and will be known to those of skill in the art.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques.

Multivalent spacers with a variety of valencies are useful in the practice of the invention, and in various embodiments the multivalent spacer of a CIC is bound to between about 3 and about 400 nucleic acid moieties, often from 3 to 100, sometimes from 3-50, frequently from 3-10, and sometimes more than 400 nucleic acid moieties. In various embodiments, the multivalent spacer is conjugated to more than 10, more than 25, more than 50, or more than 500 nucleic acid moieties (which may be the same or different). It will be appreciated that, in certain embodiments in which a CIC comprises a multivalent spacer, the invention provides a population of CICs with slightly different molecular structures. For example, when a CIC is prepared using a dendrimer as a high valency the multivalent spacer, a somewhat heterogeneous mixture of molecules is produced, i.e., comprising different numbers (within or predominantly within a determinable range) of nucleic acid moieties joined to each dendrimer molecule.

Polysaccharides derivatized to allow linking to nucleic acid moieties can be used as spacers in CICs. Suitable polysaccharides include naturally occurring polysaccharides (e.g., dextran) and synthetic polysaccharides (e.g., ficoll). For instance, aminoethylcarboxymethyl-ficoll (AECM-Ficoll) can be prepared by the method of Inman, 1975, *J. Imm.* 114:704-709. AECM-Ficoll can then be reacted with a heterobifunctional crosslinking reagent, such as 6-maleimido caproic acyl N-hydroxysuccinimide ester, and then conjugated to a thiol-derivatized nucleic acid moiety (see Lee, et al., 1980, *Mol. Imm.* 17:749-56). Other polysaccharides may be modified similarly.

It will be well within the ability of one of skill, guided by this specification and knowledge in the art, to prepare CICs using routine methods. Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and TentGel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) *DNA* 3:401; Tang et al. (2000) *Org. Process Res. Dev.* 4:194-198; Wyrzykiewica et al. (1994) *Bioorg. & Med. Chem. Lett.* 4:1519-1522; Radhakrishna et al. (1989) *J. Org. Chem.* 55:4693-4699. and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.).

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O—(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4,4'-dimethoxytrityl)-protected nucleoside-5'-O—(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) *Nucleic Acids Res.* 23:2025-2029 and Wang et al. (1994) *Nucleic Acids Res.* 22:2326-2333.

Addition of non-nucleic acid spacer moieties can be accomplished using routine methods. Methods for addition of particular spacer moieties are known in the art and, for example, are described in the references cited supra. See, e.g., Durand et al., *Nucleic Acids Research* 18:6353-59 (1990). The covalent linkage between a spacer moiety and nucleic acid moiety can be any of a number of types, including phosphodiester, phosphorothioate, amide, ester, ether, thioether, disulfide, phosphoramidate, phosphotriester, phosphorodithioate, methyl phosphonate and other linkages. It will often be convenient to combine a spacer moiety(s) and a nucleic acid moiety(s) using the same phosphoramidite-type chemistry used for synthesis of the nucleic acid moiety. For example, CICs of the invention can be conveniently synthesized using an automated DNA synthesizer (e.g., Expedite 8909; Perseptive Biosystems, Framington, Mass.) using phosphoramidite chemistry (see, e.g., Beaucage, 1993, supra; *Current Protocols in Nucleic Acid Chemistry*, supra). However, one of skill will understand that the same (or equivalent) synthesis steps carried out by an automated DNA synthesizer can also be carried out manually, if desired. In such a synthesis, typically, one end of the spacer (or spacer subunit for multimeric spacers) is protected with a 4,4'-dimethoxytrityl group, while the other end contains a phosphoramidite group.

A variety of spacers with the requisite protecting and reacting groups are commercially available, for example:

| | |
|---|---|
| triethylene glycol spacer or "TEG spacer" | 9-O-(4,4'-dimethoxytrityl)triethyleneglycol-1-O-[(2-cyanoethyl) N,N-diisopropylphosphoramidite] (Glen Research, 22825 Davis Drive, Sterling, VA) |
| hexaethylene glycol spacer or "HEG spacer" | 18-O-(4,4'-dimethoxytrityl)hexaethyleneglycol-1-O-[(2-cyanoethyl) N,N-diisopropylphosphoramidite] (Glen Research, Sterling, VA) |
| propyl spacer | 3-(4,4'-dimethoxytrityloxy)propyloxy-1-O-[(2-cyanoethyl) N,N-diisopropylphosphoramidite] (Glen Research, Sterling, VA); |
| butyl spacer | 4-(4,4'-dimethoxytrityloxy)butyloxy-1-O-[(2-cyanoethyl) N,N-diisopropylphosphoramidite] (Chem Genes Corporation, Ashland Technology Center, 200 Homer Ave, Ashland, MA) |
| Hexyl spacer | 6-(4,4'-dimethoxytrityloxy)hexyloxy-1-O-[(2-cyanoethyl) N,N-diisopropylphosphoramidite] |
| 2-(hydroxymethyl)ethyl spacer or "HME spacer" | 1-(4,4'-dimethoxytrityloxy)-3-(levulinyloxy)-propyloxy-2-O-[(2-cyanoethyl) N,N-diisopropylphosphoramidite]; also called "asymmetrical branched" spacer |
| "abasic nucleotide | 5-O-(4,4'-dimethoxytrityl)-1,2-dideoxyribose-3-O- |

| | |
|---|---|
| "spacer" or "abasic spacer" | [(2-cyanoethyl) N,N-diisopropylphosphoramidite] (Glen Research, Sterling, VA) |
| "symmetrical branched spacer" or "glycerol spacer" | 1,3-O,O-bis(4,4'-dimethoxytrityl)glycerol-2-O-[(2-cyanoethyl) N,N-diisopropylphosphoramidite] (Chem Genes, Ashland, MA) |
| "trebler spacer" | 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, VA) |
| "symmetrical doubler spacer" | 1,3-O,O-bis[5-O-(4,4'-dimethoxytrityloxy)pentylamido]propyl-2-O-[(2-cyanoethyl) N,N-diisopropylphosphoramidite] (Glen Research, Sterling, VA) |
| "dodecyl spacer" | 12-(4,4'-dimethoxytrityloxy)dodecyloxy-1-O-[(2-cyanoethyl) N,N-diisopropylphosphoramidite] (Glen Research, Sterling, VA) |

These and a large variety of other protected spacer moiety precursors (e.g., comprising DMT and phosphoramidite group protecting groups) can be purchased or can be synthesized using routine methods for use in preparing CICs disclosed herein. The instrument is programmed according to the manufacturer's instructions to add nucleotide monomers and spacers in the desired order.

Although use of phosphoramidite chemistry is convenient for the preparation of certain CICs, it will be appreciated that the CICs of the invention are not limited to compounds prepared by any particular method of synthesis or preparation.

In one embodiment, CICs with multivalent spacers conjugated to more than one type of nucleic acid moiety are prepared. For instance, platforms containing two maleimide groups (which can react with thiol-containing polynucleotides), and two activated ester groups (which can react with amino-containing nucleic acids) have been described (see, e.g., PCT/US94/10031, published as WO 95/07073). These two activated groups can be reacted independently of each other. This would result in a CIC containing a total of 4 nucleic acid moieties, two of each sequence.

CICs with multivalent spacers containing two different nucleic acid sequences can also be prepared using the symmetrical branched spacer, described above, and conventional phosphoramidite chemistry (e.g., using manual or automated methods). The symmetrical branched spacer contains a phosphoramidite group and two protecting groups that are the same and are removed simultaneously. In one approach, for example, a first nucleic acid is synthesized and coupled to the symmetrical branched spacer, the protecting groups are removed from the spacer. Then two additional nucleic acids (of the same sequence) are synthesized on the spacer (using double the amount of reagents used for synthesis of a single nucleic acid moiety in each step).

A similar method can be used to connect three different nucleic acid moieties (referred to below as Nucleic acids I, II, and III) to a multivalent platform (e.g., asymmetrical branched spacer). This is most conveniently carried out using an automated DNA synthesizer. In one embodiment, the asymmetrical branched spacer contains a phosphoramidite group and two orthogonal protecting groups that can be removed independently. First, nucleic acid I is synthesized, then the asymmetrical branched spacer is coupled to nucleic acid I, then nucleic acid II is added after the selective removal of one of the protecting groups. Nucleic acid II is deprotected, and capped, and then the other protecting group on the spacer is removed. Finally, nucleic acid III is synthesized.

In some embodiments, a nucleic acid moiety(s) is synthesized, and a reactive linking group (e.g., amino, carboxylate, thio, disulfide, and the like) is added using standard synthetic chemistry techniques. The reactive linking group (which is considered to form a portion of the resulting spacer moiety) is conjugated to additional non-nucleic acid compounds to form the spacer moiety. Linking groups are added to nucleic acids using standard methods for nucleic acid synthesis, employing a variety of reagents described in the literature or commercially available. Examples include reagents that contain a protected amino group, carboxylate group, thiol group, or disulfide group and a phosphoramidite group. Once these compounds are incorporated into the nucleic acids, via the activated phosphoramidite group, and are deprotected, they provide nucleic acids with amino, carboxylate, or thiol reactivity.

Hydrophilic linkers of variable lengths are useful, for example to link nucleic acids moieties and platform molecules. A variety of suitable linkers are known. Suitable linkers include, without limitation, linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. The order of attachment can vary, i.e., the thioether bond can be formed before or after the amide bond is formed. Other useful linkers include Sulfo-SMCC (sulfosuccinimidyl 4-[N-maleimidomethyl]-cyclohexane-1-carboxylate) Pierce Chemical Co. product 22322; Sulfo-EMCS(N-[ε-maleimidocaproyloxy]sulfosuccinimide ester) Pierce Chemical Co. product 22307; Sulfo-GMBS (N-[γ-maleimidobutyryloxy]sulfosuccinimide ester) Pierce Chemical Co. product 22324 (Pierce Chemical Company, Rockford, Ill.), and similar compounds of the general formula maleimido-R—C(O)NHS ester, where R=alkyl, cyclic alkyl, polymers of ethylene glycol, and the like.

Particularly useful methods for covalently joining nucleic acid moieties to multivalent spacers are described in the references cited supra.

In certain embodiments, a polypeptide, such as a protein antigen or antigen fragment, is used as a multivalent spacer moiety to which a plurality of nucleic acid moieties are covalently conjugated, directly or via linkers, to form a "proteinaceous CIC." The polypeptide can be an antigen or immunogen to which an adaptive immune response is desired, or a carrier (e.g., albumin). Typically, a proteinaceous CIC comprises at least one, and usually several or many nucleic acid moieties that (a) are between 2 and 7, more often between 4 and 7 nucleotides in length, alternatively between 2 and 6, 2 and 5, 4 and 6, or 4 and 5 nucleotides in length and/or (b) have inferior isolated immunomodulatory activity or do not have isolated immunomodulatory activity. Methods of making a proteinaceous CIC will be apparent to one of skill upon review of the present disclosure. A nucleic acid, for example, can be covalently conjugated to a polypeptide spacer moiety by art known methods including linkages between a 3' or 5' end of a nucleic acid moiety (or at a suitably modified base at an internal position in the a nucleic acid moiety) and a polypeptide with a suitable reactive group (e.g., an N-hydroxysuccinimide ester, which can be reacted directly with the $N^4$ amino group of cytosine residues). As a further example, a polypeptide can be attached to a free 5'-end of a nucleic acid moiety through an amine, thiol, or carboxyl group that has been incorporated into nucleic acid moiety. Alternatively, the polypeptide can be conjugated to a spacer moiety, as described herein. Further, a linking group comprising a protected amine, thiol, or carboxyl at one end, and a phosphoramidite can be covalently attached to a hydroxyl group of a polynucleotide, and, subsequent to deprotection, the functionality can be used to covalently attach the CIC to a peptide.

Immunomodulatory compounds comprising a nucleotide moiety including the sequence 5'-CG-3' and CIC have been described in the art and in co-owned U.S. Provisional Applications Nos. 60/299,883 and 60/375,253. Immunomodulatory activity of these IMCs and others may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) *Nature* 374:546-549; Yamamoto et al. (1992) *J. Immunol.* 148:4072-4076; Ballas et al. (1996) *J. Immunol.* 157:1840-1845; Klinman et al. (1997) *J. Immunol.* 158:3635-3639; Sato et al. (1996) *Science* 273:352-354; Pisetsky (1996) *J. Immunol.* 156:421-423; Shimada et al. (1986) *Jpn. J. Cancer Res.* 77:808-816; Cowdery et al. (1996) *J. Immunol.* 156:4570-4575; Roman et al. (1997); and Lipford et al. (1997) *Eur. J. Immunol.* 27:2340-2344. These methods are likewise applicable to assessing immunomodulatory activity of an immunomodulatory composition of the invention.

In some embodiments, the IMC is either not active (has no isolated immunomodulatory activity) or is less active (has inferior isolated immunomodulatory activity), as measured in vitro, in vivo and/or ex vivo, in comparison to an immunomodulatory composition of the invention containing the same IMC. As will be understood by those in the art, the determination of the isolated immunomodulatory activity may be concentration-dependent, and an IMC that is determined to have 'no isolated immunomodulatory activity' at a given concentration may indeed have isolated immunomodulatory activity at higher concentrations.

An IMC is characterized as having "inferior immunomodulatory activity," when the test polynucleotide has less activity than an immunomodulatory composition of the invention containing the same IMC when administered at the same concentration of IMC. Preferably the isolated immunomodulatory activity of the test IMC is no more than about 50% of the activity of the immunomodulatory composition, more preferably no more than about 20%, most preferably no more than about 10% of the activity of the immunomodulatory composition, or in some embodiments, even less.

The "isolated immunomodulatory activity" of an IMC is determined by measuring the immunomodulatory activity of the isolated IMC at a given concentration of IMC, measuring the immunomodulatory activity of the IMC administered as part of an immunomodulatory composition of the invention (at the same concentration as the isolated IMC), and comparing the immunomodulatory activity values. Immunomodulatory activity can be determined using standard assays which indicate various aspects of the immune response, such as those described herein. For example, the human PBMC assay described herein may be used. When using the human PBMC assay, the activity of two compounds is typically compared by assaying them in parallel under the same conditions (e.g., using the same cells), usually at a concentration of about 20 µg/ml. Generally, concentration is determined by measuring absorbance at 260 nm and using the conversion 0.5 $OD_{260}$/ml=20 µg/ml. This normalizes the amount of total nucleic acid in the test sample. Alternatively, concentration or weight can be measured by other methods known in the art. To account for donor variation, typically the assay is carried out in multiple donors. An IMC does not have "isolated immunomodulatory activity" when the amount of IFN-γ secreted by PBMCs contacted with the IMC is not significantly greater (e.g., less than about 2-fold greater) in the majority of donors than in the absence of the test compound or, (in some embodiments) in the presence of an inactive control compound (e.g., 5'-TGACTGTGAACCTTAGAGATGA-3')(SEQ ID NO:26).

Stabilizing Agents

Stabilizing agents useful in the instant compositions and methods include those which are suspendable in water and reduce the surface tension of water, although stabilizing agents which are water soluble and/or completely miscible in water are preferred. A number of classes of stabilizing agents are useful in the compositions and methods of the invention, including proteins (preferably hydrophilic proteins), nonionic detergents, polymeric surfactants (e.g., polyvinyl alcohol and polyvinyl pyrrolidone), cationic detergents, anionic detergents and fatty acids, although in certain embodiments, serum proteins (particularly bovine serum proteins), fatty acids, and/or ionic detergents may be excluded from the definition of stabilizing agents.

Any protein may be used as a stabilizing agent in accordance with the invention. In some embodiments, the stabilizing agent is a protein which is not intended as an antigen (see discussion below); in these embodiments, it is preferred that the protein be derived from the same species as the intended recipient of the composition (e.g., if the composition is intended for use in humans, then it is preferred that the protein used as the stabilizing agent be a human protein). Serum albumin is an exemplary protein useful as a stabilizing agent in such embodiments. In other embodiments, an antigen is utilizing as the stabilizing agent, in which case the antigen need not be, and in general is preferably not, species matched with the intended recipient. Antigens useful in the compositions and methods of the invention are disclosed below.

Nonionic detergents useful in the compositions and methods of the invention include glucamides such as decyldimethylphosphine oxide (APO-10) and dimethyldodecylphosphine oxide (APO-12), octanoyl-N-methylglucamide (MEGA-8), nonanoyl-N-methylglucamide (MEGA-9) and decanoyl-N-methyl glucamide (MEGA-10), polyoxyethylene ether detergents including polyoxyethylene(10) dodecyl ester (Genapol C100), polyoxyethylene(4) lauryl ether (BRIJ® 30), polyoxyethylene(9) lauryl ether (LUBROL® PX) polyoxyethylene(23) lauryl ether (BRIJ® 35), polyoxyethylene(2) cetyl ether (BRIJ® 52), polyoxyethylene(10) cetyl ether (BRIJ® 56), polyoxyethylene(20) cetyl ether (BRIJ® 58), polyoxyethylene(2) stearyl ether (BRIJ® 72), polyoxyethylene(10) stearyl ether (BRIJ® 76), polyoxyethylene(20) stearyl ether (BRIJ® 78), polyoxyethylene(100) stearyl ether (BRIJ® 700), polyoxyethylene(2) oleyl ether (BRIJ® 92), polyoxyethylene(10) oleyl ether (BRIJ® 97), polyoxyethylene(20) oleyl ether (BRIJ® 98), isotridecylpoly(ethyleneglycolether)$_8$ (Genapol 80), PLURONIC® F-68, PLURONIC® F-127, dodecylpoly(ethyleneglycolether)$_9$ (Thesit) polyoxyethylene(10) isooctylphenyl ether (TRITON® X-100), polyoxyethylene(8) isooctylphenyl ether (TRITON® X-114), polyethylene glycol sorbitan monolaurate (TWEEN® 20), polyoxyethylenesorbitan monopalmitate (TWEEN® 40), polyethylene glycol sorbitan monostearate (TWEEN® 60), polyoxyethylenesorbitan tristearate (TWEEN® 65), polyethylene glycol sorbitan monooleate (TWEEN® 80), polyoxyethylene(20) sorbitan trioleate (TWEEN® 85), poloxamer 188, and polyethyleneglycol-p-isooctylphenyl ether (Nonidet NP40), alkyl maltoside detergents including cyclohexyl-n-ethyl-β-D-maltoside, cyclohexyl-n-hexyl-β-D-maltoside, and cyclohexyl-n-methyl-β-D-maltoside, n-decanoylsucrose, glucopyranosides including methyl 6-O—(N- heptylcarbamoyl)-a-D-glucopyranoside (HECAMEG) and alkyl glucopyranosides such as n-decyl-β-D-glucopyranoside, n-heptyl-β-D-glucopyranoside, n-dodecyl-β-D-glucopyranoside, n-nonyl-β-D-glucopyranoside, n-octyl-α-D-glucopyranoside, and n-octyl-β-D-glucopyranoside, alkyl thioglucopyranosides including n-heptyl-β-D-thioglucopyranoside, alkyl maltopyranosides including n-decyl-β-D-maltopyranoside and n-octyl-β-D-maltopyranoside, n-decyl-β-D-thiomaltoside, digitonin, n-dodecanoyl sucrose, n-dodecyl-β-D-maltoside, heptane 1,2,3-triol, n-octanoyl-β-D-glucosylamine (NOGA), n-octanoyl sucrose, poloxamers (polyoxyethylene/polyoxypropylene block copolymers) such as poloxamer 188 and poloxamer 407, and sulfobetaines including SB-10, SB-12, and SB-14 and n-undecyl-β-D-maltoside. Preferred stabilizing agents include polyoxyethylene ether detergents, particularly polyethylene glycol sorbitan monooleate and polyoxyethylene(20) sorbitan trioleate.

Anionic detergents useful in the compositions and methods of the invention include caprylic acid and salts thereof, chenodeoxycholic acid and salts thereof, cholic acid and salts thereof, decanesulfonic acid and salts thereof, deoxycholic acid and salts thereof, glycodeoxycholic acid and salts thereof, lauroylsarcosine and salts thereof, n-dodecyl sulfate and salts thereof (including sodium and lithium salts), taurochenodeoxycholic acid and salts thereof, taurocholic acid and salts thereof, taurodehydrocholic acid and salts thereof, taurodeoxycholic acid and salts thereof, taurolithocholic acid and salts thereof, and tauroursodeoxycholic acid and salts thereof.

Cationic detergents include cetylpyridinium and salts thereof, cetyltrimethylamonia and salts thereof including cetyltrimethylammonium bromide (CTAB), dodecyltrimethylammonia and salts thereof including dedecyltrimethylammonium bromide, alklylammonium imidazolines, quaternary imidazolines, and tetradecyltrimtheylammonia and salts thereof including tetradecyltrimtheylammonium bromide.

Detergents selected for use as stabilizing agents are preferably those that are considered oil/water emulsifying detergents. Oil/water emulsifying detergents are known in the art, and are generally characterized by a hydrophobic/lipophilic balance (HLB) value of about 8 to about 18. Preferably, detergents incorporated into the particulate compositions have HLB values of about 10 to about 16, more preferably about 11 to about 15 (e.g., polyethylene glycol sorbitan monooleate, HLB=15.4; polyoxyethylene(10) isooctylphenyl ether, HLB=13.5; polyoxyethylene(20) sorbitan trioleate HLB=11).

Fatty Acids

In certain embodiments, the compositions of the invention may also include one or more fatty acids, or a salt thereof, as an additional component. In those embodiments employing a fatty acid as the stabilizing agent component and a fatty acid as an additional component of the composition, the fatty acid utilized as the stabilizing agent will be different than the fatty acid used as the 'additional' component. Fatty acids useful in the compositions of the invention may range in size from four to 30 carbon atoms, and may be unsaturated (e.g., stearic acid), monounsaturated (e.g., oleic acid), or polyunsaturated (e.g., linoleic acid), although monounsaturated and polyunsaturated fatty acids are generally preferred.

In some embodiments, the compositions of the invention will incorporate a fatty acid having a carbon chain length of at least about 4, 5, 6, 8, 10, 15, 18, or 20 carbon atoms and less than about 30, 25, 20, 19, 15 or 10 carbon atoms. Accordingly, in some embodiments the fatty acids utilized in the invention may have carbon chains with a length in the range of about 4 to 30, 5 to 25, 10 to 20, or 15 to 20 carbon atoms.

Fatty acids useful in the compositions of the invention include, but are not limited to, arachidonic acid, decanoic acid, docosanoic acid, docosahexanoic acid eicosanoic acid, heneicosanoic acid, heptadecanoic acid, heptanoic acid, hexanoic acid, lauric acid, linoleic acid, linolenic acid, myristic acid, nonadecanoic acid, nonanoic acid, octanoic acid, oleic acid, palmitic acid, pentadecanoic acid, stearic acid, tetracosanoic acid, tricosanoic acid, tridecanoic acid, and undecanoic acid, Preferred fatty acids for use in the compositions of the invention include oleic acid palmitoleic acid, and linoleic acid.

Antigens

In certain embodiments of the invention, an antigen is incorporated into the immunomodulatory composition or administered in combination with an immunomodulatory composition. Those immunomodulatory compositions incorporating an antigen may incorporate the antigen into the particulate composition itself, or be dissolved or suspended in the solution in which the particulate composition is suspended. Any antigen may be incorporated into or co-administered with an immunomodulatory composition of the invention.

In some embodiments, the antigen is an allergen. Examples of recombinant allergens are provided in Table 1. Preparation of many allergens is well-known in the art, including, but not limited to, preparation of ragweed pollen allergen Antigen E (Amb a I)(Rafnar et al. (1991) *J. Biol. Chem.* 266:1229-1236), grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet vl (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-31). As indicated, allergens from trees are known, including allergens from birch, juniper and Japanese cedar. Preparation of protein antigens from grass pollen for in vivo administration has been reported.

In some embodiments, the allergen is a food allergen, including, but not limited to, peanut allergen, for example Ara h I (Stanley et al. (1996) *Adv. Exp. Med. Biol.* 409:213-216); walnut allergen, for example, Jug r I (Tueber et al. (1998) *J. Allergy Clin. Immunol.* 101:807-814); brazil nut allergen, for example, albumin (Pastorello et al. (1998) *J. Allergy Clin. Immunol.* 102:1021-1027; shrimp allergen, for example, Pen a I (Reese et al. (1997) *Int. Arch. Allergy Immunol.* 113:240-242); egg allergen, for example, ovomucoid (Crooke et al. (1997) *J. Immunol.* 159:2026-2032); milk allergen, for example, bovine β-lactoglobin (Selot al. (1999) *Clin. Exp. Allergy* 29:1055-1063); fish allergen, for example, parvalbumins (Van Do et al. (1999) *Scand. J. Immunol.* 50:619-625; Galland et al. (1998) *J. Chromatogr. B. Biomed. Sci. Appl.* 706:63-71). In some embodiments, the allergen is a latex allergen, including but not limited to, Hev b 7 (Sowka et al. (1998) *Eur. J. Biochem.* 255:213-219). Table 1 shows an exemplary list of allergens that may be used.

TABLE 1

Recombinant Allergens

| Group | Allergen | Reference |
|---|---|---|
| ANIMALS: CRUSTACEA | | |
| Shrimp/lobster | tropomyosin | Leung et al. (1996) J. Allergy Clin. Immunol. 98: 954-961 |
| | Pan s I | Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |
| | | Forster et al. J Allergy Clin Immunol, 1995, 95: 1229-35 |
| | | Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
| | Bla g 4 (a calycin) | Vailes et al. J Allergy Clin Immunol, 1998, 101: 274-280 |
| | Glutathione S-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4 |
| | | Hakkaart et al. Clin Exp Allergy, 1998, 28: 169-74 |
| | | Hakkaart et al. Clin Exp Allergy, 1998, 28: 45-52 |
| | | Hakkaart et al. Int Arch Allergy Immunol, 1998, 115 (2): 150-6 |
| | | Mueller et al. J Biol Chem, 1997, 272: 26893-8 |
| | Der p2 variant | Smith et al. J Allergy Clin Immunol, 1998, 101: 423-5 |
| | Der f2 | Yasue et al. Clin Exp Immunol, 1998, 113: 1-9 |
| | | Yasue et al. Cell Immunol, 1997, 181: 30-7 |
| | Der p10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
| | | Hoffmann et al. (1997) J Allergy Clin Immunol 99: 227-32 |
| | | Hedlin Curr Opin Pediatr, 1995, 7: 676-82 |
| Cow | Bos d 2 (dander; a lipocalin) | Zeiler et al. J Allergy Clin Immunol, 1997, 100: 721-7 |
| | | Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 |
| | | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
| | | Spitzauer et al. J Allergy Clin Immunol, 1994, 93: 614-27 |
| | | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 |
| | | Grammer et al. J Lab Clin Med, 1987, 109: 141-6 |
| | | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 | Twardosz et al. Biochem Bioph. Res Comm., 1997, 239: 197 |
| | rBet v 1 Bet v 2: (profilin) | Pauli et al. J Allergy Clin Immunol, 1996, 97: 1100-9 |
| | | van Neerven et al. Clin Exp Allergy, 1998, 28: 423-33 |
| | | Jahn-Schmid et al. Immunotechnology, 1996, 2: 103-13 |
| | | Breitwieser et al. Biotechniques, 1996, 21: 918-25 |
| | | Fuchs et al. J Allergy Clin Immunol, 1997, 100: 356-64 |

TABLE 1-continued

Recombinant Allergens

| Group | Allergen | Reference |
|---|---|---|
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
|  |  | Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76 |
|  |  | Vrtala et al. J Immunol Jun. 15, 1998, 160: 6137-44 |
|  |  | Niederberger et al. J Allergy Clin Immun., 1998, 101: 258-64 |
|  | Hol 1 5 velvet grass pollen | Schramm et al. Eur J Biochem, 1998, 252: 200-6 |
|  | Bluegrass allergen | Zhang et al. J Immunol, 1993, 151: 791-9 |
|  | Cyn d 7 Bermuda grass | Smith et al. Int Arch Allergy Immunol, 1997, 114: 265-71 |
|  | Cyn d 12 (a profilin) | Asturias et al. Clin Exp Allergy, 1997, 27: 1307-13 |
|  |  | Fuchs et al. J Allergy Clin Immunol, 1997, 100: 356-64 |
| Japanese Cedar | Jun a 2 (Juniperus ashei) | Yokoyama et al. Biochem. Biophys. Res. Commun., 2000, 275: 195-202 |
|  | Cry j 1, Cry j 2 (Cryptomeria japonica) | Kingetsu et al. Immunology, 2000, 99: 625-629 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9 |
|  |  | Fuchs et al. J Allergy Clin Immunol, 1997, 100: 3 56-64 |
| *Mercurialis* | Mer a I (profilin) | Vallverdu et al. J Allergy Clin Immunol, 1998, 101: 3 63-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6 |
|  |  | Burks et al. J Clin Invest, 1995, 96: 1715-21 |
|  |  | Burks et al. Int Arch Allergy Immunol, 1995, 107: 248-50 |
| *Poa pratensis* | Poa p9 | Parronchi et al. Eur J Immunol, 1996, 26: 697-703 |
|  |  | Astwood et al. Adv Exp Med Biol, 1996, 409: 269-77 |
| Ragweed | Amb a I | Sun et al. Biotechnology Aug, 1995, 13: 779-86 |
|  |  | Hirschwehr et al. J Allergy Clin Immunol, 1998, 101: 196-206 |
|  |  | Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64 |
|  |  | Donovan et al. Electrophoresis, 1993, 14: 917-22 |
| FUNGI: |  |  |
| *Aspergillus* | Asp f 1, Asp f 2, Asp f3, Asp f 4, rAsp f 6 | Crameri et al. Mycoses, 1998, 41 Suppl 1: 56-60 |
|  |  | Hemmann et al. Eur J Immunol, 1998, 28: 1155-60 |
|  |  | Banerjee et al. J Allergy Clin Immunol, 1997, 99: 821-7 |
|  |  | Crameri Int Arch Allergy Immunol, 1998, 115: 99-114 |
|  |  | Crameri et al. Adv Exp Med Biol, 1996, 409: 111-6 |
|  |  | Moser et al. J Allergy Clin Immunol, 1994, 93: 1-11 |
|  | Manganese superoxide dismutase (MNSOD) | Mayer et al. Int Arch Allergy Immunol, 1997, 113: 213-5 |
| *Blomia* | allergen | Caraballo et al. Adv Exp Med Biol, 1996, 409: 81-3 |
| *Penicillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza*, *Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J. Immunol.* 22:477-481; Hirabayashi et al. (1990) *Vaccine* 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these Viruses is Well-Known in the Art and Many are Commercially Available (See, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX® II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides, lipoproteins, and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see Human Retroviruses and AIDS Compendium (for example, 2000 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

In some embodiments, the antigen is linked to the IMC. The IMC can be linked to the antigen in a variety of ways. The link can be made at the 3' or 5' end of the IMC, or to a suitably modified base at an internal position in the IMC. If the peptide contains a suitable reactive group (e.g., an N-hydroxysuccinimide ester) it can be reacted directly with the N 4 amino group of cytosine residues. Depending on the number and location of cytosine residues in the IMC, specific labeling at one or more residues can be achieved.

Alternatively, modified oligonucleosides, such as are known in the art, can be incorporated at either terminus, or at internal positions in the IMC. These can contain blocked functional groups which, when deblocked, are reactive with a variety of functional groups which can be present on, or attached to, a peptide of interest.

The antigen can be attached to the 3'-end of the IMC through solid support chemistry. For example, the IMC can be added to a polypeptide that has been pre-synthesized on a support (Haralambidis et al., *Nucleic Acids Res.* (1990) 18:493-99; Haralambidis et al., *Nucleic Acids Res.* (1990) 18:501-505). Alternatively, the IMC can be synthesized such that it is connected to a solid support through a cleavable linker extending from the 3'-end. Upon chemical cleavage of the IMC from the support, a terminal thiol group is left at the 3'-end of the IMC (Zuckermann et al., *Nucleic Acids Res.* (1987) 15:5305-5321; Corey et al., (1987) *Science* 238:1401-1403), or a terminal amine group is left at the 3'-end of the IMC (Nelson et al., *Nucleic Acids Res.* (1989) 17:1781-94). Conjugation of the amino-modified IMC to amino groups of the peptide can be performed as described in Benoit et al., *Neuromethods* (1987) 6:43-72. Conjugation of the thiol modified IMC to carboxyl groups of the peptide can be performed as described in Sinah et al., Oligonucleotide Analogues: A Practical Approach (1991) IRL Press.

The antigen can be attached to the 5'-end of the IMC through an amine, thiol, or carboxyl group that has been incorporated into the IMC during its synthesis. Preferably, while the IMC is fixed to the solid support, a linking group comprising a protected amine, thiol, or carboxyl at one end, and a phosphoramidite at the other, is covalently attached to the 5'-hydroxyl (Agrawal et al., *Nucleic Acids Res.* (1986) 14:6227-6245; Connolly, *Nucleic Acids Res.* (1985) 13:4485-4502; Coull et al., *Tetrahedron Lett.* (1986) 27:3991-3994; Kremsky et al., *Nucleic Acids Res.* (1987) 15:2891-2909; Connolly, *Nucleic Acids Res.* (1987):3131-3139; Bischoff et al., *Anal. Biochem.* (1987) 164:336-344; Blanks et al., *Nucleic Acids Res.* (1988) 16:10283-10299; U.S. Pat. Nos. 4,849,513, 5,015,733, 5,118,800, and 5,118,802). Subsequent to deprotection, the latent amine, thiol, and carboxyl functionalities can be used to covalently attach the IMC to a peptide (Benoit et al., supra; Sinah et al, Oligonucleotide Analogues: A Practical Approach (1991) IRL Press).

A peptide antigen can be attached to a modified cytosine or uracil at any position in the IMC. The incorporation of a "linker arm" possessing a latent reactive functionality, such as an amine or carboxyl group, at C-5 of the modified base provides a handle for the peptide linkage (Ruth, 4th Annual Congress for Recombinant DNA Research, p. 123).

The linkage of the IMC to a peptide can also be formed through a high affinity, non-covalent interaction such as a biotin-streptavidin complex. A biotinyl group can be attached, for example, to a modified base of an oligonucleotide (Roget et al., *Nucleic Acids Res*. (1989) 17:7643-7651). Incorporation of a streptavidin moiety into the peptide allows formation of a non-covalently bound complex of the streptavidin conjugated peptide and the biotinylated IMC.

The linkage of an IMC to a lipid can be formed using standard methods. These methods include, but are not limited to, the synthesis of oligonucleotide-phospholipid conjugates (Yanagawa et al., *Nucleic Acids Symp. Ser*. (1988) 19:189-92), oligonucleotide-fatty acid conjugates (Grabarek et al., *Anal. Biochem*. (1990) 185:131 35; Staros et al., *Anal. Biochem*. (1986) 156:220-22), and oligonucleotide-sterol conjugates (Boujrad et al., *Proc. Natl. Acad. Sci. USA* (1993) 90:5728 31).

The linkage of IMC to an oligosaccharide can be formed using standard known methods. These methods include, but are not limited to, the synthesis of oligonucleotide-oligosaccharide conjugates, wherein the oligosaccharide is a moiety of an immunoglobulin (O'Shannessy et al., *J. Applied Biochem*. (1985) 7:347 55).

The linkage of IMC to an oligosaccharide can be formed using standard known methods. These methods include, but are not limited to, the synthesis of oligonucleotide-oligosaccharide conjugates, wherein the oligosaccharide is a moiety of an immunoglobulin (O'Shannessy et al., *J. Applied Biochem*. (1985) 7:347 55).

Adjuvants and cytokines may also be genetically or chemically linked to the IMC/antigen conjugates. Examples of this type of fusion peptide are known to those skilled in the art and can also be found in Czerkinsky et al., *Infect. Immun.*, 57: 1072 77 (1989); Nashar et al., *Vaccine*, 11: 235-40 (1993); and Dertzbaugh and Elson, *Infect. Immun.*, 61: 48-55 (1993).

The linkage of a circular IMC to an antigen can be formed in several ways. Where the circular IMC is synthesized using recombinant or chemical methods, a modified nucleoside may be incorporated into the IMC (Ruth, in Oligonucleotides and Analogues: A Practical Approach (1991) IRL Press). Standard linking technology can then be used to connect the circular IMC to the antigen or immunostimulatory peptide (Goodchild, 1990, *Bioconjugate Chem*. 1:165). Where the circular IMC is isolated, or synthesized using recombinant or chemical methods, the linkage can be formed by chemically activating, or photoactivating, a reactive group (e.g., carbene, radical) that has been incorporated into the antigen or immunostimulatory peptide.

Additional methods for the attachment of peptides and other molecules to IMCs can be found in C. Kessler: Nonradioactive labeling methods for nucleic acids in L. J. Kricka (ed.) "Nonisotopic DNA Probe Techniques," Academic Press 1992 and in Geoghegan and Stroh, *Bioconjug. Chem.*, 3:138-146, 1992.

In other embodiments, the IMC and antigen are proximately associated by linkage to a platform molecule. The platform may be proteinaceous or non-proteinaceous (i.e., organic, such as polymers and dendrimers). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res*. 287:123-128; Borel et al. (1995) *Int. Arch. Allergy Immunol*. 107:264-267; Borel et al. (1996) *Ann. N.Y. Acad. Sci*. 778:80-87. A platform is multivalent (i.e., contains more than one binding, or linking, site) to accommodate binding to both an IMC and antigen, and may preferably contain multiple binding sites. Other examples of polymeric platforms are dextran, polyacrylamide, ficoll, carboxymethylcellulose, polyvinyl alcohol, polyethyleneimine, and poly D-glutamic acid/D-lysine.

The principles of using platform molecules are well understood in the art. Generally, a platform contains, or is derivatized to contain, appropriate binding sites for IMC and antigen. In addition, or alternatively, IMC and/or antigen is derivatized to provide appropriate linkage groups. For example, a simple platform is a bi-functional linker (i.e., has two binding sites), such as a peptide.

Preferred platform molecules are biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 200,000, preferably about 200 to about 50,000 (or less, such as 30,000). Examples of valency platform molecules are polymers (or are comprised of polymers) such as polyethylene glycol (PEG), poly-D-lysine, polyvinyl alcohol, polyvinylpyrrollidone, D-glutamic acid and D-lysine (in a ratio of 3:2). Preferred polymers are based on polyethylene glycols (PEGs) having a molecular weight of about 200 to about 8,000. Other molecules that may be used are albumin and IgG.

Other preferred platform molecules suitable for use within the present invention are the chemically-defined, non-polymeric valency platform molecules disclosed in U.S. Pat. No. 5,552,391. Particularly preferred homogeneous chemically-defined valency platform molecules suitable for use within the present invention are derivatized 2,2'-ethylenedioxydiethylamine (EDDA) and triethylene glycol (TEG). Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an IMC and antigen to a platform molecule may be effected in any number of ways, typically involving one or more crosslinking agents and functional groups on the antigen and IMC platform and platform molecule. Platforms and IMC and antigen must have appropriate linking groups. Linking groups are added to platforms using standard synthetic chemistry techniques. Linking groups may be added to polypeptide antigens and IMC using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting IMC and antigen to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

Methods of Making the Compositions

It is well known in the art that DNA will complex with polycationic molecules, generally forming a precipitate or very large particles. The inventors have found that the process by which the compositions are made can control the size of the particles, and thereby affect the potency of the compositions for immunomodulation, as particles of about 0.1 to 20 µm have optimal activity for immunomodulation. Accordingly, the invention also provides methods of making the compositions of the invention, as well as compositions made by these processes.

It is well known in the art that DNA will complex with polycationic molecules, generally forming a precipitate or very large particles. The inventors have found that the process by which the compositions are made can control the size of the particles, and thereby affect the potency of the compositions for immunomodulation, as particles of about 0.1 to 20 µm have optimal activity for immunomodulation. Accordingly, the invention also provides methods of making the compositions of the invention, as well as compositions made by these processes.

Although the compositions of the invention may incorporate hydrophobic components, it is preferred that the compositions be made in an aqueous phase. The aqueous phase may be pure water, but is more preferably an aqueous solution containing one solutes, which may be salts, pH buffers, and the like (collectively "excipients"). Because the compositions of the invention are generally intended for pharmaceutical use, the excipients used in manufacture of the compositions may be pharmaceutically acceptable excipients. However, manufacture of the compositions using excipients which are not pharmaceutically acceptable is also contemplated. When the compositions are manufactured using excipients which are not pharmaceutically acceptable, it is preferred that the composition be manipulated to remove or replace the excipients which are not pharmaceutically acceptable (e.g., by diafiltration or any other convenient technique).

The methods of production of the compositions of the invention may be carried out using conventional processing equipment known in the art, including, for example, mixers, centrifuges, pumps, and other liquid and/or slurry handling machinery. It is preferred that the compositions of the invention are manufactured under sterile conditions, or alternately sterilized after manufacture (e.g., by sterile filtration).

Generally, the immunomodulatory composition is made by combining: at least one IMC, at least one stabilizing agent and at least one cationic condensing agent. Preferably, an aqueous solution containing the IMC is combined with one or more stabilizing agent(s)(either an aqueous solution thereof, or neat stabilizing agent, depending on the physical properties of the stabilizing agent used) and with one or more cationic condensing agent(s). After mixing the components of the compositions, no further processing is believed to be necessary to form the particulate composition. However it is preferred that the IMC/stabilizing agent/cationic condensing agent be allowed to stand for a period of up to about 48 hours, more preferably about 12, 18 or 24 hours.

In some embodiments, the IMC is first combined with one or more cationic condensing agent(s). Preferably, an aqueous solution containing the IMC is combined with one or more cationic condensing agent(s)(either an aqueous solution thereof, or neat cationic condensing agent, depending on the physical properties of the cationic condensing agent used). No incubation time is believed to be necessary after combining the IMC and cationic condensing agent, although the mixture may be made in advance and stored until required.

One or more stabilizing agent(s) is added to the mixture of IMC and cationic condensing to form the particles. No further processing is believed to be necessary to form the compositions. However it is preferred that the IMC/cationic condensing agent/stabilizing agent be allowed to stand for a period of up to about 48 hours, more preferably about 12, 18 or 24 hours.

In some embodiments, the IMC is first combined with one or more stabilizing agent(s). Preferably, an aqueous solution containing the IMC is combined with one or more stabilizing agent(s)(either an aqueous solution thereof, or neat stabilizing agent, depending on the physical properties of the stabilizing agent used). No incubation time is believed to be necessary after combining the IMC and stabilizing agent, although the mixture may be made in advance and stored until required.

The cationic condensing agent is added to the mixture of IMC and stabilizing agent to form the particles. The inventors have found that the compositions of the invention form spontaneously upon combination of the IMC/stabilizing agent mixture with the cationic condensing agent, so no further processing is believed to be necessary to form the compositions. However it is preferred that the IMC/stabilizing agent/cationic condensing agent be allowed to stand for a period of up to about 48 hours, more preferably about 12, 18 or 24 hours.

For production of those compositions which incorporate a fatty acid as an additional component, the fatty acid may be added to the IMC-containing solution (either itself or in combination with the stabilizing agent), to the IMC/stabilizing agent mixture, or simultaneously with the addition of the cationic condensing agent (or as an admixture with the stabilizing agent).

For those compositions which incorporate an antigen, the antigen may be added at any point in the production process. For example, the antigen may be a component of the initial IMC/stabilizing agent mixture, or added before, with, or after the cationic condensing agent. When antigen is added after the addition of the cationic condensing agent, the antigen may be added before or after any purification or size fractionation of the particles.

Mixture of the IMC/stabilizing agent mixture with the cationic condensing agent normally results in the production of particles in a range of sizes (the "bulk product"). Because large sized particles are less desirable for immunomodulation applications and may be less stable, the bulk product is preferably further processed to remove particles outside of the desired size range. A wide variety of size fractionation techniques may be used, including membrane filtration, gel permeation filtration, centrifugation, and even simple settling.

The exact technique and parameters used for size fractionation will depend on excipients used in producing the bulk particle product, the desired particle size range, and the preferences of the user.

As discussed above, the optimal particle size for use in the methods of the invention is about 0.1 to about 20 µm diameter. Accordingly, it is preferred that the particulate compositions be fractionated to remove large particles and the desired particulate composition collected. Large particles may be removed by any convenient technique, including settling under normal gravity, centrifugation, and filtration. The inventors have found that simple settling (i.e., simply allowing the large particles to settle out under the influence of normal gravity) of the bulk particle product for 15 hours yields a composition having a particle diameter of less than 2 µm. This would be approximately equivalent to centrifugation for 10 minutes at 1000 RPM in the commonly used Beckman JA 12 Rotor if the particle size remained constant over the 15 hr period. Filtration with a 2.7 µm pore size filter also yields satisfactory results with regard to elimination of large particles from the bulk particle product. If the production process has not been carried out under sterile conditions and using sterile materials, it is preferred that the composition is sterilized at this point in the process by, for example, sterile filtration.

An aqueous suspension of the particulate composition is expected to be suitable for most indications (sterile if pharmaceutical use contemplated). If the production process has not been carried out in a pharmaceutically acceptable aqueous solution, then it is preferred that the excipient make up of the composition be altered at this point to remove any excipients which are not pharmaceutically acceptable. Non-acceptable excipients may be removed or replaced using conventional technology, such as diafiltration, buffer exchange via gel permeation chromatography, and the like. When the size fractionation technology permits, it may be convenient to combine size fractionation and buffer exchange into a single process (e.g., by performing gel permeation chromatography under conditions which results in size fractionation and buffer exchange).

The compositions of the invention may also be processed to form a dry formulation by, for example, lyophilizing an aqueous suspension of the particulate composition (with or without excipient(s) present). Preferably, one or more bulking agents are added to/dissolved in the composition, which is frozen and lyophilized to yield a dry powder form of the composition. Acceptable bulking agents include, but are not limited to, carbohydrates such as simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin) and glycogen, and synthetic monomers and polymers. Sucrose is an exemplary bulking agent which is typically used at 5 to 15% (w/v), with 10% as an exemplary concentration.

When the composition is to be used as an aqueous suspension, the particle product may then be packaged, preferably under sterile conditions. The exact form of the packaging will vary, depending on the intended use and distribution channel, as well as the preferences of the maker and/or user. For administration as an injectable, the particle product may be dispensed into vials, ampoules, or flexible packaging which has provision for withdrawal of the product. If the product is intended for administration by inhalation, the product may be dispensed into vials, ampoules, etc. for administration by nebulizer, or it may be packaged into disposable package/nozzle combinations for use in a portable inhalation therapy device, such as the AERx® inhalation device (Aradigm Corp.). Alternately, the composition may be dispensed into packaging appropriate for a transdermal or epidermal administration device. The composition may also be mixed with additional excipients or carriers prior to packaging, such as permeability enhancing compounds, lotions, salves, and the like.

Methods of Treatment

The invention provides methods of modulating an immune response in an individual, preferably a mammal, more preferably a human, comprising administering to the individual a composition of the invention. Immunomodulation may include stimulating a Th1-type immune response and/or inhibiting or reducing a Th2-type immune response. The composition of the invention is administered in an amount sufficient to modulate an immune response. As described herein, modulation of an immune response may be humoral and/or cellular, and is measured using standard techniques in the art and as described herein.

The invention provides methods of modulating an immune response in an individual, preferably a mammal, more preferably a human, comprising administering to the individual a composition of the invention. Immunomodulation may include stimulating a Th1-type immune response and/or inhibiting or reducing a Th2-type immune response. The composition of the invention is administered in an amount sufficient to modulate an immune response. As described herein, modulation of an immune response may be humoral and/or cellular, and is measured using standard techniques in the art and as described herein.

A number of individuals are suitable for receiving the immunomodulatory composition(s) described herein. Preferably, but not necessarily, the individual is human.

In certain embodiments, the individual suffers from a disorder associated with a Th2-type immune response, such as allergies or allergy-induced asthma. Administration of a composition of the invention results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., M. tuberculosis antigens as a vaccine for prevention of tuberculosis). Therapeutic vaccines comprise one or more epitopes associated with a particular disorder affecting the individual, such as M. tuberculosis or M. bovis surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. As shown in Example 5, below, administration of a composition of the invention with a hepatitis virus antigen, hepatitis B surface antigen (HBsAg), resulted in increased titers of anti-HBsAg antibodies in mice as compared to administration of HBsAg alone.

The composition of the invention may be given in conjunction with the vaccine (e.g., in the same injection or a contemporaneous, but separate, injection) or the composition of the invention may be administered separately (e.g., at least 12 hours before or after administration of the vaccine). In certain embodiments, the antigen(s) of the vaccine is part of the composition, by either covalent or non-covalent linkage to the IMC or by mixture with the particulate composition. Administration of immunomodulatory composition therapy to an individual receiving a vaccine results in an immune response to the vaccine that is shifted towards a Th1-type response as compared to individuals which receive vaccine in the absence of the compositions of the invention. Shifting towards a Th1-type response may be recognized by a delayed-type hypersensitivity (DTH) response to the antigen(s) in the vaccine, increased IFN-γ and other Th1-type response associated cytokines, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of a composition of the invention and vaccine results in amelioration of one or more symptoms of the disorder which the vaccine is intended to treat. As will be apparent to one of skill in the art, the exact symptom(s) and manner of their improvement will depend on the disorder sought to be treated. For example, where the therapeutic vaccine is for tuberculosis, treatment with the compositions of the invention plus vaccine results in reduced coughing, pleural or chest wall pain, fever, and/or other symptoms known in the art. Where the vaccine is an allergen used in allergy desensitization therapy, the treatment results in a reduction in the symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and/or a reduction in symptom(s). Administration of a composition of the invention to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system. See, for example, Cho et al. (2000) *Nat. Biotechnol.* 18:509-514. In the cancer context, administration of a composition of the invention may further comprise administration of one or more additional therapeutic agents such as, for example, anti-tumor antibodies, chemotherapy regimens and/or radiation treatments. Anti-tumor antibodies, including, but not limited to anti-tumor antibody fragments and/or derivatives thereof, and monoclonal anti-tumor antibodies, fragments and/or derivatives thereof, are known in the art as is administration of such antibody reagents in cancer therapy (e.g., RITUXAN® (rituximab); HERCEPTIN® (trastuzumab)). Administration of one or more additional therapeutic agents may occur before, after and/or concurrent with administration of the particulate composition.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). The composition of the invention may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. The composition of the invention is also useful for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi,* and/or *L. aethiopica*), and toxoplasmosis (i.e., infection by *Toxoplasmosis gondii*) also benefit from particulate composition therapy. Immunomodulatory composition therapy is also useful for treatment of parasitic diseases such as schistosomiasis (i.e., infection by blood flukes of the genus *Schistosoma* such as *S. haematobium, S. mansoni, S. japonicum,* and *S. mekongi*) and clonorchiasis (i.e., infection by *Clonorchis sinensis*). Administration of a particulate composition of the invention to an individual suffering from an infectious disease results in an amelioration of symptoms of the infectious disease. In some embodiments, the infectious disease is not a viral disease.

The invention further provides methods of increasing or stimulating at least one Th1-associated cytokine in an individual, including IL-2, IL-12, TNF-β, IFN-γ and IFN-α. In certain embodiments, the invention provides methods of increasing or stimulating IFN-γ in an individual, particularly in an individual in need of increased IFN-γ levels, by administering an effective amount of an immunomodulatory composition to the individual such that IFN-γ is increased. Individuals in need of increased IFN-γ are those having disorders which generally respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of an immunomodulatory composition in accordance with the invention results in an increase in IFN-γ levels, and results in amelioration of one or more symptoms, stabilization of one or more symptoms, and/or prevention or slowing of progression (e.g., reduction or elimination of additional lesions or symptoms) of the disorder which responds to IFN-γ.

The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of an immunomodulatory composition to the individual such that IFN-α levels are increased. Individuals in need of increased IFN-α are those having disorders which generally respond to the administration of IFN-α, including recombinant IFN-α, including, but not limited to, viral infections and cancer. In certain embodiments, the IMC includes one or more immunomodulatory polynucleotides effective for inducing IFN-α production comprise one or more TCG and/or T, 5-bromocytosine, G sequence(s) in addition to the 5'-CG-3', particularly at the 5' end of the immunomodulatory polynucleotide, as described herein. The additional TCG(s) and/or T, 5-bromocytosine, G(s) may be immediately 5' and adjacent to the CG sequence or may be 5' to the CG sequence with one or more bases separating the TCG and/or T, 5-bromocytosine, G from the CG sequence. In some embodiments, the additional TCG and/or T, 5-bromocytosine, G sequence(s) is created by the addition of a T or a TC or a T, 5-bromocytosine to the 5' end of the CG sequence. In some embodiments where the additional TCG or T, 5-bromocytosine, G sequence is created by the addition of a T or a TC or a T, 5-bromocytosine to the 5' end of the immunomodulatory polynucleotide, the additional sequence may create a TCGA or a T, 5-bromocytosine, G, A sequence with the ISS.

Examples of immunomodulatory polynucleotides particularly effective for inducing IFN-α production include, but are not limited to, 5'-TCGTCGAACGTTCGTTAACGTTCG-3' (SEQ ID NO:27), 5'-TCGTCGAACGTTCGTT-3' (SEQ ID NO:17), 5'-TCGTCGTGAACGTTCGAGATGA-3' (SEQ ID NO:28), 5'-TCGTCGGTATCGGTCGGTATGA-3' (SEQ ID NO:29), 5'-TCGTCGGAACCGTTCGGAATGA-3' (SEQ ID NO:30), 5'-TCGTCGAACGTTCGAGATG-3' (SEQ ID NO:31), 5'-TCGTBGAACGTTCGAGATG-3' (SEQ ID NO:32), 5'-TTCGAACGTTCGTTAACGTTCG-3' (SEQ ID NO:33), 5'-TCGTCGGAAABGUTCGGAATGA-3' (SEQ ID NO:34), 5'-TCGTBGAABGUTCGGAATGA-3' (SEQ ID NO:35), and 5'-TCGTBGTGAACGTTCGAGATGA-3' (SEQ ID NO:36), wherein B=5-bromocytosine.

As will be understood by those of skill in the art, the invention also provides for the use of the compositions of the invention for manufacture of a medicament for use in the methods of treatment described herein, including modulating an immune response, treatment of a disorder associated with a Th2-type immune response, and increasing or stimulating at least one Th1-associated cytokine in an individual.

Administration of an immunomodulatory composition in accordance with the invention results in an increase in IFN-α levels, and results in amelioration of one or more symptoms, stabilization of one or more symptoms, and/or prevention or slowing of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of a particulate composition to the individual. In such methods, the immunomodulatory particulate composition may be administered alone (e.g., without antigen) or administered with antigen, such as an allergen. Reduction in IgE results in an amelioration of one or more symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of an allergic response. Accordingly, the invention also provides methods of treating an allergic condition in an individual. In some embodiments, methods of treating an allergic condition include administering the immunomodulatory composition with a particular amount or dose of antigen. With any additional antigen administration, the amount or dose of antigen administered can remain the same, can decease or can increase (as in conventional desensitization therapy) over the course of treatment.

In some embodiments, the invention provides methods of stimulating CTL production in an individual, particularly in an individual in need of increased number and/or activity of CTLs, comprising administering an effective amount of an immunomodulatory composition to the individual such that CTL production is increased. Individuals in need of increased CTL production are those having disorders which generally respond to CTL activity. Such disorders include, but not limited to, cancer and intracellular infections. Administration of particulate composition in accordance with the invention results in an increase in CTL levels, and results in amelioration of one or more symptoms, stabilization of one or more symptoms, and/or prevention or slowing of progression (e.g., reduction or elimination of additional lesions or symptoms) of the disorder which responds to CTL activity.

Methods of the invention include any embodiments described herein, such as administering particulate compositions with or without antigen.

As will be apparent to one of skill in the art, the methods of the invention may be practiced in combination with other therapies for the particular indication for which the particulate composition is administered. For example, immunomodulatory composition may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

As described herein, administration of immunomodulatory compositions may further comprise administration of one or more additional immunotherapeutic agents (i.e., an agent which acts via the immune system and/or is derived from the immune system) including, but not limited to, cytokine, adjuvants and antibodies (including, but not limited to, antibody fragments and/or derivatives and monoclonal antibodies, fragments and/or derivatives thereof). Examples of therapeutic antibodies include those used in the cancer context (e.g., anti-tumor antibodies). Administration of such additional immunotherapeutic agents applies to all the methods described herein.

An immunomodulatory particulate composition may also be administered in conjunction with an adjuvant. Administration of an antigen with an immunomodulatory particulate composition and an adjuvant leads to a potentiation of a immune response to the antigen and thus, can result in an enhanced immune response compared to that which results from a composition comprising the particulate composition and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873-875, as well as, lipid-based adjuvants and others described herein. Adjuvants are also disclosed in U.S. Pat. No. 6,406,705. For veterinary use and for production of antibodies in animals, mitogenic components of Freund's adjuvant (both complete and incomplete) can be used.

Administration and Assessment of the Immune Response

The immunomodulatory composition can be administered in combination with other pharmaceutical and/or immunogenic and/or immunostimulatory agents, as described herein, and can be combined with a physiologically acceptable carrier thereof (and as such the invention includes these compositions). Accordingly, the immunomodulatory composition can be administered in conjunction with other immunotherapeutic agents including, but not limited to, cytokine, adjuvants and antibodies.

As with all immunogenic compositions, the immunologically effective amounts and method of administration of the particular immunomodulatory composition can vary based on the individual, what condition is to be treated and other factors evident to one skilled in the art. Factors to be considered include the antigenicity of antigen if administered, whether or not the immunomodulatory composition will be administered with or attached, covalently or otherwise, an adjuvant, delivery molecule and/or antigen, route of administration and the number of immunizing doses to be administered. Such factors are known in the art and it is well within the skill of those in the art to make such determinations without undue experimentation. A suitable dosage range is one that provides the desired modulation of immune response (e.g., stimulation of IFN-$\gamma$ and/or IFN-$\alpha$). When an immune response to an antigen is desired, a suitable dosage range is one that provides the desired modulation of immune response to the antigen. Generally, dosage is determined by the amount of the IMC administered to the patient, rather than the overall quantity of particulate composition administered. Useful dosage ranges of the particulate composition, given in amounts of IMC delivered, may be, for example, from about any of the following: 1 to 500 μg/kg, 100 to 400 μg/kg, 200 to 300 μg/kg, 1 to 100 μg/kg, 100 to 200 μg/kg, 300 to 400 μg/kg, 400 to 500 μg/kg. The absolute amount given to each patient depends on pharmacological properties such as bioavailability, clearance rate and route of administration.

The effective amount and method of administration of the particular particulate composition can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient particulate composition to attain a tissue concentration of about 1-10 μM as measured by blood levels. The absolute amount given to each patient depends on pharmacological properties such as bioavailability, clearance rate and route of administration.

As described herein, APCs and tissues with high concentration of APCs are preferred targets for the immunomodulatory particulate composition. Thus, administration of particulate composition to mammalian skin and/or mucosa, where APCs are present in relatively high concentration, is preferred.

The present invention provides immunomodulatory particulate composition formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein an immunomodulatory particulate composition are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the immunomodulatory particulate composition to penetrate the skin and enter the blood stream, although due to the size of the particles, transdermal administration should be performed in conjunction with dermabrasion or other techniques which comprise the integrity of the skin. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up particulate composition transferred from the end of the tines. For example, the MONO-VACC old tuberculin test manufactured by Pasteur Merieux of Lyon, France contains a device suitable for introduction of immunomodulatory particulate compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of immunomodulatory particulate composition. Use of the device is preferably according to the manufacturer's written instructions included with the device product. Similar devices which can also be used in this embodiment are those which are currently used to perform allergy tests.

Another suitable approach to epidermal administration of immunomodulatory compositions is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The particulate composition can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. Formulations of immunomodulatory particulate composition suitable for parenteral administration are generally formulated in USP water or water for injection and may further comprise pH buffers, salts bulking agents, preservatives, and other pharmaceutically acceptable excipients. Immunomodulatory composition for parenteral injection may be formulated in pharmaceutically acceptable sterile isotonic solutions such as saline and phosphate buffered saline for injection.

Gastrointestinal routes of administration include, but are not limited to, ingestion and rectal. The invention includes formulations of the immunomodulatory particulate composition suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes formulations of immunomodulatory particulate composition suitable for administration by inhalation including, but not limited to, liquid suspensions for forming aerosols as well as powder forms for dry powder inhalation delivery systems. Devices suitable for administration by inhalation include, but are not limited to, atomizers, vaporizers, nebulizers, and dry powder inhalation delivery devices.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions or dispersions and sterile powders for the extemporaneous preparation of sterile injectable solutions or dispersion. As will be understood by those of skill in the art, sterile powders are reconstituted by mixing with a suitable carrier before administration. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory polynucleotides of the present invention.

The above-mentioned compositions and methods of administration are meant to describe but not limit the methods of administering the formulations of immunomodulatory compositions of the invention. The methods of producing the various compositions and devices are within the ability of one skilled in the art and are not described in detail here.

Analysis (both qualitative and quantitative) of the immune response to the particulate compositions can be by any method known in the art, including, but not limited to, measuring antigen-specific antibody production (including measuring specific antibody subclasses), activation of specific populations of lymphocytes such as CD4+ T cells, NK cells or CTLs, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity and CTL assays can be performed for instance as described in Raz et al. (1994) *Proc. Natl. Acad. Sci. USA* 91:9519-9523 and Cho et al. (2000). Cytokine concentrations can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with immunomodulatory particulate composition as compared to those treated without the particulate composition. Methods to determine the cytokine production of cells include those methods described herein and any known in the art. The type of cytokines produced in response to particulate composition treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, IFN-γ and IFN-α. In contrast, "Th2-type biased cytokines" refers to those associated with a Th2-type immune response, and include, but are not limited to, IL-4, IL-5, and IL-13. Cells useful for the determination of activity of the particulate compositions include cells of the immune system, primary cells isolated from a host and/or cell lines, preferably APCs and lymphocytes, even more preferably macrophages and T cells.

Stimulation of a Th1-type immune response can also be measured in a host treated with an immunomodulatory particulate composition by any method known in the art including, but not limited to: (1) a reduction in levels of IL-4 or IL-5 measured before and after antigen-challenge; or detection of lower (or even absent) levels of IL-4 or IL-5 in a host treated with the immunomodulatory particulate composition, optionally as compared to an antigen-primed, or primed and challenged, control treated without the particulate composition; (2) an increase in levels of IL-12, IL-18 and/or IFN (α, β or γ) before and after antigen challenge; or detection of higher levels of IL-12, IL-18 and/or IFN (α, β or γ) in a host treated with immunomodulatory particulate composition as compared to an antigen-primed or, primed and challenged, control treated without the particulate composition; (3) "Th1-type biased" antibody production in a host treated with immunomodulatory particulate composition as compared to a control treated without particulate composition; and/or (4) a reduction in levels of antigen-specific IgE as measured before and after antigen challenge; or detection of lower (or even absent) levels of antigen-specific IgE in a host treated with immunomodulatory particulate composition as compared to an antigen-primed, or primed and challenged, control treated without particulate composition. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to immunomodulatory particulate composition treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of administration of immunomodulatory particulate composition produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed (reduced). Suppression of a Th2 response may be determined by, for example, reduction in levels of Th2-associated cytokines, such as IL-4 and IL-5, reduction in the levels of Th2-associated antibodies, as well as IgE reduction and reduction in histamine release in response to allergen.

Kits

The invention provides kits. In certain embodiments, the kits of the invention generally comprise one or more containers comprising any immunomodulatory particulate composition as described herein. Alternately, the kits may comprise one or more containers of the components of the compositions of the invention. Configurations of this embodiment include kits with a container of IMC/stabilizing agent mixture and a container of cationic condensing agent and kits with a container of IMC, a container of stabilizing agent, and a container of cationic condensing agent. The kits may further comprise a suitable set of instructions, generally written instructions, relating to the use of the particulate composition for any of the methods described herein (e.g., immunomodulation, ameliorating one or more symptoms of an infectious disease, increasing IFN-γ levels, increasing IFN-α levels, or ameliorating an IgE-related disorder). The kit embodiments that comprise containers of the components of the compositions will generally include instructions for production of the compositions in accordance with the methods disclosed herein. In addition to the composition and/or components of the composition of the invention, kit embodiments may also enclose instructions for production of the compositions in accordance with the methods disclosed herein and instructions for use of the immunomodulatory compositions for any of the methods described herein.

The kits may comprise immunomodulatory particulate composition packaged in any convenient, appropriate packaging. For example, if the particulate composition is a dry formulation (e.g., freeze dried or a dry powder), a vial with a resilient stopper is normally used, so that the immunomodulatory particulate composition may be easily resuspended by injecting fluid through the resilient stopper. Ampoules with non-resilient, removable closures (e.g., sealed glass) or resilient stoppers are most conveniently used for liquid formulations of particulate composition, although flexible packaging, similar to "blood bags", may also be employed. Also contemplated are packages for use in combination with a specific device, such as an inhaler, nasal administration device (e.g., an atomizer) or an infusion device such as a minipump.

The instructions relating to the use of immunomodulatory particulate composition generally include information as to dosage, dosing schedule, and route of administration for the intended method of use. The containers of immunomodulatory particulate composition may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kits further comprise an antigen (or one or more antigens), which may or may not be packaged in the same container (formulation) as the immunomodulatory particulate composition. Antigens have been described herein.

The following Examples are offered to illustrate but not to limit the invention.

EXAMPLES

Example 1

Immunomodulation of Human Cells with Particulate Formulations Using Albumin as the Stabilizing Agent Polymyxin B (PMXB), polymyxin E (PMXE, also known as colistin), and amphotericin B (AMTB) were combined with an immunomodulatory polynucleotide in serum containing medium (which supplied the stabilizing agent albumin) to create particulate compositions. Immunomodulatory activity of the formulations was tested in an assay which measures interferon (IFN) alpha and gamma production by human peripheral blood lymphocytes (the "hPBMC assay"). The IMC ("+ISS") had the sequence 5'-TGACTGT-GAACGTTCGAGATGA-3' (SEQ ID NO:1), and the negative control oligonucleotide ("−ISS") had the sequence 5'-TGACTGTGAACCTTAGAGATGA-3' (SEQ ID NO:26). Both oligonucleotides were fully modified phosphorothioate oligodeoxynucleotides.

Peripheral blood was collected from volunteers by venipuncture using heparinized syringes. Blood was layered onto FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 24 or 48 well plates at 2×10$^6$ cells/mL in RPMI complete medium (RPMI 1640 with 10% heat-inactivated human AB serum plus 50 units/mL penicillin, 50 µg/mL streptomycin, 300 µg/mL glutamine, 1 mM sodium pyruvate, and 1×MEM non-essential amino acids (NEAA).

Particulate compositions were prepared by adding oligonucleotide (+ISS or −ISS) to 20 µg/ml and PMXB to 100 µg/ml directly to the wells. The cells were cultured in the presence of test samples for 24 hours, then cell-free medium was collected from each well and assayed for IFN-γ and IFN-α concentration. IFN-γ and IFN-α were assayed using CYTOSCREEN™ ELISA kits from BioSource International, Inc., according to the manufacturer's instructions. In the hPBMC assay, background levels of IFN-γ can vary, even significantly, with the donor. Other cytokines such as IFN-α, however, demonstrate a generally stable pattern of activation and routinely exhibit low background levels under unstimulated conditions.

Combination of PMXB and IMC in the presence of albumin resulted in significantly greater IFN-α and IFN-γ secretion as compared to IMC alone (p<0.01) or −ISS in a particulate formulation (p<0.001). This result was particularly impressive because PMXB has no immunomodulatory activity on its own. Results are summarized in Table 2.

TABLE 2

| Donor # | Medium | +ISS | −ISS | PMXB | PMXB/+ISS | PMXB/−ISS |
|---|---|---|---|---|---|---|
| | | | IFN-γ | | | |
| 20 | 1 | 291 | 4 | 20 | 2157 | 250 |
| 75 | 1 | 22 | 1 | 6 | 474 | 127 |
| 96 | 6 | 49 | 9 | 55 | 568 | 41 |
| 97 | 1 | 23 | 5 | 21 | 510 | 151 |
| 37 | 4 | 15 | 5 | 228 | 3000 | 172 |
| 95 | 4 | 6 | 4 | 17 | 350 | 249 |

TABLE 2-continued

| Donor # | Medium | +ISS | −ISS | PMXB | PMXB/+ISS | PMXB/−ISS |
|---|---|---|---|---|---|---|
| 9 | 0 | 20 | 0 | | 153 | 20 |
| 94 | 0 | 30 | 0 | | 197 | 42 |
| 90 | 0 | 13 | 0 | 0 | 240 | 25 |
| 91 | 0 | 27 | 30 | 47 | 1327 | 104 |
| 88 | 9 | 367 | 70 | 112 | 3924 | 2075 |
| 89 | 3 | 100 | 7 | 3 | 406 | 5 |
| 86 | 6 | 182 | 12 | 23 | 2275 | 675 |
| 87 | 4 | 341 | 12 | 33 | 4500 | 425 |
| Mean | 3 | 106 | 11 | 47 | 1434 | 312 |
| | | | IFN-α | | | |
| 37 | 6 | 70 | 0 | 0 | 1244 | 0 |
| 95 | 0 | 26 | 0 | 0 | 1377 | 0 |
| 9 | 0 | 131 | 0 | | 318 | 41 |
| 94 | 0 | 274 | 0 | | 574 | 182 |
| 90 | 1 | 119 | 0 | 0 | 833 | 0 |
| 91 | 2 | 0 | 0 | 0 | 278 | 0 |
| 88 | 6 | 264 | 19 | 33 | 2535 | 0 |
| 89 | 1 | 207 | 17 | 9 | 671 | 16 |
| 86 | 165 | 358 | 15 | 353 | 864 | 341 |
| 87 | 113 | 212 | 0 | 326 | 889 | 125 |
| Mean | 29 | 166 | 5 | 90 | 972 | 78 |

An additional experiment was performed to test amphotericin B as the cationic condensing agent. IMC (+ISS) was mixed with either PMXB (100 µg/ml final concentration) or AMTB (10 µg/ml final concentration) in serum containing medium (which supplied the stabilizing agent albumin) in the culture wells and tested in the hPBMC assay. Like PMXB, AMTB had no activity on its own, but resulted in increased immunomodulatory activity as compared to +ISS alone. Results are summarized in Table 3.

TABLE 3

| | IFN-γ (pg/ml) | | | IFN-α (pg/ml) | | |
|---|---|---|---|---|---|---|
| | Donor 1 | Donor 2 | Mean | Donor 1 | Donor 2 | Mean |
| Medium | 0 | 0 | 0 | 4 | 1 | 2 |
| +ISS | 29 | 0 | 15 | 11 | 2 | 6 |
| −ISS | 1 | 0 | 0 | 3 | 0 | 1 |
| PMXB | 23 | 6 | 15 | 1 | 0 | 0 |
| PMXB/+ISS/HSA | 767 | 190 | 479 | 580 | −90 | 335 |
| PMXB/−ISS/HSA | 17 | 45 | 31 | 1 | 0 | 0 |
| AMTB | 0 | 0 | 0 | 0 | 0 | 0 |
| AMTB/+ISS/HSA | 6 | 48 | 27 | 14 | 2 | 8 |
| AMTB/−ISS/HSA | 0 | 0 | 0 | 0 | 0 | 0 |

Particulate compositions using polymyxin E, a compound closely related to PMXB, as the cationic condensing agent were also tested in the hPBMC assay. The particulate formulations were premade by either (a) O/S+C: mixing oligonucleotide with the stabilizing agent (human serum albumin (HSA) or polyethylene glycol sorbitan monooleate (TWEEN® 80), then combining the oligo/HSA mixture with cationic condensing agent (PMXE or PMXB); or (b) O/C+S: mixing oligonucleotide with cationic condenser, then combining with stabilizing agent. Final concentrations of the components in the formulations were 1 mg/mL IMC, 5 mg/mL PMX, and either 20 mg/mL HSA or 0.4% (v/v) TWEEN® 80. The formulations were allowed to stand for one day at room temperature (approximately 22° C.) before use. Precipitate at the bottom of the vessel was resuspended by vortexing prior to administration to the cultures.

Samples were added to the cultures to a final concentration of 20 µg/ml of oligonucleotide (100 µg/ml of polymyxin for polymyxin controls). Results are summarized in Table 4.

TABLE 4

|  | IFN-γ (pg/ml) | | | IFN-α (pg/ml) | | |
|---|---|---|---|---|---|---|
|  | Donor 28212 | Donor 28213 | Mean | Donor 28212 | Donor 28213 | Mean |
| Controls | | | | | | |
| Medium | 5 | 5 | 5 | 59 | 32 | 46 |
| +ISS | 5 | 17 | 11 | 135 | 109 | 122 |
| −ISS | 5 | 7 | 6 | 225 | 156 | 191 |
| PMXB | 5 | 4 | 5 | 268 | 213 | 241 |
| PMXB/+ISS | 15 | 21 | 18 | 632 | 470 | 551 |
| PMXB/−ISS | 5 | 15 | 10 | 207 | 142 | 175 |

TABLE 4-continued

|  | IFN-γ (pg/ml) | | | IFN-α (pg/ml) | | |
|---|---|---|---|---|---|---|
|  | Donor 28212 | Donor 28213 | Mean | Donor 28212 | Donor 28213 | Mean |
| O/C + S | | | | | | |
| PMXB/+ISS/HSA | 1685 | 67 | 876 | 3303 | 039 | 4171 |
| PMXB/+ISS/Tween | 1577 | 105 | 841 | 32 | 478 | 255 |
| PMXE/+ISS/HSA | 155 | 18 | 87 | 711 | 699 | 705 |
| PMXE/+ISS/Tween | 149 | 13 | 81 | 32 | 32 | 32 |
| O/S + C | | | | | | |
| PMXB/+ISS/HSA | 2333 | 109 | 1221 | 1047 | 1082 | 1065 |
| PMXE/+ISS/HSA | 230 | 12 | 121 | 417 | 295 | 356 |

Example 2

Immunomodulation of Human Cells with Particulate Compositions Utilizing Nonionic Detergents as Stabilizing Agents Particulate compositions produced using polyoxyethylene detergents as the stabilizing agent were tested in the hPBMC assay. Additionally, compositions further incorporating a fatty acid were tested.

Immunomodulatory oligonucleotide +ISS was mixed with polyethylene glycol sorbitan monooleate (TWEEN® 80), then mixed with PMXB to form the particulate compositions. The preparations were allowed to stand for up to seven days before assay in the hPBMC system, which was run as described in Example 1. Final concentrations of the components in the formulations were 1 mg/mL IMC, 5 mg/mL PMX, and either 20 mg/mL HSA or 0.1%-0.4% (v/v) TWEEN® 80. The formulations were allowed to stand for one day at room temperature (approximately 22° C.) before use. Precipitate at the bottom of the vessel was resuspended by vortexing prior to administration to the cultures.

Samples were added to the cultures to a final concentration of 20 μg/ml of oligonucleotide (100 μg/ml polymyxin for polymyxin controls) and assayed using the hPBMC assay run as described in Example 1. All of the particulate compositions were active, including those which were allowed to stand for 7 days before they were assayed. Results are summarized in Table 5.

TABLE 5

| Sample | Time | IFN-γ (pg/ml) Donor 198 | Donor 199 | Mean | IFN-α (pg/ml) Donor 198 | Donor 199 | Mean |
|---|---|---|---|---|---|---|---|
| Medium | | 1 | 7 | 4 | 173 | 126 | 150 |
| +ISS | | 10 | 167 | 88 | 224 | 277 | 250 |
| −ISS | | 5 | 18 | 12 | 151 | 279 | 215 |
| PMXB/+ISS/HSA | 3 hours | 353 | 939 | 646 | 1447 | 632 | 1040 |
| PMXB/+ISS/ 0.2% Tween 80 | 3 hours | 406 | 1054 | 730 | 1814 | 790 | 1302 |
| PMXB/+ISS/ 0.3% Tween 80 | 3 hours | 457 | 877 | 667 | 1617 | 822 | 1219 |
| PMXB/+ISS/ 0.4% Tween 80 | 3 hours | 425 | 729 | 577 | 1746 | 749 | 1247 |
| PMXB/+ISS/HSA | 1 day | 360 | 776 | 568 | 1286 | 456 | 871 |
| PMXB/+ISS/ 0.1% Tween 80 | 1 day | 394 | 824 | 609 | 1719 | 1207 | 1463 |
| PMXB/+ISS/ 0.1% Tween 80 | 4 days | 590 | 300 | 445 | 901 | 130 | 515 |
| PMXB/+ISS/HSA | 7 days | 4000 | 1455 | 2727 | 1529 | 613 | 1071 |

A further experiment was performed testing another polyoxyethylene nonionic detergent (TWEEN® 85) as the stabilizing agent and compositions including a fatty acid (oleic acid). Additionally, one sample was filtered with a 2.7 μm filter prior to assay.

Immunomodulatory oligonucleotide +ISS was mixed with polyoxyethylene(20) sorbitan trioleate (TWEEN® 85), then mixed with PMXB to form the particulate compositions. Final concentrations of the components in the formulations were 1 mg/mL IMC, 5 mg/mL PMX, and either 0.4% (v/v) TWEEN® 85 plus 0.4% oleic acid or 20 mg/mL HSA. The formulations were allowed to stand for one day at room temperature (approximately 22° C.) before use. The preparations were allowed to stand for up to 12 days before assay and resuspended before use.

Samples were added to the cultures to a final concentration of 20 μg/ml of oligonucleotide (100 μg/ml polymyxin for polymyxin controls) and assayed in the hPBMC assay as described in Example 1. Compositions incorporating or polyoxyethylene(20) sorbitan trioleate (TWEEN® 85), with or without oleic acid) as the stabilizing agent were active, even after filtration through a 2.7 μm filter. Results are summarized in Table 6.

TABLE 6

| Sample | Time | Donor 28232 | Donor 28233 | Mean |
|---|---|---|---|---|
| IFN-γ (pg/ml) | | | | |
| Medium |  | 2 | 9 | 6 |
| PMXB |  | 8 | 7 | 7 |
| +ISS |  | 276 | 20 | 148 |
| Tween 85 |  | 15 | 6 | 11 |
| PMXB/+ISS |  | 458 | 11 | 234 |
| PMXB/+ISS/HSA | 3 hours | 737 | 661 | 699 |
| PMXB/+ISS/Tween 85 | 3 hours | 1770 | 492 | 1131 |
| PMXB/+ISS/Tween 85/ Oleic acid | 3 hours | 785 | 477 | 631 |
| PMXB/+ISS/Tween 85 | 1 day | 2662 | 760 | 1711 |
| PMXB/+ISS/Tween 85 | 1 day/Filter | 4000 | 33 | 2017 |
| PMXB/+ISS/Tween 85 | 12 days | 4000 | 4000 | 4000 |
| IFN-α (pg/ml) | | | | |
| Medium |  | 16 | 70 | 43 |
| PMXB |  | 16 | 84 | 50 |
| +ISS |  | 9 | 103 | 56 |
| Tween 85 |  | 66 | 55 | 60 |
| PMXB/+ISS |  | 60 | 93 | 77 |
| PMXB/+ISS/HSA | 3 hours | 2262 | 474 | 1368 |
| PMXB/+ISS/Tween 85 | 3 hours | 2636 | 843 | 1739 |
| PMXB/+ISS/Tween 85/ Oleic acid | 3 hours | 2297 | 663 | 1480 |
| PMXB/+ISS/Tween 85 | 1 day | 4000 | 768 | 2384 |
| PMXB/+ISS/Tween 85 | 1 day/Filter | 115 | 91 | 103 |
| PMXB/+ISS/Tween 85 | 12 days | 3382 | 645 | 2013 |

Example 3

Size Distribution within the Particulate Compositions

Particulate composition was produced by mixing oligonucleotide +ISS (2 mg/mL) with a premixed combination of 0.4% (v/v) polyoxyethylene(20) sorbitan trioleate and 0.4% (v/v) oleic acid, then adding PMXB to 5 mg/mL. The resulting suspension was allowed to stand overnight at room temperature. The supernatant was removed and either used directly (Supe1) or filtered through a 2.7 μm filter (Whatman GF/D with GMF prefilter; Supe2). The pellet was resuspended in an equal volume of PBS.

Particle sizes in aliquots from each of the three samples were measured by laser light scattering with a Malvern Mastersizer instrument, and +ISS concentration was measured by size exclusion chromatography after dissociation of the particles with 0.1 N NaOH. Immunomodulatory activity was measured using the hPBMC assay as described in Example 1.

Supe1 contained particles of about 0.1 to 10 μm in diameter, and was 0.53 mg/mL in +ISS. Supe2 contained particles of about 0.1 to 1 μm in diameter, and was 0.3 mg/mL in +ISS. The pellet contained particles ranging from about 0.1 to 90 μm in diameter (the majority of which were 20-90 μm diameter), and was 0.95 mg/mL in +ISS. All three samples were active in the hPBMC assay, although the pellet was the least active. Results of the hPBMC assay are summarized in Table 7.

TABLE 7

| | IFN-γ (pg/ml) | | | | | IFN-α (pg/ml) | | | | |
|---|---|---|---|---|---|---|---|---|---|---|
| | Donor | | | | | Donor | | | | |
| Sample | 222 | 223 | 224 | 225 | Mean | 222 | 223 | 224 | 225 | Mean |
| None | 1 | 1 | 1 | 1 | 1 | 32 | 107 | 103 | 103 | 86 |
| Supe1 | 4000 | 256 | 404 | 272 | 1283 | 1567 | 265 | 327 | 571 | 682 |
| Supe2 | 1757 | 110 | 280 | 294 | 610 | 1498 | 249 | 344 | 407 | 624 |
| Pellet | 311 | 101 | 96 | 74 | 146 | 997 | 144 | 130 | 154 | 356 |

Example 4

Immunomodulation of Human Cells with Particulate Compositions Incorporating Various Immunomodulatory Polynucleotides A panel of IMCs were incorporated into the particulate compositions and tested for immunomodulatory activity in the hPBMC assay. The panel of IMCs is listed in Table 8 (oligonucleotide backbones are phosphorothioate unless otherwise indicated; bases joined by phosphodiester bonds are in lower case and "ds" indicates double stranded).

TABLE 8

| Name | Sequence | SEQ ID NO |
|---|---|---|
| +ISS | 5'-TGACTGTGAACGTTCGAGATGA-3' | 1 |
| −ISS | 5'-TGACTGTGAACCTTAGAGATGA-3' | 26 |
| +ISS(O/S) | 5'-TGActgtgaacgttcgAGATGA-3' | 40 |
| 20-pG(O/S) | 5'-GGtgcatcgatgcagGGGGG-3' | 37 |
| CIC$_{br}$-HEG | (5'-TCGTCGA-3'-HEG)2-glycerol-HEG-5'-AACGTTC-3' | |

TABLE 8-continued

| Name | Sequence | SEQ ID NO |
|---|---|---|
| CIC-HEG | 5'-TCGTCG-HEG-AACGTT-HEG-AGATGAT-3' | |
| CIC-C₃ | 5'-TCGTCGA-C3-ACGTTCG-C3-AGATGAT-3' | |
| ds + ISS (P=O) | 5'-TGACTGTGAACGTTCGAGATGA-3' | 1 |
| +ISS(P=O) | 5'-TGACTGTGAACGTTCGAGATGA-3' | 1 |
| 16$_{TCG}$ | 5'-TCGTCGAACGTTCGTT-3' | 17 |
| 14$_{TCG}$ | 5'-TCGTCGAACGTTCG-3' | 18 |
| 12$_{TCG}$ | 5'-TCGTCGAACGTT-3' | 19 |
| 10$_{TCG}$ | 5'-TCGAACGTTC-3' | 20 |
| 8$_{TCG}$ | 5'-TCGTCGAT-3' | |
| 7$_{TCG}$ | 5'-TCGTCGA-3' | |
| TCG₂ | 5'-TCGTCG-3' | |
| 5$_{TCG}$ | 5'-TCGTT-3' | |

Particulate formulations were prepared by first preparing a 1 mg/ml oligonucleotide, 0.4% TWEEN® 85, 0.4% oleate solution, then making that solution 5 mg/ml in PMXB. The formulations were allowed to stand for 24 hours at room temperature before assay.

The formulations were vortexed to resuspend any settled precipitate, then added to the cultures to a final concentration of 20 µg/ml of oligonucleotide (100 µg/ml polymyxin for polymyxin controls) and assayed using the hPBMC assay run as described in Example 1. Results are summarized in Table 9.

TABLE 9

| | IFN-γ (pg/ml) | | | |
|---|---|---|---|---|
| Sample | 149 | 206 | 208 | Mean |
| Controls | | | | |
| Medium | 32 | 4 | 4 | 13 |
| PMXB | 195 | 14 | 171 | 127 |
| +ISS | 78 | 5 | 146 | 76 |
| Formulations | | | | |
| +ISS/PMXB | 2446 | 518 | 1377 | 1447 |
| +ISS(O/S)/PMXB | 546 | 134 | 752 | 477 |
| 20-pG(O/S)/PMXB | 1576 | 379 | 1179 | 1045 |
| CIC$_{br}$-HEG/PMXB | 3604 | 660 | 2866 | 2377 |
| CIC-HEG/PMXB | 2554 | 240 | 925 | 1240 |
| CIC-C₃/PMXB | 2596 | 514 | 1357 | 1489 |
| ds+ISS(P + O)/PMXB | 187 | 6 | 186 | 126 |
| +ISS(P + O) | 154 | 4 | 202 | 120 |
| 5$_{TCG}$/PMXB | 23 | 14 | 197 | 78 |
| TGG₂/PMXB | 4 | 5 | 289 | 99 |
| 7$_{TCG}$/PMXB | 48 | 18 | 224 | 97 |
| 8$_{TCG}$/PMXB | 132 | 4 | 188 | 108 |
| 10$_{TCG}$/PMXB | 106 | 4 | 320 | 143 |
| 12$_{TCG}$/PMXB | 165 | 53 | 189 | 136 |
| 14$_{TCG}$/PMXB | 1772 | 716 | 990 | 1159 |
| 16$_{TCG}$/PMXB | 1719 | 678 | 1399 | 1265 |
| | IFN-α (pg/ml) | | | |
| Sample | 149 | 208 | 209 | Mean |
| Controls | | | | |
| Medium | 32 | 32 | 32 | 32 |

TABLE 9-continued

| PMXB | 32 | 32 | 32 | 32 |
|---|---|---|---|---|
| +ISS | 59 | 32 | 32 | 41 |
| Formulations | | | | |
| +ISS/PMXB | 5298 | 566 | 1999 | 2167 |
| +ISS(O/S)/PMXB | 32 | 32 | 277 | 114 |
| 20-pG(O/S)/PMXB | 17915 | 2825 | 15336 | 12025 |
| CIC$_{br}$-HEG/PMXB | 2684 | 412 | 3183 | 2093 |
| CIC-HEG/PMXB | 415 | 32 | 349 | 265 |
| CIC-C₃/PMXB | 3905 | 700 | 1890 | 2165 |
| ds+ISS(P + O)/PMXB | 32 | 32 | 32 | 32 |
| +ISS(P + O) | 32 | 32 | 32 | 32 |
| 5$_{TCG}$/PMXB | 32 | 32 | 32 | 32 |
| TGG₂/PMXB | 32 | 32 | 32 | 32 |
| 7$_{TCG}$/PMXB | 32 | 32 | 32 | 32 |
| 8$_{TCG}$/PMXB | 32 | 32 | 32 | 32 |
| 10$_{TCG}$/PMXB | 32 | 32 | 32 | 32 |
| 12$_{TCG}$/PMXB | 32 | 32 | 32 | 32 |
| 14$_{TCG}$/PMXB | 2345 | 1240 | 2189 | 1925 |
| 16$_{TCG}$/PMXB | 5245 | 875 | 3175 | 3098 |

Example 5

Polymyxin Domains and Enhancement of ISS Activity

PMXB has two major domains: (1) a cyclic peptide that contains 5 positively charged amino acid residues and (2) an N-terminal lipophilic fatty acyl derivative. In order to determine whether one or both domains are required in order to enhance IMC activity, IMC-enhancing potential of two derivatives of the polymyxin family was examined. The derivatives tested were colistin methanesulfonate (CMS), which lacks the polycationic domain, and polymyxin B nonapeptide (PMXB-9), which lacks the lipophilic domain.

PBMCs from 6 individual donors were stimulated with 20 µg/ml IMC oligonucleotide (5'-TGACTGTGAACGTTC-GAGATGA-3' (SEQ ID NO:1) or 20 µg/ml —ISS oligonucleotide (5'-TGCTTGCAAGCTTGCAAGCA-3'(SEQ ID NO:38), negative control) with or without 100 µg/ml PMXB, colistin (CLN), CMS, or PMXB-9 for 24 hours. For these assays, the ISS and the polymyxin were added separately to the PBMC cell culture which contained human serum albumin. The results are shown in Table 10.

TABLE 10

| stimulus | donor 1 | donor 2 | donor 3 | donor 4 | donor 5 | donor 6 | mean | SEM |
|---|---|---|---|---|---|---|---|---|
| IFN-γ (pg/ml) | | | | | | | | |
| medium | 2 | 2 | 2 | 2 | 2 | 2 | 2 | 0 |
| IMC | 13 | 3 | 2 | 2 | 99 | 14 | 22 | 16 |
| IMC + PMXB | 432 | 577 | 216 | 333 | 2000 | 461 | 670 | 271 |
| IMC + CLN | 858 | 2000 | 218 | 386 | 541 | 496 | 750 | 264 |
| IMC + CMS | 147 | 2 | 2 | 2 | 372 | 319 | 141 | 69 |
| IMC + PMXB-9 | 32 | 2 | 2 | 2 | 107 | 11 | 26 | 17 |
| −ISS | 2 | 2 | 2 | 2 | 10 | 2 | 3 | 1 |
| −ISS + PMXB | 94 | 84 | 74 | 3 | 225 | 50 | 88 | 30 |
| −ISS + CLN | 2 | 57 | 31 | 2 | 299 | 22 | 69 | 47 |
| −ISS + CMS | 2 | 2 | 2 | 2 | 15 | 23 | 8 | 4 |
| −ISS + PMXB-9 | 2 | 2 | 2 | 2 | 21 | 10 | 7 | 3 |
| IFN-α (pg/ml) | | | | | | | | |
| medium | 52 | 52 | 52 | 52 | 26 | 26 | 43 | 5 |
| IMC | 263 | 225 | 52 | 52 | 218 | 26 | 139 | 44 |
| IMC + PMXB | 8148 | 3275 | 3657 | 1003 | 8074 | 13160 | 6220 | 1805 |
| IMC + CLN | 10291 | 1972 | 1259 | 115 | 4187 | 4020 | 3641 | 1478 |
| IMC + CMS | 492 | 336 | 52 | 52 | 2152 | 290 | 562 | 325 |
| IMC + PMXB-9 | 1881 | 529 | 52 | 52 | 831 | 26 | 562 | 295 |
| −ISS | 52 | 52 | 52 | 52 | 26 | 26 | 43 | 5 |
| −ISS + PMXB | 52 | 52 | 52 | 52 | 26 | 26 | 43 | 5 |
| −ISS + CLN | 52 | 52 | 52 | 52 | 26 | 26 | 43 | 5 |
| −ISS + CMS | 52 | 52 | 52 | 52 | 26 | 26 | 43 | 5 |
| −ISS + PMXB-9 | 52 | 52 | 52 | 52 | 26 | 26 | 43 | 5 |

As shown in Table 10, although both CMS and PMXB-9 enhance the IFN-γ/α-stimulating activity of the IMC, both CMS and PMXB-9 exhibited substantially reduced IFN-γ/α-enhancing activity in comparison to PMXB or CLN. These data indicate that both the polycationic and lipophilic domains of the polymyxin molecule are necessary for optimal IMC-enhancing activity of polymyxin.

Example 6

Polymyxin Particulate Formulations and ISS Activity

In human PBMCs, IMC stimulation induces a well-defined and specific pattern of gene activation, including cytokines, chemokines, and antiviral factors. This pattern was examined during PMXB enhancement of IMC activity. Human PBMCs from 4 donors were stimulated for 4 and 10 hours with IMC with or without PMXB. Two different IMCs were tested: (5'-TGACTGTGAACGTTCGAGATGA-3' (SEQ ID NO:1) and (5'-TCGTCGAACGTTCGAGATGAT-3' (SEQ ID NO:39). For these assays, the IMC and the PMXB were added separately to the PBMC cell culture which contained human serum albumin. For the assessment of gene expression, cDNA was synthesized from RNA isolated from the cell suspensions and RNA was quantitated using TAQMAN® Technology. Expression of the following genes were assessed at these time points: IFN-γ and IFN-α, interferon-inducible protein-10 (IP-10), monokine induced by IFN-γ (MIG), 2,5-oligoadenylate synthetase (2,5-OAS) and interferon-stimulating gene-54K (ISG-54K). The results are presented in Table 11.

TABLE 11

| | | Fold Induction | | | | | | | | | | | |
|---|---|---|---|---|---|---|---|---|---|---|---|---|---|
| | | IFN-α | | 2,5-OAS | | ISG-54 K | | IFN-γ | | IP-10 | | MIG | |
| time | stimulus | mean | SEM | mean | SEM | mean | SEM | mean | SEM | mean | SEM | mean | SEM |
| 4 h | SEQ ID NO: 1 | 0.8 | 0.1 | 0.9 | 0.2 | 1.1 | 0.3 | 0.9 | 0.2 | 0.6 | 0.2 | 1.3 | 0.8 |
| | SEQ ID NO: 1 + PMXB | 2.4 | 1.1 | 1.4 | 0.4 | 2.5 | 0.7 | 5.0 | 3.0 | 7.7 | 4.1 | 14.0 | 7.7 |
| | SEQ ID NO: 39 | 2.3 | 1.1 | 1.0 | 0.3 | 1.4 | 0.4 | 0.9 | 0.3 | 0.7 | 0.3 | 1.2 | 0.5 |
| | SEQ ID NO: 39 + PMXB | 155.1 | 83.3 | 10.5 | 4.7 | 24.7 | 11.0 | 37.9 | 32.1 | 45.4 | 37.6 | 33.9 | 25.1 |
| 10 h | SEQ ID NO: 1 | 76.9 | 64.7 | 13.5 | 2.9 | 34.8 | 10.6 | 18.7 | 5.7 | 49.2 | 32.9 | 4.6 | 1.2 |
| | SEQ ID NO: 1 + PMXB | 2393 | 1217 | 29.0 | 3.2 | 105.1 | 21.3 | 461.8 | 183.9 | 105.0 | 64.8 | 34.6 | 14.8 |
| | SEQ ID NO: 39 | 6552 | 4156 | 105.3 | 16.0 | 455.3 | 129.6 | 100.4 | 10.3 | 512.6 | 169.8 | 47.3 | 17.1 |
| | SEQ ID NO: 39 + PMXB | 3463 | 1146 | 18.6 | 3.1 | 65.9 | 10.8 | 273.3 | 117.2 | 75.9 | 47.1 | 35.5 | 20.2 |

By 10 h of stimulation, PMXB clearly boosted the ability of IMC SEQ ID NO:1 to induce the expression of various genes including IFN-γ and IFN-α, chemokines such as IP-10 and MIG, and the antiviral genes 2,5-OAS and ISG-54K. IMC SEQ ID NO:39 displays accelerated kinetics of gene induction compared to IMC SEQ ID NO:1 and thus an earlier timepoint was chosen to look for enhancement by PMXB. By 4 h, PMXB was markedly enhancing the transcription-inducing activity of IMC SEQ ID NO:39 in similar fashion to IMC SEQ ID NO:1 at 10 h. Therefore, PMXB appears to increase the IMC-transduced signal for gene activation quantitatively but does not alter it qualitatively.

Example 7

IMC Particulate Formulations Enhance IFN-α Production from Plasmacytoind Dendritic Cells Intracellular staining assays and FACS analysis were used to examine IFN-α production from the plasmacytoind dendritic cells (PDCs) of human PBMCs. These assays were performed with 20 μg/ml IMC oligonucleotide 5'-TGACT-GTGAACGTTCGAGATGA-3' (SEQ ID NO:1) or 5'-TCGTCGAACGTTCGAGATGAT-3' (SEQ ID NO:39) or 20 μg/ml –ISS oligonucleotide (5'-TGCTTGCAAGCTTG-CAAGCA-3'(SEQ ID NO:38), negative control). For these assays, the IMC or –ISS and the polymyxin were added separately to the PBMC cell culture which contained human serum albumin.

Human PBMCs were stimulated with 20 μg/mL IMC or –ISS, with or without 100 μg/mL PMXB for six hours, the last two of which were also in the presence of brefeldin A, a reagent which prevents release of newly synthesized protein from the Golgi. After the six hours, the cells were stained with a fluorescently labeled PDC marker, anti-BCDA-2 labeled with FITC, and with anti-IFN-α labeled with PE. FACS analysis of the labeled cells was performed. The assay was performed with 2 different IMCs and the double-staining cell population (BCDA-2$^+$, IFN-α$^+$) as a percentage of total PBMCs is listed in Table 12.

TABLE 12

| | | BCDA-2/IFN-α d.p. % | | |
|---|---|---|---|---|
| sample | stimulus | donor 1 | donor 2 | mean |
| 1 | medium | 0.00 | 0.00 | 0.00 |
| 2 | IMC SEQ ID NO: 1 | 0.01 | 0.03 | 0.02 |
| 3 | –ISS SEQ ID NO: 38 | 0.00 | 0.00 | 0.00 |
| 4 | IMC SEQ ID NO: 39 | 0.08 | 0.14 | 0.11 |
| 5 | IMC SEQ ID NO: 1 + PMXB | 0.06 | 0.35 | 0.21 |
| 6 | –ISS SEQ ID NO: 38 + PMXB | 0.00 | 0.00 | 0.00 |
| 7 | IMC SEQ ID NO: 39 + PMXB | 0.21 | 0.39 | 0.30 |

As can be seen in Table 12, the percentage of double-staining cells was substantially increased when the PBMCs were treated with both of the IMCs in the presence of PMXB, but not with the –ISS oligonucleotide in the presence of PMXB. This result indicates that the enhanced IFN-α production from PBMCs observed in the presence of IMC/PMXB formulations is derived from PDCs. In addition, no detectable IFN-α production was observed in the BCDA-2$^-$ (non-PDC) fraction of cells.

Example 8

Induction of Natural Killer Cell Activity from Human Cells with Particulate Compositions The lytic activity of natural killer (NK) cells is activated by immunomodulatory polynucleotides. NK cells are indirectly activated by IMC through signals transmitted from the plasmacytoid dendritic cells (PDC). The exact nature of this signal has not yet been identified although IFN-α appears to play a major role in this signaling.

IMC particulate formulations were tested for NK cell stimulatory activity. PBMCs from two donors were stimulated for 48 hours with 10 μg/mL IMC ("+ISS") 5'-TGACT-GTGAACGTTCGAGATGA-3' (SEQ ID NO:1) with or without 100 μg/mL PMXB. The PBMCs were then assayed for lytic activity against K562 cells loaded with $^{51}$Cr as target cells. For controls, K562 cells were cultured alone, K562 cells were lysed with Triton and K562 cells were stimulated with untreated PBMC cells. Determination of $^{51}$CR released into culture media was used to measure the extent of target cell lysis. The presence of PMXB increased the NK cell lytic activity stimulated by the IMC alone. Results are summarized in Table 13.

TABLE 13

| | Effector: | donor 1 | | | | donor 2 | | | | mean of |
|---|---|---|---|---|---|---|---|---|---|---|
| stimulus | Target ratio | cpm1 | cpm2 | cpm3 | mean | cpm1 | cpm2 | cpm3 | mean | both |
| K562 alone | — | 4155 | 4378 | 4303 | 4279 | 4352 | 4262 | 4537 | 4384 | 4331 |
| K562 + Triton | — | 17136 | 17476 | 17576 | 17396 | 17701 | 17666 | 18231 | 17866 | 17631 |
| PBMC untreated | 50:1 | 6043 | 5953 | 5810 | 5935 | 7482 | 8103 | 7918 | 7834 | 6885 |
| PBMC untreated | 25:1 | 5764 | 5980 | 5924 | 5889 | 7124 | 7962 | 7720 | 7602 | 6746 |
| PBMC untreated | 12.5:1 | 6343 | 6659 | 6665 | 6556 | 5709 | 6190 | 6694 | 6198 | 6377 |
| PBMC untreated | 6:1 | 6668 | 6895 | 6643 | 6735 | 6319 | 6630 | 6671 | 6540 | 6638 |
| PBMC + IMC | 50:1 | 7660 | 7586 | 9169 | 8138 | 9975 | 9623 | 9660 | 9753 | 8946 |
| PBMC + IMC | 25:1 | 8205 | 8408 | 8048 | 8220 | 9263 | 9642 | 9149 | 9351 | 8786 |
| PBMC + IMC | 12.5:1 | 7412 | 7240 | 7344 | 7332 | 8370 | 8370 | 7745 | 8162 | 7747 |
| PBMC + IMC | 6:1 | 6935 | 6689 | 6473 | 6699 | 7181 | 7060 | 7122 | 7121 | 6910 |
| PBMC + IMC + PMXB | 50:1 | 10888 | 10634 | 11205 | 10909 | 11379 | 11292 | 11062 | 11244 | 11077 |
| PBMC + IMC + PMXB | 25:1 | 11048 | 10496 | 9981 | 10508 | 11835 | 10948 | 11935 | 11573 | 11041 |
| PBMC + IMC + PMXB | 12.5:1 | 8549 | 7582 | 7674 | 7935 | 10762 | 10311 | 9474 | 10182 | 9059 |
| PBMC + IMC + PMXB | 6:1 | 6999 | 6952 | 7227 | 7059 | 8471 | 8175 | 9185 | 8610 | 7835 |

Example 9

In Vivo Immunomodulation with Particulate Compositions in Mice

Immune responses to hepatitis B surface antigen (HBsAg) in combination with either an IMC ("+ISS") particulate formulation or plain +ISS were measured in mice. The IMC ("+ISS") had the sequence 5'-TGACTGTGAACGTTC-GAGATGA-3' (SEQ ID NO:1) and was a fully modified phosphorothioate oligodeoxynucleotide.

Particulate formulations were produced by first preparing either a 1 mg/ml oligonucleotide, 0.4% TWEEN® 85, 0.4% oleate solution, or a 1 mg/ml oligonucleotide, 20 mg/mL HSA solution, then making that solution 5 mg/ml in PMXB. The formulations were allowed to stand for 24 hours at room temperature before use. HBsAg was added to the formulations prior to injection. HBsAg alone and HBsAg with +ISS were used as controls.

Mice (BALB/c) were divided into groups of 10 and dosed with the test articles (5 µg of +ISS and 1 µg of HBsAg) by intramuscular injection at weeks zero and two. Serum samples were obtained by tail bleed at weeks two and four. All mice were euthanized at week six.

Serum samples were assayed for IgG1 and IgG2a titers by ELISA. Mice receiving the particulate formulations showed significantly greater IgG2a titers, indicative of a Th1 response. Week two and four antibody titers (reciprocal of the sample dilution at the cut-off OD) are summarized in Table 14 as titer ±standard deviation.

TABLE 14

| | IgG1 Titer (×10³) | | IgG2a Titer (×10³) | |
|---|---|---|---|---|
| Test Article | Week 2 | Week 4 | Week 2 | Week 4 |
| HBsAg alone | 0.06 ± 0.09 | 6 ± 6 | 0.03 ± .002 | 2.5 ± 2.6 |
| HBsAg/+ISS | 0.09 ± 0.12 | 3.8 ± 3.6 | 0.23 ± 0.25 | 43.6 ± 35.9 |
| HBsAg/+ISS/HSA/PMXB | 0.46 ± 0.66 | 29.3 ± 18.5 | 3.8 ± 3.3 | 217.7 ± 261.1 |
| HBsAg/+ISS/Tween/Oleate/PMXB | 0.58 ± 0.87 | 24.9 ± 10.2 | 6.3 ± 3.8 | 351.2 ± 207.9 |

Splenocytes were isolated from spleens harvested from the euthanized mice and assayed individually for antigen-stimulated cytokine release or peptide-stimulated cytolytic activity.

Cytokine release was measured by culturing cells from 10 animals per group in RPMI 1640 plus 10% FCS at 5×10⁵ splenocytes/well in 96 well flat bottomed plates. Cells were cultured for four days in the presence of 5 µg/mL HBsAg, medium alone (negative control) or PMA/ionomycin (positive control). Medium was collected and assayed for IFN-γ and IL-5 levels. Splenocytes from animals treated with either of the immunomodulatory formulations showed increased IFN-γ release and decreased IL-5 release. Results are summarized in Table 15.

TABLE 15

| | IFN-γ (ng/ml) | | IL-5 (ng/ml) | |
|---|---|---|---|---|
| Immunogen | Medium | HBsAg | Medium | HBsAg |
| HBsAg alone | 1.4 ± 1.5 | 4.7 ± 6.8 | 0.1 ± 0.1 | 1 ± 1.7 |
| HBsAg/+ISS | 1.6 ± 1.5 | 42 ± 23 | 0.1 ± 0.06 | 0.1 ± 0.1 |
| HBsAg/+ISS/HSA/PMXB | 3.1 ± 2.5 | 35.7 ± 17.8 | 0.3 ± 0.3 | 0.6 ± 0.5 |
| HBsAg/+ISS/Tween/Oleate/PMXB | 1.4 ± 0.7 | 27.5 ± 22.7 | 0.1 ± 0.2 | 0.1 ± 0.2 |

Splenocytes from five animals in each group were resuspended in RPMI 1640 plus 10% FCS at 3×10⁷ cells per well and were incubated for four days with or without the peptide IPQSLDSWWTSL (SEQ ID NO:41), a hepatitis B virus CTL epitope at 1 µg/mL. Cells were washed and diluted to 4×10⁶ cells/mL, transferred to antibody-coated ELISPOT plates, and incubated five to sixteen hours. After incubation, the cells were lysed with deionized water, reacted with either anti-IL-4 or anti-IFN-γ antibodies, and scored for positive cells (spot forming units, SFU). Splenocytes from animals treated with the particulate formulations had increased numbers of IFN-γ positive cells and increased ratios of IFN-γ:IL-4 producing cells. Results are summarized in Table 16 (expressed as positive cells/10⁵ cells).

TABLE 16

| | IL-4 (SFU per 10⁵ cells) | | IFN-γ (SFU per 10⁵ cells) | |
|---|---|---|---|---|
| | +Peptide | −Peptide (cells alone) | +Peptide | −Peptide (cells alone) |
| Controls | | | | |
| HBsAg alone | 8 ± 5 | 4 ± 2 | 38 ± 17 | 46 ± 27 |
| HBsAg/+ISS | 2 ± 1 | 6 ± 3 | 38 ± 22 | 34 ± 20 |
| Formulations | | | | |
| HBsAg/+ISS/HSA/PMXB | 20 ± 14 | 22 ± 13 | 63 ± 24 | 32 ± 18 |
| HBsAg/+ISS/Tween/Oleate/PMXB | 4 ± 1 | 4 ± 1 | 49 ± 10 | 10 ± 3 |

Splenocytes from the remaining five animal in each group were suspended in 15 mL of RPMI 1640 plus 10% FCS. Twelve milliliters of the suspension was divided into 6 wells of a 12 well plate. The remaining cell suspension was mixed with 1 µg/mL of the CTL peptide IPQSLDSWWTSL (SEQ ID NO:41), diluted with three volumes of 5.33% Rat T-Stim, and divided among the previously plated, unstimulated cells. The cultures were incubated for four days, washed with 2% Rat T-Stim, replated, and incubated a further two days. Effector cells generated by this process were assayed against MHC-matched cells loaded with $Cr^{51}$ or $Cr^{51}$ and the CTL peptide IPQSLDSWWTSL (SEQ ID NO:41). Cells from animals treated with +ISS (either in solution or in a particulate formulation) plus HBsAg demonstrated killing of >70% of target cells. Results are summarized in Table 17.

TABLE 17

| | % Lysis Effector:Target Ratio | | | MHC-matched, no peptide |
|---|---|---|---|---|
| Immunization Group | 40:1 | 10:1 | 2.5:1 | 40:1 |
| HBsAg alone | 1 ± 3 | 0 ± 0 | 0 ± 0 | 0 ± 0 |
| HBsAg/+ISS | 91 ± 42 | 38 ± 22 | 7 ± 7 | 0 ± 0 |
| HBsAg/+ISS/HSA/PMXB | 71 ± 35 | 30 ± 26 | 4 ± 3 | 0 ± 0 |

TABLE 17-continued

|  | % Lysis Effector:Target Ratio | | | MHC-matched, no peptide |
|---|---|---|---|---|
| Immunization Group | 40:1 | 10:1 | 2.5:1 | 40:1 |
| HBsAg/+ISS/Tween/Oleate/PMXB | 87 ± 13 | 33 ± 16 | 3 ± 2 | 0 ± 0 |

Example 10

Immunomodulation of Mouse Lung Cells with Particulate Compositions

Modulation of a variety of genes in response to immunomodulatory formulations was measured in mouse lung cells.

Particulate formulations were produced by first preparing either a 1 mg/mL +ISS, 0.4% TWEEN® 85, 0.4% oleate solution or a 20 mg/mL HSA solution, then making that solution 5 mg/ml in PMXB. The formulations were allowed to stand for 24 hours at room temperature, then dialyzed using a 10 kDa membrane. Particulate formulations and +ISS alone (50 µL dose) were administered by intranasal instillation to lightly anesthetized mice (5 mice per group). Animals were sacrificed 6 hours after administration, lung tissue was surgically removed, and cell suspensions were made by homogenization of the lung tissue. cDNA was synthesized from RNA isolated from the cell suspensions, and RNA was quantitated using TAQMAN® Technology. The particulate formulations induced significant increases in the majority of the genes tested. Results are summarized in Table 18.

TABLE 18

| Gene | Relative Cycle Thresholds (CTs) | | | |
|---|---|---|---|---|
|  | +ISS | +ISS/HSA | +ISS/Tween | +ISS/Tween/Oleate |
| IL-1a | 7523 | 19808 | 16318 | 6487 |
| IL-1b | 1643 | 5224 | 3815 | 1496 |
| IL-6 | 755 | 1022 | 828 | 329 |
| IL-10 | 4 | 21 | 16 | 7 |
| IL-12p40 | 6 | 40 | 25 | 9 |
| IL-23 | 266 | 322 | 269 | 85 |
| IFN-α2 | 3 | 7 | 2 | 2 |
| IFN-γ | 25 | 105 | 75 | 25 |
| TNF-α | 7170 | 14367 | 11004 | 3095 |
| G-CSF | 92 | 102 | 111 | 29 |
| BCA-1 | 5026 | 6102 | 6025 | 2711 |
| Eotaxin | 273 | 838 | 649 | 350 |
| IP-10 | 23436 | 70759 | 34996 | 17925 |
| LPTN | 976 | 2254 | 1742 | 816 |
| MCP-1 | 5265 | 10897 | 9629 | 4102 |
| MCP-3 | 3905 | 6549 | 6419 | 2596 |
| MDC | 2869 | 6642 | 4217 | 1967 |
| MIG | 3411 | 10971 | 5826 | 2389 |
| MIP-1a | 6156 | 7557 | 6449 | 2553 |
| MIP-1b | 12918 | 22326 | 18235 | 6117 |
| MIP-2 | 1792 | 3545 | 3414 | 1201 |
| MIP-3a | 885 | 16998 | 1594 | 684 |
| MIP-3b | 2030 | 3338 | 2815 | 1411 |
| TARC | 1505 | 2732 | 3202 | 1286 |
| TCA-3 | 16 | 40 | 32 | 10 |
| NOS2 | 308 | 1038 | 669 | 354 |
| COX-1 | 2145 | 2041 | 1554 | 1262 |
| COX-2 | 446 | 1380 | 1475 | 642 |
| 12/15-lipoxg | 65 | 249 | 166 | 179 |
| CD80 | 205 | 763 | 453 | 256 |
| CD86 | 103 | 429 | 254 | 231 |
| MMP-8 | 1505 | 1928 | 1499 | 653 |

Example 11

Particulate Formulations and HBsAg Antibody Responses in Primates

Immune responses to the surface antigen of hepatitis B virus (HBsAg) combined with the particulate PMXB/+ISS/Tween/Oleate (Tween) formulation were measured in baboons. Particulate formulations were produced by first preparing a 1 mg/ml oligonucleotide, 0.4% TWEEN® 85, 0.4% oleate solution, then making that solution 5 mg/ml in PMXB. The formulation was allowed to stand for 24 hours at room temperature before administration. HBsAg (20 μg) was added to the formulation prior to injection. HBsAg alone and HBsAg with +ISS were used as controls.

Groups of 5-10 animals were immunized intramuscularly at week 0 and 8 with HBsAg alone (20 μg, n=5), HBsAg(20 μg)+ISS (SEQ ID NO:1) (1000 μg, n=5), or HBsAg 20 μg+the Tween formulation (1000 μg +ISS (SEQ ID NO:1), n=10). Two weeks after each immunization, baboons were bled and serum samples collected.

HBsAg specific antibody responses were quantified from the serum samples using the AUSAB enzyme immunoassay from Abbott Laboratories. In humans, a titer of 10 mIU/ml is considered protective. The results are summarized in Table 19 as the geomean of each group ±SE.

TABLE 19

| Immunization Group | Post 1$^{st}$ Imm Anti-HBsAg (mIU/ml) | Post 2$^{nd}$ Imm Anti-HBsAg (mIU/ml) |
|---|---|---|
| HBsAg alone (20 μg) | 0 ± 2 | 4 ± 24 |
| HBsAg (20 μg) + +ISS (1000 μg) | 8 ± 6 | 260 ± 3,939 |
| HBsAg (20 μg) + Tween formulation (1000 μg +ISS) | *26 ± 269 | *797 ± 1,326 |

*p < 0.05 vs HBsAg alone by Kruskal-Wallis test

Immunization of baboons with HBsAg+the Tween formulation induced statistically higher HBsAg specific antibody responses following both the first and second immunizations compared to HBsAg alone immunized animals. This data indicates that in addition to enhancing immune responses in mice as previously shown, the particulate Tween formulation also enhances immune responses in primate species.

Example 12

Lyophilization of Immunomodulatory Compositions

A 10 mL batch of an immunomodulatory composition was produced by mixing 0.4 mL of 10% oleic acid (in water), 4 mL of 1% Tween 85 (in water), 1 mL of 20 mg/ml +ISS (SEQ ID NO:1) and 3.6 ml Dulbecco Modified Phosphate Buffered Saline. After thorough mixing, 1 mL of 50 mg/mL PMXB sulfate was slowly added with vortex mixing. 816 mg of sucrose were dissolved into 8 mL of the suspension which was allowed to stand overnight. Particles were resuspended by vortexing and the material was divided into 2 ml aliquots. Two of the aliquots were frozen by immersion of the vial into dry ice/ethanol. One aliquot was lyophilized overnight in a LABCONCO Freezone 4.5 freeze dryer under ~0.06 mBar pressure. The sample was stored 2 weeks at room temperature before resuspension in deionized water. Analysis of the reconstituted composition showed that the size distribution of particles in the suspension was equivalent to the unlyophilized time zero control sample.

Example 13

Antibody Responses to Lyophilized Particulate Formulations

Immune responses to HBsAg in combination with a lyophilized particulate Tween (PMX/+ISS/Tween/Oleate) formulation were measured in mice. Groups of 10 BALB/c mice were immunized intradermally with 1 μg doses of HBsAg alone, HBsAg mixed with 1 or 5 μg +ISS (SEQ ID NO:1), or HBsAg mixed with the lyophilized ($_{lyo}$Tween) formulation made as described in Example 12 but with 1 or 5 μg+ISS oligonucleotide (SEQ ID NO:1). Animals received 2 immunizations at a two week interval. Two weeks after each immunization, mice were bled and serum samples collected.

Serum samples were assayed for HBsAg-specific IgG1 and IgG2a responses by ELISA. In the mouse, the IgG2a subclass is induced by Th1 responses. The antibody titers are summarized as mean titer for each group ±SD in Table 20.

TABLE 20

| Immunization Group | IgG1 Titers Post 1$^{st}$ Imm | IgG2a Titers Post 1$^{st}$ Imm | IgG1 Titers Post 2nd Imm | IgG2a Titers Post 2nd Imm |
|---|---|---|---|---|
| HBsAg alone (1 μg) | 71 ± 73 | 46 ± 47 | 10,345 ± 8,397 | 2,122 ± 2,479 |
| HBsAg (1 μg) + +ISS (1 μg) | 84 ± 98 | 324 ± 331 | 5,797 ± 5,256 | 25,561 ± 35,909 |
| HBsAg (1 μg) + $_{lyo}$Tween formulation (1 μg +ISS) | 282 ± 348 | **1,583 ± 1,359 | 17,257 ± 15,405 | **81,280 ± 47,435 |
| HBsAg (1 μg) + +ISS (5 μg) | 44 ± 26 | 171 ± 234 | 4,179 ± 3,494 | 31,323 ± 29,455 |
| HBsAg (1 μg) + $_{lyo}$Tween formulation (5 μg +ISS) | *†739 ± 604 | **†7,461 ± 7,004 | *‡30,498 ± 16,940 | **†274,491 ± 243,949 |

*p < 0.01,
**p < 0.001 vs HBsAg alone by Kruskal-Wallis test
†p < 0.05,
‡p < 0.001 vs HBsAg + ISS by Kruskal-Wallis test The IgG1, and especially the IgG2a titers are dramatically enhanced in mice that received the HBsAg+lyophilized Tween formulations following both the first and second immunizations compared to animals immunized with HBsAg alone demonstrating that the lyophilized Tween formulation has the same ability to enhance immune responses seen with the non-lyophilized Tween formulation.

---

What is claimed is:

1. An immunostimulatory particulate composition comprising a cationic condensing agent, an immunostimulatory compound, and a nonionic detergent;
   wherein the cationic condensing agent is a cationic lipopeptide; and
   wherein the immunostimulatory compound comprises an immunostimulatory sequence (ISS), wherein the ISS comprises nucleotide sequence 5'-CG-3', wherein the cytosine of the nucleotide sequence 5'-CG-3' is unmethylated and the ISS is greater than about 6 base pairs in length and is less than about 100 base pairs in length.

2. The composition of claim 1, wherein said cationic condensing agent is selected from the group consisting of polymyxins, circulins, octapeptin, and amphotericins.

3. The composition of claim 2, wherein said cationic condensing agent is a polymyxin.

4. The composition of claim 3, wherein said cationic condensing agent is polymyxin B.

5. The composition of claim 1, wherein said nonionic detergent is a polyoxyethylenesorbitan detergent.

6. The composition of claim 5, wherein said polyoxyethylenesorbitan detergent is polyoxyethylenesorbitan trioleate.

7. The composition of claim 1, wherein said particulate composition further comprises a fatty acid.

8. The composition of claim 7, wherein said fatty acid is a salt of oleic acid.

9. A pharmaceutical composition comprising:
   a aqueous suspension of immunostimulatory particles, said composition comprising an immunostimulatory compound, a nonionic detergent, and a cationic condensing agent;
   wherein the cationic condensing agent is a cationic lipopeptide; and
   wherein the immunostimulatory compound comprises an immunostimulatory sequence (ISS), wherein the ISS comprises sequence 5'-CG-3', wherein the cytosine of the sequence 5'-CG-3' is unmethylated and the ISS is greater than about 6 base pairs in length and is less than about 100 base pairs in length.

10. The composition of claim 9, wherein said cationic condensing agent is selected from the group consisting of polymyxins, circulins, octapeptin, and amphotericins.

11. The composition of claim 10, wherein said cationic condensing agent is a polymyxin.

12. The composition of claim 11, wherein said cationic condensing agent is polymyxin B.

13. The composition of claim 9, wherein said nonionic detergent is a polyoxyethylenesorbitan detergent.

14. The composition of claim 13, wherein said polyoxyethylenesorbitan detergent is polyoxyethylenesorbitan trioleate.

15. The composition of claim 9, wherein said particulate composition further comprises a fatty acid.

16. The composition of claim 15, wherein said fatty acid is a salt of oleic acid.

17. The composition of claim 9, further comprising an antigen.

18. The composition of claim 17, wherein said antigen is selected from the group consisting of allergens and antigens associated with infectious agents.

19. An immunostimulatory particulate suspension comprising an immunostimulatory compound, a nonionic detergent, and a cationic condensing agent made by the process comprising:
  (a) combining the immunostimulatory compound comprising an immunostimulatory sequence (ISS), wherein the ISS comprises sequence 5'-CG-3', wherein the cytosine of the sequence 5'-CG-3' is unmethylated and the ISS is greater than about 6 base pairs in length and is less than about 100 base pairs in length and said nonionic detergent, thereby forming an immunostimulatory compound/nonionic detergent mixture,
  (b) combining the cationic condensing agent, wherein said cationic condensing agent is a cationic lipopeptide, with said immunostimulatory compound/nonionic detergent mixture, and
  (c) collecting the immunostimulatory particulate suspension.

20. A method of stimulating an immune response in an individual comprising:
  administering to an individual the immunostimulatory particulate composition of claim 1 in an amount sufficient to stimulate an immune response in said individual.

21. An immunostimulatory particulate composition comprising immunostimulatory particles, said composition comprising polymyxin, an immunostimulatory compound, and a stabilizing agent;
  wherein said immunostimulatory compound comprises an immunostimulatory sequence (ISS), wherein the ISS comprises nucleotide sequence 5'-CG-3', wherein the cytosine of the nucleotide sequence 5'-CG-3' is unmethylated and the ISS is greater than about 6 base pairs in length and is less than about 100 base pairs in length; and
  wherein said stabilizing agent is not a bovine serum protein.

22. The composition of claim 21, wherein said stabilizing agent is selected from the group consisting of proteins, nonionic detergents, polymeric surfactants, cationic detergents, anionic detergents and fatty acids.

23. The composition of claim 22, wherein said stabilizing agent is a nonionic detergent.

24. The composition of claim 23, wherein said nonionic detergent is a polyoxyethylenesorbitan detergent.

25. The composition of claim 23, wherein said polyoxyethylenesorbitan detergent is polyoxyethylenesorbitan trioleate.

26. The composition of claim 21, wherein said polymyxin is polymyxin B.

27. The composition of claim 21, wherein said particulate composition further comprises a fatty acid.

28. The composition of claim 27, wherein said fatty acid is a salt of oleic acid.

29. The composition of claim 21, wherein said immunostimulatory compound comprises the nucleotide sequence 5'-TCG-3'.

30. The composition of claim 21, wherein said immunostimulatory compound comprises the nucleotide sequence 5'-purine, purine, C, G, pyrimidine, pyrimidine-3'.

31. The composition of claim 21, wherein said immunostimulatory compound comprises at least 14 nucleotides.

32. A pharmaceutical composition comprising an aqueous suspension of immunostimulatory particles, said composition comprising polymyxin, a stabilizing agent, and an immunostimulatory compound;
  wherein said immunostimulatory compound comprises an immunostimulatory sequence (ISS), wherein the ISS comprises nucleotide sequence 5'-CG-3', wherein the cytosine of the nucleotide sequence 5'-CG-3' is unmethylated and the ISS is greater than about 6 base pairs in length and is less than about 100 base pairs in length; and
  wherein said stabilizing agent is not a bovine serum protein.

33. An immunostimulatory particulate suspension comprising an immunostimulatory compound, a stabilizing agent, and polymyxin made by the process comprising:
  (a) combining said immunostimulatory compound comprising an immunostimulatory sequence (ISS), wherein the ISS comprises the sequence 5'-CG-3', wherein the cytosine of the sequence 5'-CG-3' is unmethylated and the ISS is greater than about 6 base pairs in length and is less than about 100 base pairs in length and said stabilizing agent, thereby forming an immunostimulatory/stabilizing agent mixture,
  (b) combining polymyxin with said immunostimulatory/stabilizing agent mixture, and
  (c) collecting the immunostimulatory particulate suspension.

34. A method of stimulating an immune response in an individual comprising:
administering to an individual the immunostimulatory particulate composition of claim 33, in an amount sufficient to stimulate an immune response in said individual.

35. An immunostimulatory particulate composition comprising immunostimulatory particles, said particulate composition comprising a cationic condensing agent, an immunostimulatory polynucleotide, an antigen, and a stabilizing active agent;
  wherein said immunostimulatory polynucleotide comprises an immunostimulatory sequence (ISS), wherein the ISS comprises sequence 5'-CG-3', wherein the cytosine of the sequence 5'-CG-3' is unmethylated and the ISS is greater than about 6 base pairs in length and is less than about 100 base pairs in length.

36. A pharmaceutical composition comprising an antigen, an aqueous suspension of immunostimulatory particles, and a stabilizing agent,
  wherein said particles comprises a cationic condensing agent, an immunostimulatory polynucleotide, and a stabilizing agent;
  wherein the cationic condensing agent is a cationic lipopeptide; and
  wherein the immunostimulatory polynucleotide comprises an immunostimulatory sequence (ISS), wherein the ISS comprises sequence 5'-CG-3', wherein the cytosine of the sequence 5'-CG-3' is unmethylated and the ISS is greater than about 6 base pairs in length and is less than about 100 base pairs in length.

37. A method of stimulating an immune response in an individual comprising: administering to an individual the immunostimulatory particulate composition of claim 35 in an amount sufficient to stimulate an immune response in said individual.

* * * * *

UNITED STATES PATENT AND TRADEMARK OFFICE
CERTIFICATE OF CORRECTION

PATENT NO.       : 7,884,083 B2
APPLICATION NO.  : 10/640172
DATED            : February 8, 2011
INVENTOR(S)      : Gary Van Nest et al.

Page 1 of 1

It is certified that error appears in the above-identified patent and that said Letters Patent is hereby corrected as shown below:

In Claim 34:

Column 102, lines 32-36; please replace "A method of stimulating an immune response in an individual comprising: administering to an individual the immunostimulatory particulate composition of claim 33, in amount sufficient to stimulate an immune response in said individual." with --A method of stimulating an immune response in an individual comprising: administering to an individual the immunostimulatory particulate composition of claim 21, in amount sufficient to stimulate an immune response in said individual.--.

Signed and Sealed this
Tenth Day of May, 2011

David J. Kappos
*Director of the United States Patent and Trademark Office*